(12) United States Patent
Cinar et al.

(10) Patent No.: US 10,646,650 B2
(45) Date of Patent: May 12, 2020

(54) MULTIVARIABLE ARTIFICIAL PANCREAS METHOD AND SYSTEM

(71) Applicants: Ali Cinar, Wilmette, IL (US); Kamuran Turksoy, Chicago, IL (US); Iman Hajizadeh, Chicago, IL (US)

(72) Inventors: Ali Cinar, Wilmette, IL (US); Kamuran Turksoy, Chicago, IL (US); Iman Hajizadeh, Chicago, IL (US)

(73) Assignee: ILLINOIS INSTITUTE OF TECHNOLOGY, Chicago, IL (US)

( * ) Notice: Subject to any disclaimer, the term of this patent is extended or adjusted under 35 U.S.C. 154(b) by 577 days.

(21) Appl. No.: 15/171,355

(22) Filed: Jun. 2, 2016

(65) Prior Publication Data

US 2016/0354543 A1 Dec. 8, 2016

Related U.S. Application Data

(60) Provisional application No. 62/169,947, filed on Jun. 2, 2015.

(51) Int. Cl.
| | | |
|---|---|---|
| *A61M 5/172* | (2006.01) | |
| *A61B 5/145* | (2006.01) | |
| *A61M 5/142* | (2006.01) | |
| *A61B 5/00* | (2006.01) | |
| *G16H 40/63* | (2018.01) | |
| *G06F 19/00* | (2018.01) | |

(52) U.S. Cl.
CPC ....... *A61M 5/1723* (2013.01); *A61B 5/14532* (2013.01); *A61B 5/7275* (2013.01); *A61M 5/142* (2013.01); *G06F 19/00* (2013.01); *G16H 40/63* (2018.01); *A61B 5/14503* (2013.01); *A61B 2560/0276* (2013.01); *A61M 2005/14208* (2013.01); *A61M 2205/3523* (2013.01); *A61M 2205/50* (2013.01); *A61M 2230/201* (2013.01)

(58) Field of Classification Search
CPC .................................................. A61M 5/1723
USPC ....................................................... 702/19
See application file for complete search history.

(56) References Cited

U.S. PATENT DOCUMENTS

| | | | |
|---|---|---|---|
| 4,475,901 A | 10/1984 | Kraegen et al. | |
| 4,498,843 A | 2/1985 | Schneider et al. | |
| 6,572,542 B1 | 6/2003 | Houben et al. | |
| 6,923,763 B1* | 8/2005 | Kovatchev | A61B 5/14532 |
| | | | 600/300 |
| 7,402,153 B2 | 7/2008 | Steil et al. | |
| 8,690,820 B2 | 4/2014 | Cinar et al. | |
| 2003/0050621 A1 | 3/2003 | Lebel et al. | |
| 2003/0114836 A1 | 6/2003 | Estes et al. | |
| 2003/0208113 A1 | 11/2003 | Mault et al. | |
| 2004/0034295 A1 | 2/2004 | Salganoff et al. | |
| 2005/0080322 A1 | 4/2005 | Korman | |
| 2005/0119540 A1 | 6/2005 | Potts et al. | |
| 2006/0079809 A1 | 4/2006 | Goldberger et al. | |
| 2007/0060870 A1 | 3/2007 | Tolle et al. | |
| 2007/0173761 A1 | 7/2007 | Kanderian, Jr. et al. | |
| 2007/0270672 A1 | 11/2007 | Hayter | |
| 2008/0014601 A1 | 1/2008 | Goldberger et al. | |
| 2008/0188796 A1 | 8/2008 | Steil et al. | |
| 2008/0300572 A1 | 12/2008 | Rankers et al. | |
| 2008/0306434 A1 | 12/2008 | Dobbles et al. | |
| 2009/0069787 A1 | 3/2009 | Estes et al. | |
| 2009/0227855 A1 | 9/2009 | Hill et al. | |
| 2009/0312621 A1 | 12/2009 | Lebel et al. | |
| 2011/0040487 A1 | 2/2011 | Hovorka | |
| 2011/0046887 A1 | 2/2011 | Veldhuise et al. | |
| 2012/0059353 A1* | 3/2012 | Kovatchev | G06F 19/3456 |
| | | | 604/504 |
| 2016/0066894 A1* | 3/2016 | Barton-Sweeney | ......... |
| | | | A61B 5/02055 |
| | | | 600/301 |

FOREIGN PATENT DOCUMENTS

| | | |
|---|---|---|
| EP | 1 177 802 A1 | 2/2002 |
| EP | 1 759 726 A2 | 3/2007 |
| WO | WO 96/37246 A1 | 11/1996 |
| WO | WO 00/74753 A1 | 12/2000 |
| WO | WO 2008/114254 A1 | 9/2008 |
| WO | WO 2008/135329 A1 | 11/2008 |

(Continued)

OTHER PUBLICATIONS

Riddell et al. (Exercise and Glucose Metabolism in Persons with Diabetes Mellitus: Perspectives on the Role for Continuous Glucose Monitoring; Journal of Diabetes Science and Technology, Jul. 2009, vol. 3, Iss. 4, 914-923);.*

(Continued)

*Primary Examiner* — Jerry Lin

(74) *Attorney, Agent, or Firm* — Pauley Erickson & Kottis

(57) ABSTRACT

Methods and modules for using physiological (biometric) variables to advance the state of the artificial pancreas. The method and system includes one or more modules for recursive model identification, hypoglycemia early alert and alarm, adaptive control, hyperglycemia early alert and alarm, plasma insulin concentration estimation, assessment of physical activity (e.g., presence, type, duration, expected effects on insulin sensitivity and GC), detection of acute stress and assessment of its impact on insulin sensitivity, detection of sleep and its stages and assessment of sleep stages on GC, sensor fault detection and diagnosis, software and controller performance evaluation and adjustment and/or pump fault detection and diagnosis.

21 Claims, 27 Drawing Sheets

(56) References Cited

FOREIGN PATENT DOCUMENTS

WO     WO 2008/154312 A1     12/2008
WO     WO 2009/023407 A1     2/2009

OTHER PUBLICATIONS

Van Cauter et al. (Roles of Circadian Rhythmicity and Sleep in Human Glucose Regulation; Endocrine Reviews, Oct. 1997, 18(5):716-738).*

* cited by examiner

MULTIVARIABLE ARTIFICIAL PANCREAS METHOD AND SYSTEM

CROSS REFERENCE TO RELATED APPLICATION

This application claims the benefit of U.S. Provisional Application Ser. No. 62/169,947, filed on 2 Jun. 2015. The co-pending Provisional Application is hereby incorporated by reference herein in its entirety and is made a part hereof, including but not limited to those portions which specifically appear hereinafter.

GOVERNMENT SUPPORT

This invention was made with government support under 1DP3DK101077-01 and 1DP3DK101075-01 awarded by the National Institutes of Health. The government has certain rights in the invention.

FIELD OF THE INVENTION

This invention relates generally to artificial pancreas (AP) that can regulate glucose concentrations (GC) without manual inputs from a patient with Type 1 diabetes (T1D). Major factors that cause variations in GC include meals, physical activity, acute stress and sleep.

BACKGROUND OF THE INVENTION

Patients with Type 1 diabetes (T1D) must receive insulin from external sources in order to regulate their blood glucose concentration (BGC). Excess glucose in the blood can damage the blood vessels. This leads to several complications such as cardiovascular disease, damage to kidneys, nerves, and eyes, and difficulty in wound healing. Diabetes is the fastest growing long-term disease that affects millions of people worldwide. Diabetes affects 25.8 million people in United States and about 5% of diabetes cases are T1D in adults. Diabetes is considered to be the seventh leading cause of death in the United States and the cost of diabetes to the nation has been estimated to be $174 billion in 2007.

Most patients with T1D either administer multiple (3-5) daily insulin injections (MDI) or use insulin pumps for continuous subcutaneous insulin infusion (CSII). In CSII, basal insulin is infused continuously and bolus insulin is administered before meals to maintain BGC in the target range (70-180 mg/dl). T1D patients may experience hypoglycemia (BGC≤70 mg/dl) episodes that may be caused by insulin doses that are too large in relation to the BGC, reduced food intake, extensive physical activity, or slow absorption of currently available "fast acting" insulins. Hypoglycemia causes dizziness, unconsciousness, and seizures and if untreated diabetic coma or death. Fear of hypoglycemia is prevalent among patients with T1D and a concern in use of insulin pumps.

An artificial pancreas (AP) will automate insulin pumps by using a controller that receives information from sensors, computes the optimal insulin amount to be infused and manipulates the infusion rate of the pump. Fear of hypoglycemia is a major concern when the insulin infusion rate is under automatic control. An AP that can predict BGC accurately and compute infusion rates that will keep BGC in the target range without causing hypoglycemia would be very beneficial. Control systems that minimize the information to be entered by the user to the AP such as meal and exercise information would make life easier for patients with T1D.

Various control strategies such as proportional-integral derivative (PID) control, model predictive control (MPC), fuzzy logic control, and generalised predictive control (GPC) have been proposed for the regulation of BGC in patients with T1D. Furthermore, a bihormonal system (insulin+glucagon) that uses PID, MPC, and GPC has also been investigated. Complexity of glucose homeostasis and the current level of technology prevents tight BGC regulation. BGC dynamics are subject specific and time varying. Since a single good model that describes BGC dynamics of individuals does not exist, models have to be developed based on measurements from individuals. A single model based on some training data is not sufficient for controller design since BGC dynamics are time varying for each individual. Also a model based on data from one person would not be suitable for representing the BGC dynamics of another person. Recursive time-series models were shown to be a powerful tool for describing and predicting the dynamics of BGC, hypoglycemia alarm systems, and closed-loop control. There is a continuing need for improved recursive model development, guaranteed stability of every model developed, and adaptive control based on these recursive models.

Meals, physical activity, and emotional state are some of the factors that affect BGC. Using information from such factors improves the performance of BGC regulation. Meal information is used by many researchers to compute the amount of insulin bolus to be infused. However, use of information manually entered by patients should be balanced with convenience and adherence. Patients may forget to enter meal information in a timely manner or make erroneous estimates about the carbohydrate content of the meal. The protein, fat, and carbohydrate ratios of the foods impact the glycemic value of the meal ingested. Thus there is a continuing need for improved method and systems for an artificial pancreas.

SUMMARY OF THE INVENTION

A general object of this invention is to provide additional methods and modules for rising physiological (i.e., biometric) variables to advance the state of the artificial pancreas in several ways including, without limitation: (1) determining the presence of major factors (e.g., meals, physical activity, acute stress and/or sleep) that affect GC without receiving any manual inputs from patients, and the assessment of the current state of the patient is used to modify the control policies to accommodate the effects of these factors; and/or (2) detecting errors in the components and operation of the AP system in order to achieve an AP that can function in presence of various equipment errors and limitations in control algorithms.

The general object of the invention can be attained, at least in part, through a method for monitoring and/or treating glucose levels of a patient with diabetes, and a device or system for implementing the method. In embodiments of this invention, the method includes: automatically monitoring a glucose concentration level in the patient with a continuous glucose monitor worn by the patient to obtain a measured glucose level; automatically monitoring physiological variables of the patient using at least one physiological sensor worn by the patient to obtain measured physiological variables; automatically determining a physiological state of the patient from the measured physiological variables; and automatically estimating a future glucose level of the patient as a function of the measured glucose level, at least one of the measured physiological variables, and the determined physiological state of the patient.

In one embodiment, automatically determining a physiological state of the patient includes automatically matching the measured physiological variables to one of a plurality of predetermined classified physiological states. An exemplary physiological state according to this invention is physical activity, and the invention can include automatically determining an intensity and/or duration of the exercise for the purpose of estimating future glucose needs. Another exemplary physiological state is stress, and especially periodic acute stress, which can impact glucose levels (as compared to chronic stress which has long-term effects). Yet another exemplary physiological state is sleep, and the method can include determining a stage of sleep for the patient. Knowing the patient's state, such as during exercise, a stressful, moment, or while sleeping, is useful to provide a context and understanding for interpreting measured glucose and biometrics.

Embodiments of the method of this invention include automatically predicting and alarming the patient of a predicted future low blood glucose concentration and or automatically determining and suggesting responsive measures including carbohydrate consumption to present low blood glucose concentration. The method can also include automated detection of food consumption and/or a rapid glucose level increase without manual input by the patient.

The invention further includes a device for monitoring and/or treating patient glucose levels. The device includes or incorporates a continuous glucose monitor adapted to measure a glucose level of a patient and a physiological status monitoring system worn by the patient and adapted to measure at least one physiological variable of the patient. The device is desirably further in communication with an insulin pump. An automatic controller is in communication with the glucose monitor and the physiological status monitoring system. The controller includes a processor and the necessary recordable medium to store and execute a prediction module adapted to automatically predict a future glucose level using data measured by the glucose monitor system and the physiological monitoring system, and a physiological classification module adapted to automatically determine a physiological state of the patient from the measured at least one physiological variable. Desirably, each of the prediction module and the physiological classification module include, or are based upon, a recursively updated stable multivariate time-series model. The controller also desirably controls an insulin infusion from the insulin, pump as a function of predicted future glucose level.

In embodiments of this invention, the physiological classification module is adapted to detect and/or classify a physiological state selected from physical activity, stress, sleep, or combinations thereof. The physiological classification module can detect and classify a patient's physiological state as a junction of activity intensity and duration, body position, heart rate, respiration pattern, or a combination thereof.

Recent advances in wearable sensor technologies provide valuable biometric variables such as ECG information and respiration rate at high sampling rates in addition to accelerometer, galvanic skin response, temperature and heart rate data. These data and their specific patterns of change in response to various factors such as meals, physical activity, acute stress and sleep, enable automatic monitoring of the current biological/metabolic state of a patient with T1D, well before the effects of these factors influence GC values. Embodiments of the invention characterize the state of these factors in order to determine the most effective rates of insulin infusion to keep GC in the desired range. For example, when physical activity is detected, the nature of the physical activity (aerobic or resistance exercise or a blend), such as its intensity and duration, will also be determined in order to forecast if the patient will have hypo- hyper- or euglycemia as a result of this specific physical activity and the insulin doses will be adjusted accordingly. This proactive approach rather than the reactive approach based exclusively on GC measurements will improve GC control significantly. A critical component of this AP system is the ability to analyze many signals simultaneously, diagnose specific patterns and interpret the source causes of the potential changes in GC. For example, an increase in heart rate can be caused by exercise or acute stress, which affects insulin sensitivity in opposite ways. Correct diagnosis can only be made by determining the context of the change in heart rate through the collective interpretation of other variables such as accelerometer data and inspiration patterns.

The method and device of embodiments of this invention automatically monitor for and determine a faulty or missing measurement transmitted by the continuous glucose monitor or the physiological sensors. The device can include a fault detection and diagnosis module to monitor in real time sensors, the insulin, pump, and/or modules of the device for malfunctions, such as by using various sources of information and models, including the estimates of plasma glucose concentration and/or plasma insulin concentration.

Other objects and advantages will be apparent to those skilled in the art from the following detailed description taken m conjunction with the appended claims and drawings.

DETAILED DESCRIPTION OF THE INVENTION

The present invention provides a method and device for monitoring and/or treating glucose levels of a patient with diabetes. The method is desirably implemented by a device including one or more individual modules discussed herein for providing a fully automated, closed-loop artificial pancreas.

Figure 1:
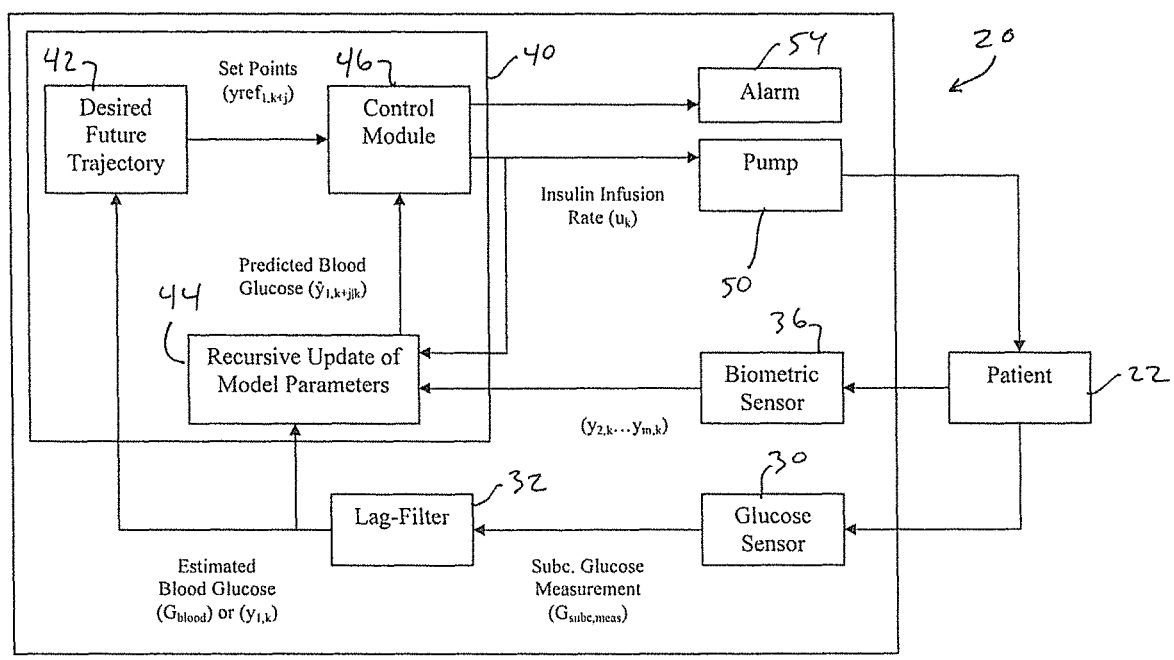
FIG. 1 is a block diagram of an automated closed-loop blood glucose monitoring/treating device according to one embodiment of this invention.

FIG. 1 illustrates components of device 20 for monitoring or treating glucose levels in a patient 22. The broader aspects of this invention are not intended to be limited to any particular implementation, and are thus shown schematically in FIG. 1. For example, the device 20 can be implemented as a single device including all components contained within a single housing, but is more practically implemented at this time through a combination of components where at least one component is separately housed and communicates with the one or more of the other components, such as wirelessly.

The device 20 includes a glucose sensor 30 for measuring a glucose level of the patient 22. The glucose sensor 30 desirably is embodied as a continuous blood glucose monitor (CGM) that determines blood glucose levels of interstitial fluids on a continuous basis, such as every few minutes. A typical CGM includes a disposable glucose sensor that is placed just under the skin, which is worn for a period of time until replacement, and a non-implanted electronic receiver component worn by the user. In one embodiment of this invention, the receiver components can be integrally combined with other components of this invention, such as are discussed below. The glucose sensor 30 desirably includes a transmitter and a power source that is rechargeable without a wired connection, and computational capabilities, such as a data processor and recordable medium (e.g., flash memory) 10 implement the necessary modeling algorithms of this invention.

Glucose levels in interstitial fluid temporally lag behind blood glucose values, generally understood to be about five minutes behind. This lag can create issues during times of rapidly changing glucose levels. In the embodiment illustrated in FIG. 1, the device 20 includes a measurement delay filter compensator 32 to address this glucose reading lag time. The filter compensator 32 takes the subcutaneous glucose measurement and determines an estimated blood glucose level. The filter compensator can be implemented within the glucose sensor 30, or within another component of device 20 depending on need.

The device 20 also includes a physiological status monitoring system 36 for measuring at least one physical or metabolic variable of the patient 22 with more than one physiological sensor worn by the patient. Examples of physical or metabolic variables that can be monitored by the physiological status monitoring system 36 include, without limitation, movement (e.g., incorporating an accelerometer), skin temperature, dissipated heat from the body, galvanic skin response, heart rate, ECG, respiration rate, posture, or body position. The system 36 includes a software, module on a recordable medium for deriving at least one physiological state selected from sleep, total energy expenditure, stress, physical activity, or combinations thereof.

The physiological status monitoring system 36 can be implemented according to need. In one embodiment of this invention, the physiological status monitoring system 36 is implemented as an armband monitoring system worn by the patient 22. The armband desirably wirelessly communicates with other components of the device, such as using wireless local area network technologies or other radio frequencies. One exemplary armband, monitor that can be used and/or modified for use in the device 20 is available from Bodymedia, Inc., and sold under the name Sense Wear. Other embodiments may include chestbands, wristbands and sensors that can be pasted on skin.

The device 20 further includes an automatic controller 40 in communication with the glucose sensor 30 and the physiological status monitoring system 36. The controller includes a prediction module 42 for automatically predicting a future glucose level using data measured by the glucose sensor and the physiological sensor. The controller 40 includes a processor in combination with a recordable medium for implementing the control model according to this invention. The recordable medium stores the data, measured by the glucose sensor and the physiological, sensor, and the prediction module 42 predicts the future blood glucose level using at least a portion of the stored measured information by the glucose sensor and the physiological sensor.

In one embodiment, the prediction module includes an algorithm for predicting/future glucose concentration values at or between 5 to 60 minutes into the future, and preferably 5-30 minutes with high accuracy. The prediction module desirably includes a recursive model for predicting the future glucose level using data measured by the glucose sensor and the physiological sensor. The controller 40 also desirably includes an update module 44 for continuously updating the parameters of the recursive modeling, based upon the measurements of the sensors and the amount of insulin prescribed in response to the future glucose prediction.

The controller 40 includes a control module 46 that acts upon the predicted blood glucose levels by implementing an insulin pump 50. The controller 40 provides an insulin infusion rate to the insulin pump 50 as a function of the predicted future glucose-level. The device 20 can also include an alarm 54 for alerting the patient of an unsafe current or future glucose level.

Any suitable insulin pump and alarm mechanism can be used in this invention. The insulin pump desirably includes an insulin reservoir that can be refilled without removing the entire pump device. As it can be desirable to limit the number of separate components, several of the components can be implemented in a single integrated device. In one embodiment of this invention, more than one, or all, of the glucose sensor, controller, pump, and alarm can be implemented in a single device housing. Integral components can communicate by wired connections, whereas separately housed components, such as any biometrics wearable sensor(s), can communicate wirelessly through known wireless technologies.

The glucose monitoring and/or treating device of this invention is preferably a closed-loop system that does not requiring manual user inputs for either predicting patient glucose levels or, desirably, for operating the insulin pump. In one embodiment of this invention, the device implements a method of predicting glucose levels in a patient. The device periodically measures a glucose level in the patient to obtain actual glucose measurements, which can be modified as needed to account for any lags due to the type of sensor mechanism. The device further monitors for physiological signals of the patient to obtain measured physiological signals or derived physiological variables. The device models a glucose concentration of the patient as a function of the actual glucose measurements and the physiological signals. Using the patient model the device estimates a future glucose level for the patient from the model of the glucose metabolism of the patient, and can provide insulin according to the estimation.

As discussed above, the patient model cart be updated in view of new information from, the patient measurements. In one embodiment of this invention, the device determines changes in glucose metabolism model parameters and modifies the glucose metabolism modeling in view of the new parameters. In one embodiment, such as where the modeling includes multivariate recursive time series modeling, the model is automatically recursively updated with each of the actual glucose measurements. A determined difference between the estimated future glucose level for a timeframe and an actual glucose measurement, for that timeframe can be a trigger and used for modifying the model of the glucose metabolism. The glucose metabolism model can be established and updated by analysis of the stored actual measurements for a timeframe and the corresponding physiological data sampled during that timeframe.

The invention incorporates one or more recursive multivariate dynamic models that describes glucose homeostasis in the patient body and provides hypoglycemia warning systems and closed-loop automatic adaptive controllers to regulate blood glucose levels by manipulating insulin infusion rates from an automatically controlled pump. Signals from the continuous glucose monitoring device and the multi-sensor body monitor (e.g., armband) are used for initial model development. The models developed are subject-specific (they can handle inter- and intra-subject variabilities of glucose metabolism) and desirably do not require any manual inputs from the subject (they function in fully automated form).

Figures 2, 3:
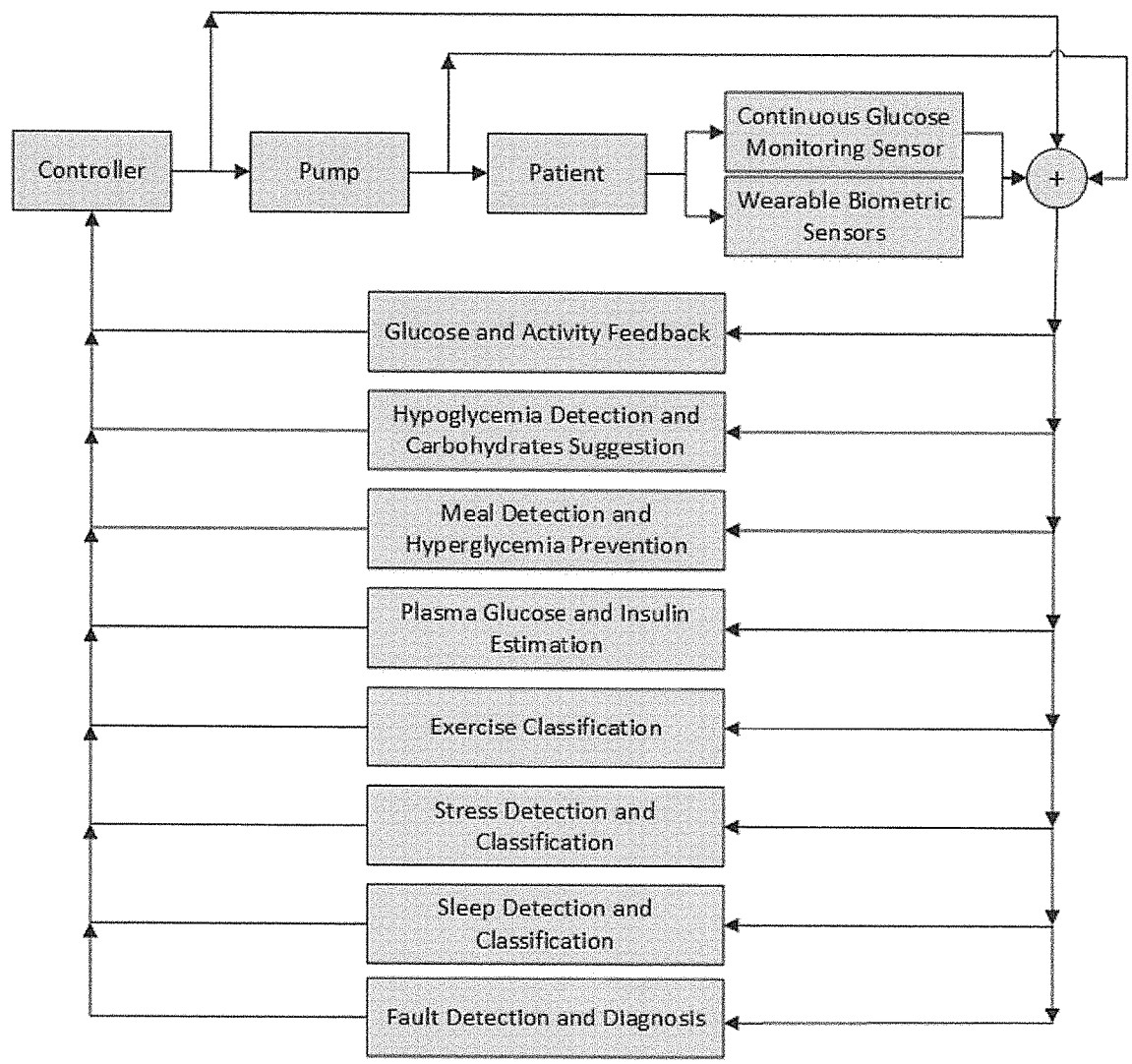
FIG. 2 is a block diagram of an automated closed-loop blood glucose monitoring/treating device according to one embodiment of this invention, FIG. 3 summarizes the effects of different types of exercise.

As shown in FIG. 2, embodiments of the invention further provide a modular artificial pancreas supervision and control system, such as implemented by the controller. In one embodiment, the system includes one or more modules for; (1) recursive model identification, (2) hypoglycemia early alert and alarm, (3) adaptive control, (4) hyperglycemia early alert and alarm, (5) plasma insulin concentration estimation, (6) assessment of physical activity (presence, type, duration, expected effects on insulin sensitivity and GC), (7) detection of acute stress and assessment of its impact on insulin sensitivity, (8) detection of sleep and its stages and assessment of the impact of sleep stages on GC, (9) sensor fault detection and diagnosis, (10) software and controller performance evaluation and adjustment, and or (11) pump fault detection and diagnosis.

Modules 1-3 are discussed in U.S. Pat. No. 8,690,820, herein incorporated by reference, and can be integrated with the master control system of this; invention. Module 4 can be implemented similar to Module such as using detection techniques for rapid increases in glucose. The modules will make use of the glucose sensor(s) and other physiological status sensor(s), as discussed herein, and have methods for change detection and interpretation, such as discussed herein.

In embodiments of this invention, the sensors and insulin pump can desirably communicate with a smartphone that can communicate with a server computer through wireless communication. At least several of the above modules can reside on the smartphone and will be executed there. Some modules with intensive computations, software for data storage and meta-super vision of the whole system, and communication software with care providers and emergency contacts can reside on the server.

In embodiments of this invention, the method includes: automatically monitoring a glucose concentration level in the patient with a continuous glucose monitor worn by the patient to obtain a measured glucose level, automatically monitoring physiological variables of the patient using at least one physiological sensor worn by the patient to obtain measured physiological variables. The measured physiological variables are automatically used for determining a physiological state of the patient, such as physical activity, stress, and/or sleep. The method further includes automatically estimating a future glucose level of the patient as a function of the measured glucose level, at least one of the measured physiological variables, and the determined physiological state of the patient. Embodiments of this invention further include automatically determining a change between at least two measured glucose levels that exceeds a predetermined value, and automatically comparing the change in the measured glucose level to any change in physiological state to determine a cause of the change in tire measured glucose level. For example, the determined response to a change in the glucose level will be different, if the person is determined to be sleeping or under stress or excreting. In one embodiment a physiological state of the patient can be determined b automatically matching the measured physiological variables to one of a plurality of predetermined classified physiological states. As an example, the invention can include automatically determining a stage of sleep for the patient.

Physical state has a wide range of effects on glucose concentrations in patients with type 1 diabetes depending on the type (e.g., aerobic, anaerobic, or mixed exercise) and the duration of the physical state. For example, the variability in glucose responses to physical activities makes the development of artificial pancreas (AP) systems challenging. To improve AP functioning, the invention further includes automatic detection of exercise intensity and its classification as aerobic or anaerobic, which is then used by the AP control algorithms. This can be achieved by using a multivariable AP approach where physiological (biometric) variables, such as described above, are measured and reported to the AP at high frequency. A classification system is provided that identifies, in real time, the exercise intensity and its reliance on aerobic or anaerobic metabolism. The classifier will be added as a new module to the integrated multivariable adaptive AP system to enable the detection of aerobic and anaerobic exercise for enhancing the accuracy of insulin infusion strategies during and after exercise.

Classification of Physical Activity

As discussed above, physical activity can significantly affect blood glucose concentration (BGC) in persons with type 1 diabetes (T1D). Regular physical activity has several positive contributions on management of diabetes, such as improving insulin sensitivity, controlling body mass and lipid profiles and boosting self-esteem. Most AP control systems seek to regulate BGC in persons with T1D by using information from a continuous glucose monitor with little or no regard to physical activity levels. Physical activity challenges the AP system as a disturbance that can lead to unsafe conditions such as hypoglycemia or hyperglycemia.

Compared to resting conditions, aerobic exercise increases glucose uptake anywhere from 1.5 to 10-fold, depending on the intensity of the activity. The dramatic increase in glucose needs of the working skeletal muscle is normally matched precisely by increased hepatic glucose production in nondiabetic individuals by a complex orchestration of feed forward and feedback mechanisms. In contrast, during intense aerobic exercise and during anaerobic work, hepatic glucose production can exceed muscle glucose utilization and glucose levels can rise dramatically. Thus, one of the key determinates of the glycemic response to exercise is the general classification of the exercise intensity (i.e., aerobic vs. anaerobic). The somewhat unpredictable effects on the BGC due to physical exercise cause fear in persons in T1D and this fear may be a barrier to exercise.

Exercise intensities that are dominantly reliant on by aerobic metabolism increase insulin sensitivity, which subsequently increases glucose uptake from the blood stream to tissue cells. This type of exercise is often of longer duration and with lower rates of muscular contractions compared to anaerobic exercise (see FIG. 3 for examples). When the aerobic exercise is prolonged or its intensity is increased. BGC can drop significantly, causing serious consequences in performance and eventually lack of coordination, dizziness, loss of consciousness and seizures if left untreated.

On the other hand, exercise that becomes more reliant, on anaerobic metabolism may increase BGC that could lead to hyperglycemia due to the release of catecholamines which increase glucose production and limit glucose uptake into muscle. Typically, anaerobic exercise is commonly characterized by high rates of muscular contractions for short durations and subsequent relatively long periods of recovery, which may contribute to the significant increases in BGC.

In embodiments of this invention, an automated discrimination method is used for exercise intensity identification and classification of the reliance of the exercise on aerobic or anaerobic metabolism in real time as new information to be used in the integrated, multivariable adaptive AP (IMA-AP) system. In one embodiment, the identification method is developed based on k-nearest neighbors (KNN) classification algorithm. The identified exercise intensity information can be exported to an AP, which enables the system to assess the potential impact of the exercise, forecast potential hypo or hyperglycemia, and provide preventive action to keep BGC in target range.

An experimental protocol was prepared with five participants (two males, three females). All participants were using insulin pump therapy and were classified as having a 'moderate-to-high' physical activity level based on a self-reported questionnaire. Participants were all in good to fair glycemic control (last $HbA_{1c}$<8.0%). Participants were all provided with an informed consent and the 2015 Physical Activity Readiness Questionnaire (2015 PAR-Q+ www.eparmed.com) to determine eligibility and risk stratify the study participants, which, would participate in a range of physical activity intensities from light-to-maximum, safely. Pre-exercise heart rate (HR) and blood pressure (BP) were measured using the BpTRU (Surge Surgical Supplies, Toronto, Ontario) automated blood pressure device to ensure participants were within an acceptable range prior to the initiation of the exercise protocols; BP<160/90 mmHg. The participants had their blood pressure and heart rate measured on the right and left arm while seated in a relaxed position, feet flat on the ground and legs uncrossed. Six measurements were taken consecutively with a 1-minute rest interval in between, and averaged. The average values were obtained and used in the analysis.

Participants reported on four separate occasions. The first visit consisted of a graded (progressive) treadmill test of maximal aerobic power ($VO_2$max), lasting from 10-12 minutes, while the next three visits involved 40-minute exercise sessions; two vigorous-to-maximum maximum intensity circuit based protocols and one continuous, light-to-moderate intensity steady state aerobic protocol. A further description of the visits and the types of exercise performed are found below. All four visits were completed with a minimum of 24-hours between sessions in order to reduce the likelihood of blood glucose dysregulation due to exercise. All visits were conducted at the same time within each subject (either 11:00 AM or 4:00 PM), Baseline whole blood glucose concentrations were measured 10 minutes prior to the start of exercise (T minus 10 min) and every 10-minutes during exercise and in recovery (10-, 20- and 60-minutes post exercise) using a Contour® Next Link or Contour® glucometer (Bayer Inc., Mississauga, ON). Lactate measurements were completed every 10-minutes using a Lactate Scout+Analyzer (EKF Diagnostics, Germany). The rate of perceived exertion (RPE) was also measured throughout the exercise using the Borg Scale. Participants were asked to take their usual bolus of insulin with breakfast (7:00 AM) or lunch (12:00 PM) in order to begin the exercise protocol with minimal active or "on-board" bolus insulin. Exercise was immediately terminated if blood glucose concentrations were <3.5 mmol•$L^{-1}$ at any point during exercise. If necessary, participants were provided with a respective dose of dextrose to treat hypoglycemia (Dex4®, AMG Medical Inc.).

Anthropometric measurements were conducted on all participants during visit 1, including height (cm), body mass (k), body fat percentage, sum of five skinfolds, and waist circumference (WC) (cm). Standardized protocols were used to measure height, weight and WC. Height was measured without shoes using a stadiometer (Fitness Precision, Toronto Ontario). Body mass was measured using a digital scale (Seca Alpha, Germany) with no shoes and light clothing. WC was measured using the National Institute of Health (NIH) protocol; the measuring tape was placed on the skin at the level of the iliac crest. Body fat percentage was determined through bioelectrical impedance analysis instrument (Tanita Scale, model TBF-612, Arlington Heights, Ill.), Skinfold measurements were taken using Harpenden fat calipers at standard sites: bicep, tricep, subscapula, iliac crest and medial calf, as per the Physical Activity & Lifestyle "R" Medicine (PALM): A Health-Related Physical Activity and Lifestyle Approach.

Participants wore a physiological monitoring module (Bioharness-3, Zephyr Technology, Annapolis Md.) to monitor various physiological variables including heart rate (HR), breathing rate, posture, activity level, peak acceleration, speed, and distance moved. Participants also wore a Polar chest HR monitor to obtain exercise and maximum HR (Polar Electro, Kemple, Finland). Participants were fitted with a Fitmate Pro Metabolic Unit (COSMED, Italy, Image Monitoring Mississauga, Ontario) for the determination of $VO_2$ during the continuous light-to-moderate intensity (L-MI) plus vigorous-to-maximum intensity (V-MI) circuit exercise sessions and during the determination of VO$_2$. An incremental-to-maximum effort treadmill protocol was used to determine VO$_2$max and peak or maximum exercise HR. During the incremental to maximal test the protocol consisted of 2-minute work stages that increased in intensity (treadmill speed and/or elevation) at every stage. The participants were instructed to remain on the treadmill until they reached volitional fatigue at which point they received a 2-minute low-intensity active recovery. Following the recovery period, the participants continued the test for another stage, and then were given another 2-minute recovery alter completing the workload. This discontinuous portion of the graded exercise test was used to ensure the attainment of VO$_2$max. The attainment of VO$_2$max was determined by applying the following criteria; a plateau in VO$_2$ with increasing workloads where VO$_2$ does not increase more than 1.5 mL of O$_2$•kg$^{-1}$-min$^{-1}$ or 150 mL•min$^{-1}$, respirator exchange-ratio (RER) value greater than 1.15, and no increase in HR with an increase in workload. Participants were fitted with a continuous glucose monitor (CGM) Enlite™ sensor (Medtronic Ltd., Minneapolis, Minn.) that was inserted into the interstitial space under the skin on the abdomen or upper buttocks. Participants were also instructed to use the laboratory issued glucometer for every self-monitoring of blood glucose (SMBG).

Basal rate reductions were customized per subject for the V-MI exercise sessions. Participants began by walking on a treadmill at 3.5 MPH and 2% incline for 4-minutes followed by the circuit. The circuit begun with 45-seconds of marching on the spot with high knees and swinging the arms with 5-8 lb. dumbbells in each hand (5 lb. for females, 8 lb. for males). Next, participants were asked to complete a squat with a front sweep and 4 kg medicine ball swinging between the legs and over the head for 60-seconds. Four jumping jacks followed by a quadruped motion (palms flat on the floor, extending one arm and opposite leg simultaneously) for 30-seconds and then two jumping jacks, four push-ups, and a 20-second forearm plank. The next exercise was marching on the spot with high knees for 30-seconds, followed by squats with an 8 kg medicine ball placed on a high shelf each time for 60-seconds. The circuit finished with four push-ups and a 20-second forearm plank. Participants were then asked to cycle on a cycle ergometer (Monark 874 E, Sweden) for 4-minutes at 60 RPM with 2.5 kg of resistance and then completed the circuit two more times. In between the second and last circuit, participants walked on the treadmill again for 4-minutes at 3.5 MPH and 2% incline. Participants completed the IHE protocol by cycling at 60-70 RPM for 10 minutes until 40-minutes of exercise were reached.

During one of the two circuit exercise sessions, basal rate adjustments were made every 10 minutes for all participants with T1D. The basal adjustment patients varied between some participants; however, the total percentage reduction was always the same during the 40-minute exercise session (Table 1). Basal rates were at 100% for all participants 10-minutes prior to exercise until the onset of exercise. Once the circuit exercise began, basal rates were adjusted in a random pattern. 1 able 1 summarizes the percent of basal rate (%) adjustment for each participant (1-5) with T1D from 10-minutes prior to exercise to 40-minutes of the circuit exercise session. Basal rates were adjusted every 10-minutes in different patterns for all participants. The total combined percent reduction was the same between participants.

TABLE I

| Time of exercise | Subject 1 | Subject 2 | Subject 3 | Subject 4 | Subject 5 |
|---|---|---|---|---|---|
| −10 (Pre) | 100 | 100 | 100 | 100 | 100 |
| 0 | 30 | 40 | 50 | 30 | 40 |
| 10 | 50 | 20 | 30 | 50 | 20 |
| 20 | 20 | 50 | 40 | 20 | 50 |
| 30 | 40 | 30 | 20 | 40 | 30 |
| 40 | 100 | 100 | 100 | 100 | 100 |

One visit involved continuous, steady state L-MI aerobic exercise where basal insulin was set to zero for the entire exercise protocol, and resumed to 100% immediately following the cessation of exercise. During the treadmill protocol, participants were fitted with the same measurement equipment as the V-MI protocol. Participants exercised at 3.5 MPH and 2% incline for 40-minutes.

The identification of the intensity of exercise and its reliance on aerobic or anaerobic metabolism is made by KNN classification algorithm. KNN classification is one of the most popular classification methods used when there is little or no prior knowledge about the distribution of the data. In contrast to most concept learning systems, KNN classification docs not formulate a generalized conceptual model from the training instances at the training stage. Rather, a simple and intuitive rule is used to make decisions at the classification stage; instances close in the input space are likely to belong to the same class. An object is classified by a majority vote of its neighbors, with the object being assigned to the class most common among its k-nearest neighbors.

Defining x and y as the matrix of input features and vector of output labels of a training dataset, the standardized Euclidean distance vector $D_{x,x_{new}}$, between a new observation vector $x_{new}$ and training data matrix x is defined as:

$$D_{x,x_{new}}(t) = \sqrt{\sum_{j=1}^{m} \left( \frac{x_j(t) - x_{new,j}}{W_j} \right)^2} \quad (1)$$

where t=1, ..., N and N is the number of training data. $W_j$ is the standard deviation of $j^{th}$ column of x matrix for N observations. The KNN algorithm is:
1. Compute the distance $D_{x,x_{new}}(t)$ for every training data t=1, ..., N.
2. Select k lowest distance and corresponding y(t).
3. Select $y_{new}$ as the most frequent class from the previous step.

If there are outliers in training data, the KNN algorithm may have some wrong classification just like all other data-based classification algorithms. Condensed nearest neighbors (CNN) rule was proposed to decrease the size of training data to a minimum such that the reduced size data is still able to describe all training data. The CNN algorithm is:
1. The first sample x(1) and y(1) is placed in $x_{store}$ and $y_{store}$, respectively.
2. The second sample x(2) is classified by the KNN algorithm using $x_{store}$ and $y_{store}$
   a. If x(2) is classified correctly, x(2) and y(2) are placed in $x_{discard}$ and $y_{discard}$, respectively.
   b. If x(2) is not classified correctly, x(2) and y(2) are placed in $x_{store}$ and $y_{store}$, respectively.
3. Repeat step-2 for all N (t=1, ..., N) observation in training data.

4. Use $x_{discard}$ and $y_{discard}$ and repeat step 2 and step 3 until:
   a. All elements $x_{discard}$ and $y_{discard}$ are transferred to $x_{store}$ and $y_{store}$, or
   b. No elements $x_{discard}$ and $y_{discard}$ are transferred to $x_{store}$ and $y_{store}$ during a complete loop (step-2 and step-3).
5. The final contents of the $x_{store}$ and $y_{store}$ are used as optimized training data for the KNN to be used in real-tune classification.

Data from 8 subjects were tested (5 with T1D, 3 without T1D). Demographic information of subjects is listed in Table III. The three volunteers without T1D wore the Bioharness-3 chestband while they were performing the above exercise protocol. The HR, BR, and PA signals from the Bioharness-3 chestband were defined to be features of the x matrix (statistical information is shown in Table II).

The y vector was defined to have binary values such that 0 and 1 are used for aerobic and anaerobic exercise, respectively. One second sampling time was used.

TABLE II

| Minimum-Maximum | | | Mean (Standard Deviation) | | |
|---|---|---|---|---|---|
| HR | BR | PA | HR | BR | PA |
| 73-188 | 12-39 | 0.02-1.09 | 164 (24) | 25 (6) | 0.49 (0.20) |
| 116-166 | 10-48 | 0.13-1.02 | 151 (13) | 33 (7) | 0.53 (0.23) |
| 62-183 | 11-45 | 0.03-0.98 | 135 (32) | 31 (8) | 0.50 (0.21) |
| 72-177 | 15-41 | 0.05-0.83 | 142 (23) | 29 (6) | 0.51 (0.16) |
| 106-191 | 15-36 | 0.13-1.16 | 152 (18) | 28 (5) | 0.46 (0.21) |
| 61-185 | 10-46 | 0.11-4.04 | 142 (30) | 29 (8) | 1.14 (0.84) |
| 76-154 | 10-68 | 0.04-3.97 | 110 (19) | 28 (11) | 0.8 (0.74) |
| 72-180 | 10-41 | 0.14-2.05 | 119 (24) | 27 (6) | 0.76 (0.40) |

TABLE III

| Sex | Age | Height (cm) | Body Mass (kg) | Body Fat (%) | VO2max (ml · kg · min$^{-1}$) | HbA1c (%) | Ave. daily insulin per day (units) | Dominant Hand | NIH Waist Cir. (cm) |
|---|---|---|---|---|---|---|---|---|---|
| M | 34 | 174 | 80.5 | 22 | 49.9 | 7.9 | 43.7 | Right | 83 |
| F | 33 | 182 | 78 | 27.9 | 37.9 | 7.7 | 40.5 | Right | 86 |
| F | 26 | 167 | 66 | 28.4 | 51.7 | 6.8 | 31.0 | Right | 81 |
| F | 25 | 167 | 70 | 29.4 | 41.6 | 7.1 | 36.0 | Left | 82 |
| M | 47 | 184 | 75.1 | 16.6 | 47.7 | 7.4 | 27.5 | Right | 84 |
| F* | 20 | 170 | 76 | 26.3 | N/A | N/A | N/A | Right | 74 |
| F* | 23 | 154 | 65.9 | 27.8 | N/A | N/A | N/A | Right | 69 |
| F* | 21 | 177.8 | 66.9 | 21.2 | N/A | N/A | N/A | Right | 66 |

(*indicate participants without T1D)

For each subject 75% of data were randomly selected to be training data, and the rest of data is used as testing data. The CNN algorithm was performed for each training data to remove outliers and reduce the size of the training data. The k was selected to 1 in the KNN algorithm for real time exercise identification.

Figure 4:
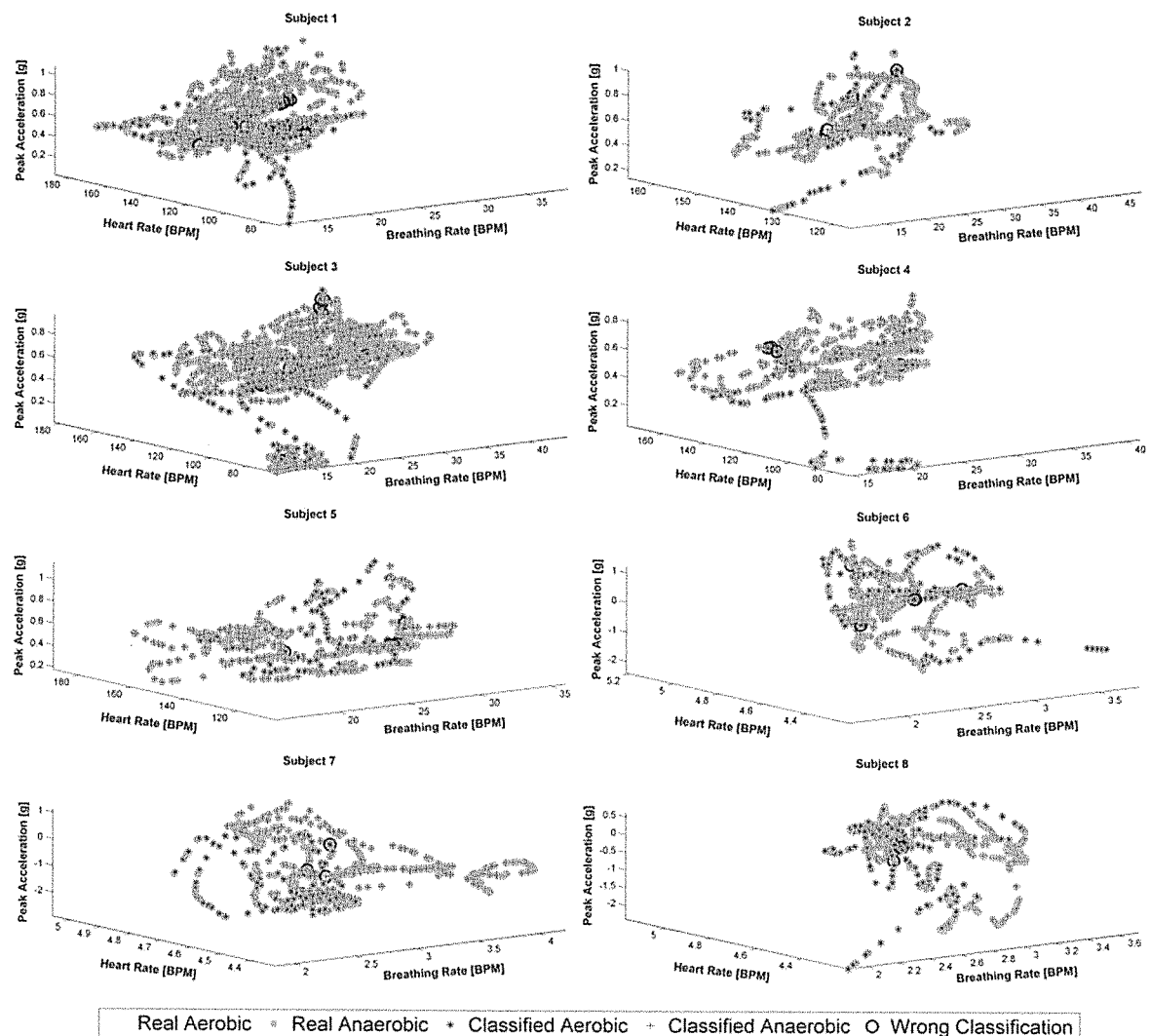
FIG. 4 illustrates identification of exercise type in real time.

FIG. 4 shows the real time exercise identification results for all 8 subjects. The algorithm is able to identify each exercise session correctly except some switching points between the two sessions (aerobic vs. anaerobic).

Table IV shows the performance analysis of the proposed algorithm. Overall 28324 seconds (aerobic: 14982 vs anaerobic: 13342) of exercise session were performed. The overall training data size was decreased from 17943 seconds to 1278 seconds after performing the CNN algorithm. Out of 7081 testing samples, 6997 seconds were truly classified (98.8%) with the KNN algorithm. The algorithm was not able to classify 1.2% of the testing data due to complexity in data at the time switching between aerobic and anaerobic.

TABLE IV

| | | Subject 1 | Subject 2 | Subject 3 | Subject 4 | Subject 5 | Subject 6 | Subject 7 | Subject 8 |
|---|---|---|---|---|---|---|---|---|---|
| Duration of (seconds) | Experiment | 4800 | 2400 | 7199 | 4800 | 2400 | 2453 | 2160 | 2112 |
| | Aerobic session | 2100 | 960 | 4319 | 3360 | 960 | 1376 | 815 | 1092 |
| | Anaerobic session | 2700 | 1440 | 2880 | 1440 | 1440 | 1077 | 1345 | 1020 |
| | Raw training data | 3600 | 1800 | 5399 | 3600 | 1800 | 1840 | 1620 | 1584 |
| | Testing data | 1200 | 600 | 1800 | 1200 | 600 | 613 | 540 | 528 |
| | Optimized training data | 294 | 138 | 305 | 105 | 99 | 176 | 76 | 85 |
| | True classification | 1174 | 591 | 1784 | 1191 | 593 | 606 | 535 | 523 |

TABLE IV-continued

|  | Subject 1 | Subject 2 | Subject 3 | Subject 4 | Subject 5 | Subject 6 | Subject 7 | Subject 8 |
|---|---|---|---|---|---|---|---|---|
| Wrong classification | 26 | 9 | 16 | 9 | 7 | 7 | 5 | 5 |
| Sensitivity (%) | 97.8 | 98.5 | 99.1 | 99.3 | 98.8 | 98.9 | 99.1 | 99.1 |

Exercise sessions are one of the most challenging periods for an AP system to regulate BGC. People with T1D have adopted a range of precautions such as modifying their insulin intake or changing their food consumption before and during an exercise. For a fully automated AP system no information should be manually entered or manual interventions be made. The proposed algorithm is developed as a new module for the IMA-AP system in order to enable the IMA-AP system to distinguish between predominant aerobic and anaerobic exercise metabolism, since these two distinct forms of exercise can have divert effects on glucose concentrations.

The results show that the algorithm is able to distinguish aerobic and anaerobic exercise with high level of accuracy accuracy. With only 159 (±91) seconds of a carefully selected training data, the KNN algorithm is able develop a classifier to identify aerobic and anaerobic exercise, based on heart rate, breathing rate and peak acceleration information from the Bioharness-3 chestband. The classifier was able to track very accurately the switching between aerobic and aerobic exercise during an exercise session for both groups of study participants as they alternate between sustained aerobic and circuit exercises.

The activity classification algorithm of this invention is able to differentiate and classify exercise intensities and the reliance of an exercise on aerobic or anaerobic metabolism with high accuracy. Use of biometric information and classification of exercise intensity and type in real time can provide valuable information where automatically integrated within an artificial pancreas for prevention of exercise-induced hypoglycemia and hyperglycemia.

Detection of Acute Stress and Sleep Patterns

Figure 5:
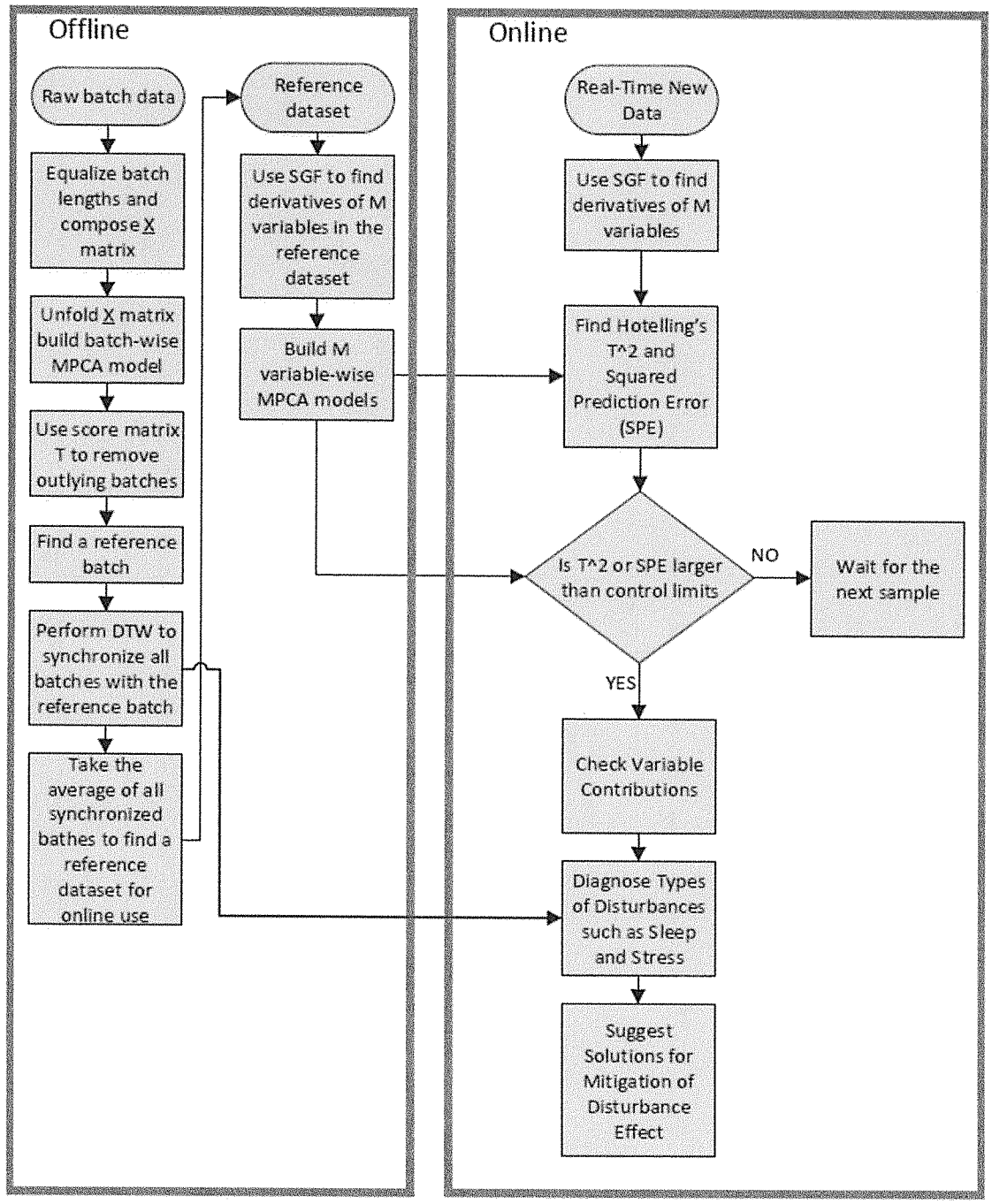
FIG. 5 is a flow diagram according to one embodiment of this invention.

The methods discussed above for discriminating the types of exercise and detecting and diagnosing faults by multivariate statistical techniques such as principal components analysis, clustering, classification and discrimination, machine Seaming techniques, dynamic time warping also provide the foundation for detecting acute stress and sleep stages and patterns. The techniques of embodiments of this invention rely on the interpretation, of the collective behavior of various biometric variables. In one embodiment, respiration patterns, heart rate patterns, specific signatures of body movements and body position can be collected from wearable biometric sensors as streaming data to detect sleep stages and patterns, in another embodiment, the same variables can provide different combinations of patterns to indicate acute stress. Hence the modules of the multi variable AP system are able to use the same set of variables to determine physical activity, acute stress and sleep by using the developed methods discussed above. FIG. 5 provides a flow chart for the development of assessment tools (offline) and real-time detection and diagnosis tools (online).

In embodiments of this invention, an important element of these tools is synchronization of data for developing the baseline and for comparison of new data from current state of the patient with the baseline. Measured signals are synchronized such that similar trends or events are overlapped. Also the sequences with various different lengths are optimally shortened or extended in order to have same length of datasets over all subjects. A better statistical comparison can be done once data are synchronized, in embodiments of this invention, the method integrates dynamic time warning (DTW), Saviztky-Golay filter (SGF) and principal component analysis (PCA). DTW is extended to its higher derivative orders where the derivatives are obtained through an optimally designed SGF. PCA is used for determination of statistical weigh matrices for the case of multivariable synchronization.

DTW has its origins in speech recognition and is a flexible, deterministic, pattern matching scheme that works with pairs of patterns. It can locally translate, compress, and expand the patterns so that similar features in the patterns are matched, DTW nonlinearly warps two trajectories in such a way that similar events are aligned and a minimum distance between them is obtained. It is assumed that an appropriate scaling is performed prior to implementation of DTW; scaling is an important issue since DTW is a distance-based technique.

Assume that $x_R$ and $x_T$ are the reference batch trajectory (previously defined) and a batch to be synchronized with data lengths R and T, respectively. DTW defines the Euclidean distance between each point of the two trajectories as:

$$d(i(\kappa),j(\kappa))=[x_R(i(\kappa))-x_T(j(\kappa))]^2 \qquad (2)$$

where κ is the number of grid points along a path between two trajectories. i, j are the sample points and goes up to R and T for the reference and new batch trajectories, respectively. The total distance between two batch trajectories is:

$$D(R,T) = \sum_{\kappa=1}^{L} d(i(\kappa), j(\kappa)) \qquad (3)$$

where max(R, T)≤L≤R+T. The optimal path and minimum total distance is found as the solution of the following optimization problem:

$$D^*(R,T) = \min_{F} D(R,T) \text{ or } F^* = \min_{F} D(R,T) \qquad (4)$$

The computational load to solve the problem in Eq. (4) might be high since all possible paths must be defined and the one which gives minimum distance is selected. An elegant and effective solution to this problem is dynamic programming which guarantees to find the optimum path without basing to calculate the distance along all possible path:

$$D_F(i, j) = d(i, j) + \min \begin{cases} D_F(i-1, j) \\ D_F(i-1, j-1) \\ D_F(i, j-1) \end{cases} \quad (5)$$

with respect to some local and global constraints:

$D_F(R,T) = d(R,T)$ $D_F(1,1) = d(1,1)$ $i(k+1) \geq i(k)$ $j(k+1) \geq j(k)$ (6)

When a feature (peak, valley, etc.) is slightly higher (or lower) from one trajectory to another, DTW may suggest aligning one single point on $x_R$ to a large number of points on $x_T$ or the opposite. To overcome this singularity problem, the point first order derivative (d1) can be used instead of Euclidian distance to measure the difference between two trajectories:

$$d^1(i(\kappa), j(\kappa)) = [x_R^1(i(\kappa)) - x_T^1(j(\kappa))]^2 \quad (7)$$

where $$x_R^1(i) = \frac{x_R(i) - x_R(i-1)}{2} \quad (8)$$

In mathematics, an object associated with a function that responds to its variability in time is the derivative of the function, the derivative of the function determines areas where the function is constant, increases or decreases, and the intensity of the changes, the derivative determines the general shape of the function rather than the value of the function at a specific point and shows what happens in the neighborhood of the point. In the case of time series, this means that the derivative of the function considers the behavior of a time series before and after some point in time. While the first derivative of a function gives some information about the shape of the function (increasing or decreasing), the second derivative adds additional information as to where the function is convex or concave.

Many datasets from real life applications usually do not follow a Normal distribution. Suppose that Z is a real-valued random variable measured from a real-life application. The mean of Z is a measure of the center of the distribution of Z. Furthermore, the variance of Z is the second moment (derivative) of Z about the mean, and measures the spread of the distribution of Z about the mean. The third and fourth moments of Z about the mean also measure interesting features of the distribution. The third moment measures skewness, the lack of symmetry or the degree of asymmetry of a distribution around its mean, while the fourth moment measures kurtosis, the degree to which the distribution is peaked or the relative peakedness or flatness of a distribution compared with the normal distribution.

A high order DDTW (HODDTW) can be used to capture more statistical information from a distribution as mentioned above. The distance for the HODDTW is defined as:

$$d(i(k), j(k)) = \sum_{z=0}^{4} \alpha_z d^z(i(k), j(k)) \quad (9)$$

where $d^z$ is the Euclidean distance between each point of the $z^{th}$ derivatives of two trajectories, $a_z$'s are the coefficients to give different weights to different derivative orders and are defined as:

$$\alpha_z = \frac{e^{-x}}{\sum_{x_j=0}^{s} e^{-x}j} \text{ for } z = 0, \ldots, 4 \quad (10)$$

Note that, the DDTW algorithm may not be as robust as DTW due to the numerical, derivative estimation in Eq. (9) when it is applied to noisy trajectories. The SGF can be used to obtain the first derivative estimations. The SGF is a filter for smoothing without greatly distorting the signal by calculation of convolution coefficients, by fitting successive subsets of adjacent data points with a low-degree polynomial by the method of linear least squares. When the data points are equally spaced an analytical solution to the least-squares equations can be found, in the form of a single set of convolution coefficients that can be applied to all data subsets, to give estimates of the smoothed signal, (or derivatives of the smoothed signal) at the central point of each subset. A major drawback of the convolution weights for the center-point least-squares evaluation of 2m+1 points is that the first and end points of the data sets are lost (2m points for a 2m+1 point filter). A technique based on Gram polynomials can be used for calculation of SGF convolution coefficients at all positions, for all polynomial orders, all filter lengths, and any derivative without any loss of initial or end points.

Considering the uniformly sampled signal yl, we want to smooth and estimate its sth order derivative using a 2m+1 point filter and a polynomial of order n. The least squares polynomial has the form:

$$f_n(l) = \sum_{k=0}^{n} b_k l^k \quad (11)$$

where $l = -m, \ldots, +m$. The least squares criterion requires that the sum of the squares of the differences between the observed values, yl and the calculated, $f_n(l)$ be a minimum over the interval being considered:

$$\frac{\partial}{\partial b_k} \left[ \sum_{l=-m}^{m} (f_n(l) - y_l)^2 \right] = 0 \quad (12)$$

This leads to n+1 simultaneous equations with, respect to the unknown coefficients bk at l=0 for smoothing (s=0) or differentiation (s≥1).

The least squares approximation of a function can also be obtained with a weighted expansion of discrete orthogonal polynomials, rather than, a simple powers series that is used in Eq. (11). Gram polynomials are well suited for this problem and Eq. (11) can be rewritten as:

$$f_n(t) = \sum_{k=0}^{n} b_k P_k^m(t) \quad (13)$$

where $P_k^m(t)$ is the Gram polynomial with order k, over 2m+1 points, evaluated at point t and is defined as:

$$P_m^k(t) = \sum_{r=0}^{k} \frac{(-1)^{r+k}(r+k)^{(2j)}(m+t)^{(r)}}{(r!)^2(2m)^{(r)}} \quad (14)$$

where $(A)^{(B)}$ is a generalized factorial function: $(A)(A-1)\ldots(A-B+1)$ and $(A)^{(O)}=1$. After substituting Eq. (14) into Eq. (13) the generalized form for the convolution coefficients for data point i ($-m \le i \le m$) with polynomial order n and $s^{th}$ derivative, evaluated at position t is:

$$f_0^n(t) = \frac{h_i^{t,s} y_i}{\Delta \theta^s} \quad (15)$$

$$h_i^{t,s} = \sum_{k=0}^{n} \frac{(2k+1)(2m)^{(k)}}{(2m+k+1)^{(k+1)}} P_k^m(l) P_k^{n,s}(t) \quad (16)$$

$$P_k^{n,s}(l) = \frac{2(2k-1)}{k(2m-k+1)}[l P_{k-1}^m(l) + s P_{k-1}^{n,s-1}(l)] - \frac{(k-1)(2m+k)}{l(2m-k+1)} P_{k-2}^{n,s} \quad (17)$$

with $P_0^{m,s}(l)=0$ and $P_1^{m,s}(l)=0$. Note that, in case of differential ($s \ge 1$), the original data points are separated by $\Delta \theta$ in Eq. (15) rather than $\Delta \theta^s=1$ for $s=0$. Eq. (17) is the recursive version of the Eq. (14) which is more practical for computations.

PCA can be used to assign different weights to different variables according to their statistical importance. PCA involves the orthogonal decomposition of the set of process measurements along the directions that explain the maximum variation in the data, for a continuous process, the data can be represented by matrix $X_{n \times m}$ where n is the number of observation and m the number of variables. The directions extracted by the orthogonal decomposition of X are the eigenvectors $p_i$ of $X^T X$ also called principal components (PC) Loadings:

$$X = t_1 p_1^T + t_2 p_2^T + \ldots + t_a p_a^T + E \quad (18)$$

where E is the residuals matrix and superscript T denotes matrix transpose. The dimension $\alpha$ is chosen such that most of the significant process information is captured by the $t_i p_i^T$ terms, and E contains mostly random error. The projection of the measurements onto the eigenvectors defines new points in the measurement space that constitute the score matrix $\tilde{T}$ whose columns are $t_i$ (Eq. (18)). The relationship between $\tilde{T}$, $\tilde{P}$, and X can also be expressed as:

$$X = \tilde{T}\tilde{P}^T + E \quad E = X - \tilde{X} \quad (19)$$

where $\tilde{X}=\tilde{T}\tilde{P}^T$ and $\tilde{P}$ is the m+$\alpha$ matrix of loadings and $\tilde{T}$ is the n×$\alpha$ score matrix. PCA transforms the coordinate system of a data set for more efficient description of variability in data. The PCs can be computed by singular value decomposition (SVD) of the data matrix X:

$$X = USV^T \quad (20)$$

where the columns of U are the normalised eigenvectors of $XX^T$, the columns of V are the normalized eigenvectors of $X^T X$, and S is a diagonal matrix having as its elements the singular values. The loadings and score matrices can be expressed as:

$$\tilde{P} = V_{m \times \alpha} \text{ and } \tilde{T} = U_{n \times \alpha} S_{\alpha \times \alpha} \quad (21)$$

The multivariable version of the Eq. (2) is defined as:

$$d(i(\kappa), j(\kappa)) = [\tilde{T}_R(i(\kappa)) - \tilde{T}_T(i(\kappa))] A [\tilde{T}_R(i(\kappa)) - \tilde{T}_T(i(\kappa))]^T \quad (22)$$

where A is a diagonal weight matrix defined as:

$$\Lambda_{\tau,\tau} = \frac{S_{R,\tau,\tau}^2}{\sum_{\tau=1}^{\alpha} 2 S_{R,\tau,\tau}^2} + \frac{S_{T,\tau,\tau}^2}{\sum_{\tau=1}^{\alpha} 2 S_{T,\tau,\tau}^2} \quad (23)$$

The Eq. (22) is used in the Eq. (9) where the original multivariate signals $X_R$ and $X_T$ are changed with their score matrices $\tilde{T}_R$ and $\tilde{T}_T$, respectively. In the Eq. (22), more weight is given to the score vectors that are aligned with the directions of maximum data variance.

To demonstrate this method of the invention, experiments were conducted over a 3-day period. Subjects were provided a CGM device, a BodyMedia SenseWear armband, and a Zephyr chestband. Continuous data collection from 10 subjects (6 male, 4 female, 19-27 years) with T1D (average A1C 7.7%) started on Day 1 and insulin delivery via AP algorithm continued for 60 hours. Data were collected and transmitted to a laptop computer, every 5 minutes. Day 1 subjects ate breakfast, then had an aerobic exercise (60-80% heart rate reserve (HHR) used from their VO2Max), ate then had an anaerobic/resistance (AR) exercise (2-3 sets of 8-12 reps. 60-80% rep 1 max). Day 2 they ate breakfast then had AR exercise, ate then had an interval exercise (30-40 min; 5 min warm up, 3 min at 60-70% HRR of VO2MAX, 4 minutes at 85-90% HHR of VO2MAX x4, with 5 min cool down). On day 3 the order of exercise types was identical in day 1. Variations in meal and exercise times and intensities between subjects and from day to day provided a dataset that can illustrate the effects of trajectory synchronization.

Figure 6:
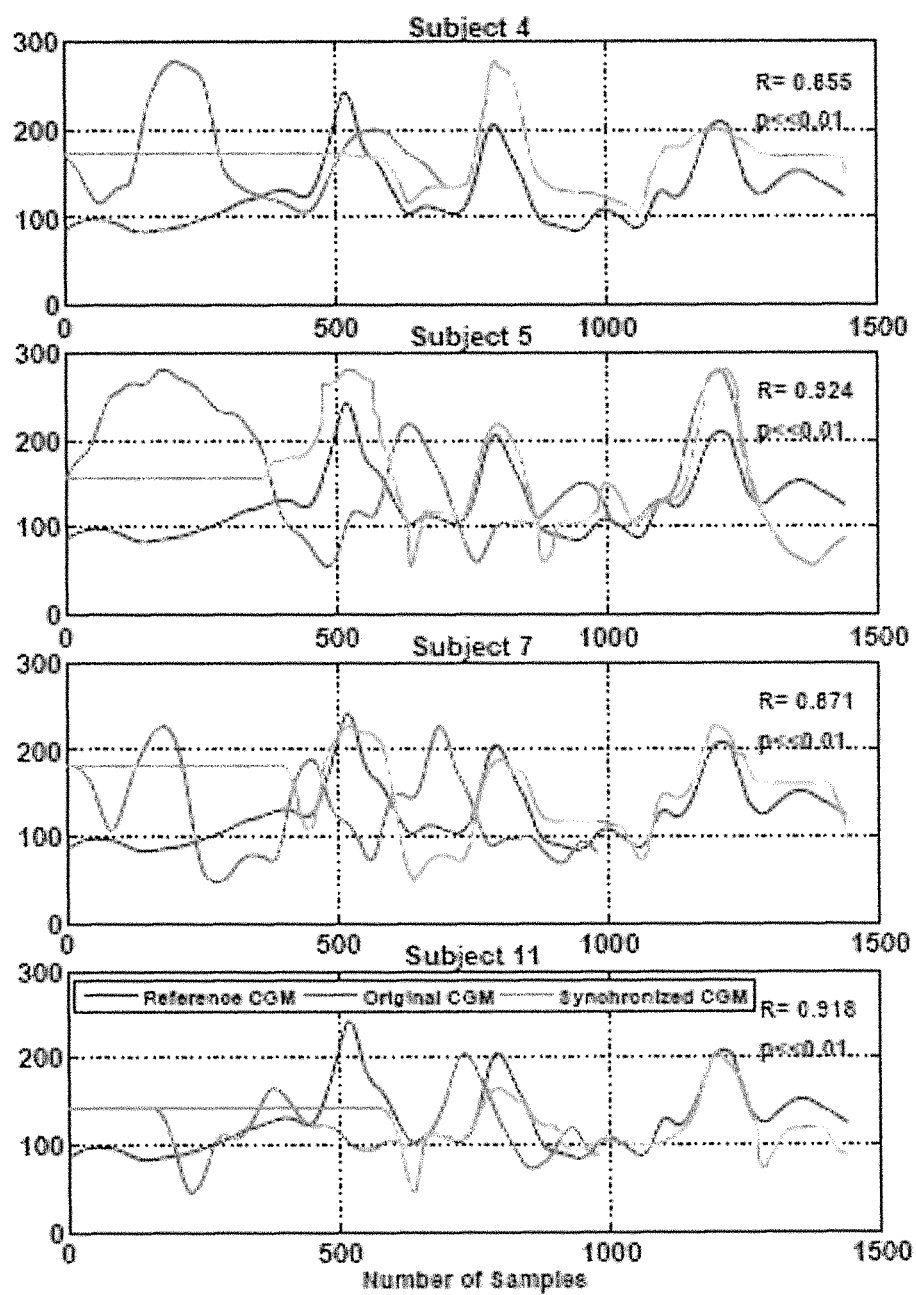
FIGS. 6-10 include graphs produced during testing of examples of the invention.

Glucose measurements from the second day of subject 3 was used as the reference trajectory for the performance evaluation of the single variable version of the proposed algorithm. FIG. 6 shows synchronized CGM signal from four subjects collected on days 1. As shown in the figure, according to Pearson's correlation the synchronized signals are significantly ($p \ll 0:01$) correlated with the reference trajectory. The length of the original signals are now equal to the reference trajectory after synchronization.

Figure 7:
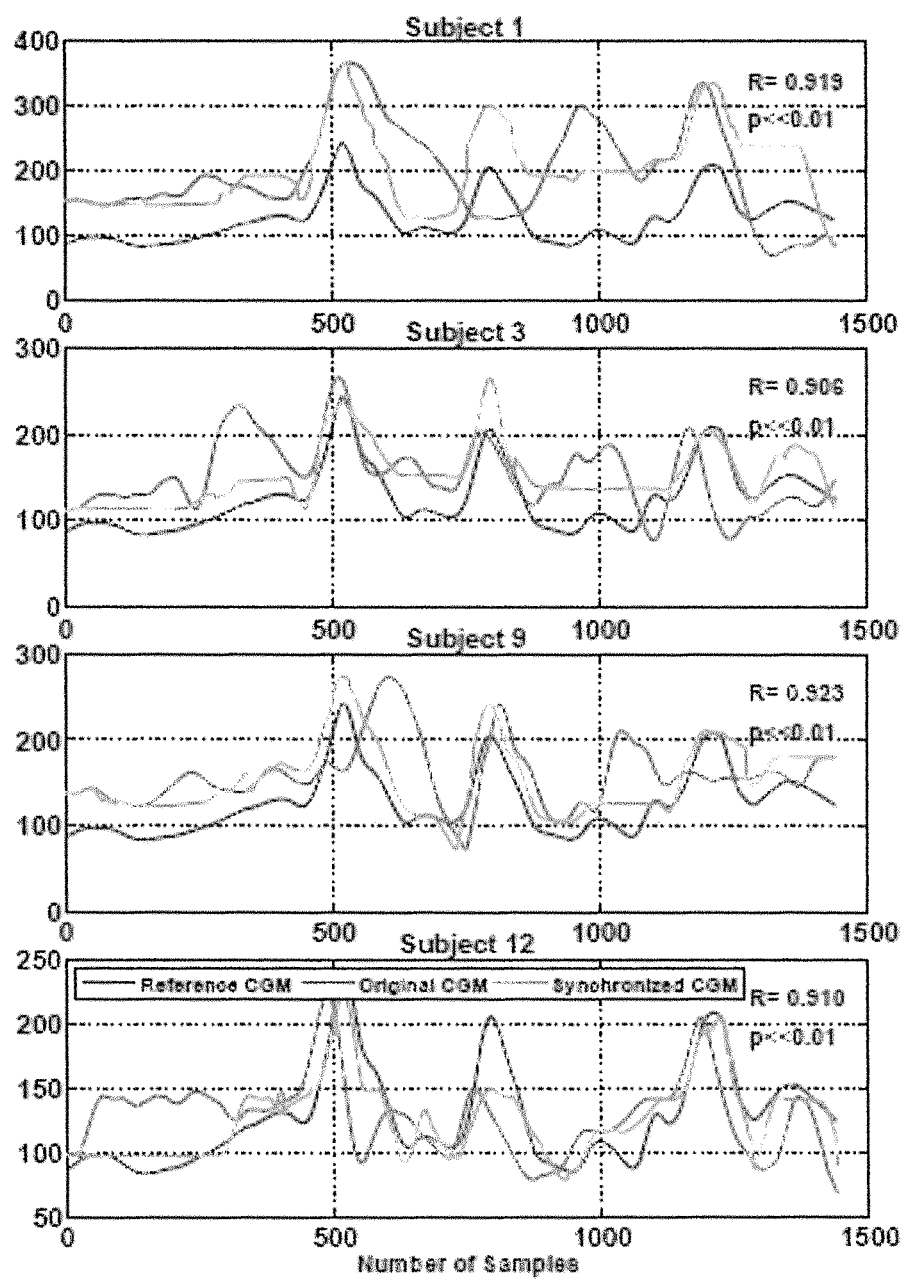
Figure 8:
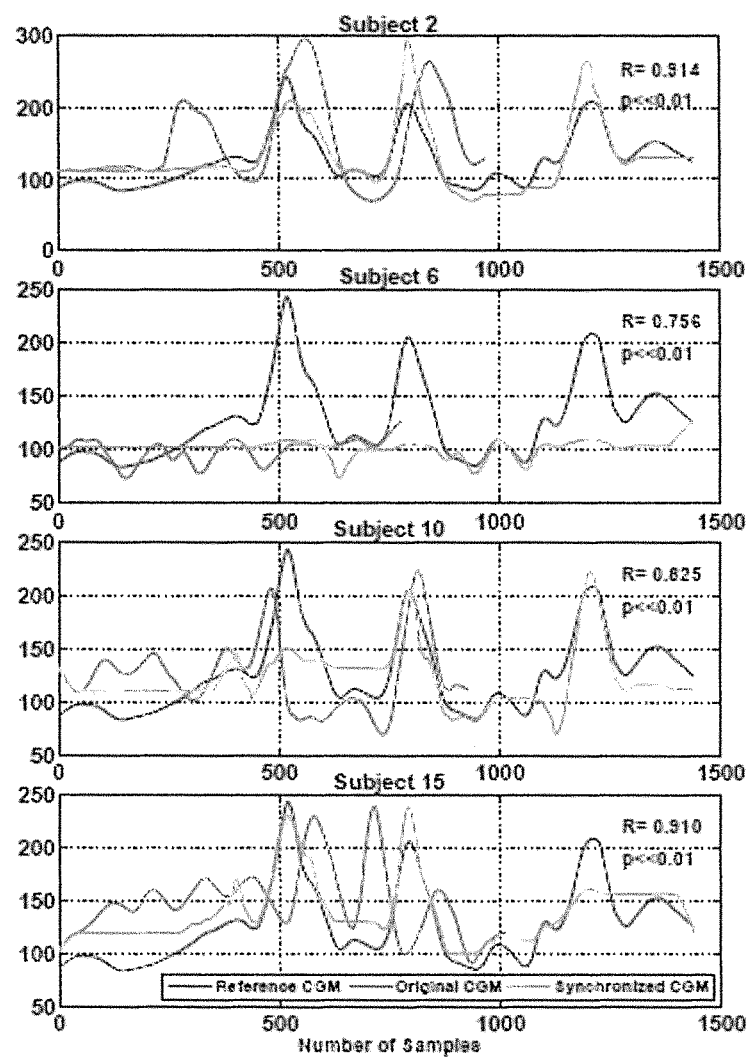

FIG. 7 shows the result from the second days of lour other subjects where the lengths of the testing signals are identical to the reference trajectory. The synchronization is done based on alignment of peak and nadir points. After the synchronization the signals are significantly correlated with the reference trajectory where low and high glucose values axe align over the duration of the reference trajectory. Similar results are obtained when the third days of four other experiments are synchronized with the reference trajectory (FIG. 8).

Figure 9:
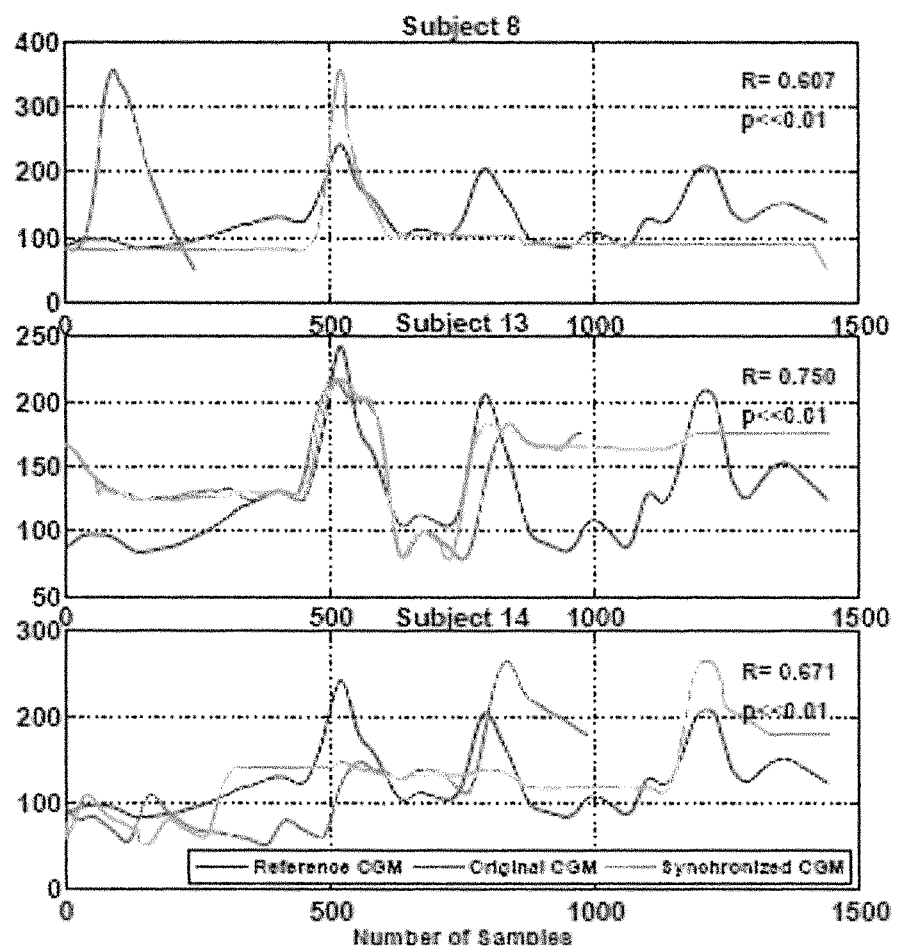
Figure 10:
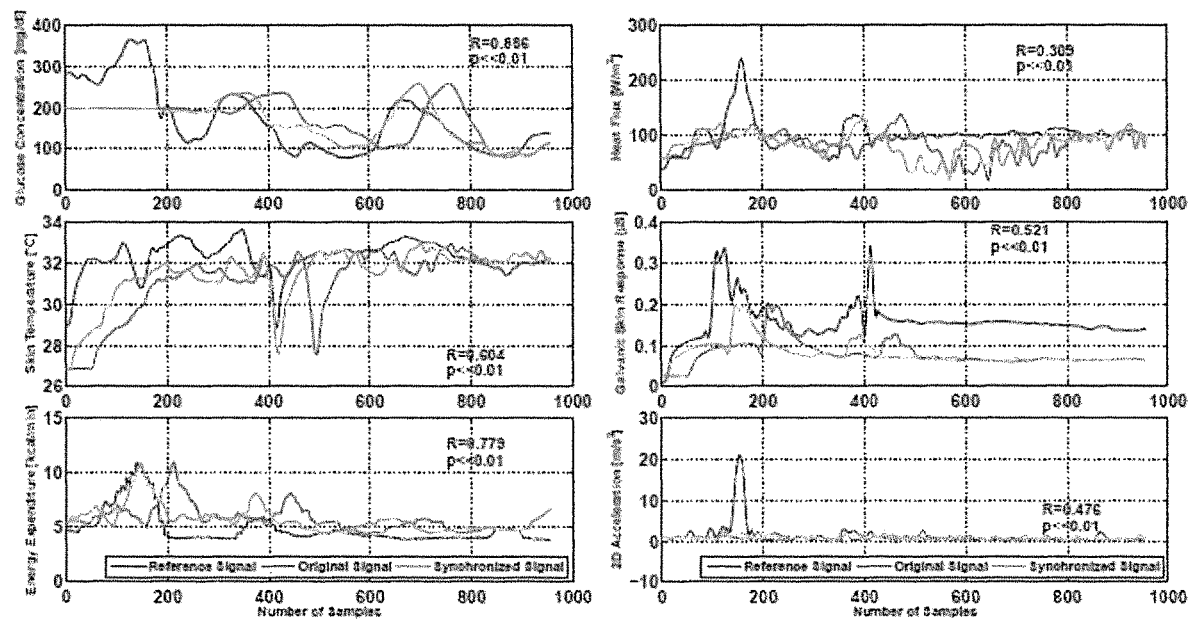

Table V shows the performance evaluation of the proposed method for 45 days data from 15 subjects. All 45 days datasets are synchronized with the reference day (second day of subject 3) with highly statistically significant correlations. The correlation coefficient for subject 8 (Day 1) and subject first days of subjects 13 and 14 (Day 3) are relatively smaller than other days. FIG. 9 shows that this is due to the collected data and the algorithm, still performs the best synchronization that can be done. FIG. 10 shows the result of the multivariable synchronization where, in addition to glucose measurements five more variables such as heat flux, skin temperature, galvanic skin response, energy expenditure and 2D acceleration are synchronized with the reference trajectories at the same time. Due to the high variations and complexity in the extra variables, the correlation coefficients between synchronized and reference signals are not as high as the single variable case but still statistically significant ($p \ll 0.01$). The proposed method is able to align similar events all variables. The two exercise sessions that are critical for an AP system are overlapped after synchronization even though they were performed at different times.

TABLE V

| Subject number | Day 1 | Day 2 | Day 3 |
|---|---|---|---|
| 1 | 0.7566 | 0.9185 | 0.8902 |
| 2 | 0.8929 | 0.8579 | 0.9141 |
| 3 | 0.8260 | 0.9064 | 0.7955 |
| 4 | 0.8553 | 0.8779 | 0.7600 |
| 5 | 0.9239 | 1.000 | 0.9468 |
| 6 | 0.7160 | 0.8449 | 0.7563 |
| 7 | 0.8713 | 0.8955 | 0.7791 |
| 8 | 0.6067 | 0.8372 | 0.7683 |
| 9 | 0.8470 | 0.9226 | 0.7142 |
| 10 | 0.8880 | 0.8614 | 0.8252 |
| 11 | 0.9175 | 0.9163 | 0.7879 |
| 12 | 0.8252 | 0.9104 | 0.8230 |
| 13 | 0.7955 | 0.8672 | 0.7501 |
| 14 | 0.8118 | 0.9068 | 0.6705 |
| 15 | 0.8440 | 0.8350 | 0.9095 |
| Average | 0.8282 | 0.8905 | 0.8060 |

All values are calculated based on statistical significance at $p \leq 0.01$.

In contrast to studies conducted in the clinical research facility with carefully controlled conditions closed loop at home is exposed to considerably more varied meal and exercise patterns. Participants may over- or underestimate carbohydrate content and may undertake unplanned activity and/or exercise. An AP system should be tested under completely free-living conditions for prevention of any safety related issues that may not be observed in a well-controlled environment before it is commercially available. However, the statistical analysts of the results that are obtained under free-living conditions may not be easily done due to large variation over the duration of experiments and between participants, this method is able to synchronize data that are collected under non-standardized conditions. The synchronization aligns similar events over different patients and provides a better interpretation for the statistical analysis of the obtained results.

Fault Detection

Error detection and diagnosis, and mitigation of risks of a faulty AP are important in the adoption of AP systems by patients. The success of these features will improve reliability and GC control. Embodiments of this invention rely on the use of both first-principles models to detect significant changes in model parameters to indicate abnormalities to system operation and data-driven models that can achieve detection and diagnosis by evaluating the statistics of current measurements with statistical limits established by using historical data with no abnormalities. In addition, algorithms axe developed to estimate plasma insulin and check the performance of pump operation and insulin delivery to the patient. The use of biometric signals provides significant advantages in the accuracy and reliability of the techniques developed with respect to algorithms that rely only on GC measurements.

Faults in subcutaneous glucose concentration readings can cause errors in the computation of insulin infusion rates, which can lead to hypoglycemia or hyperglycemia in artificial pancreas control systems for patients with type 1 diabetes. The invention includes automatically monitoring for and determining a faulty or missing measurement information transmitted by the continuous glucose monitor or the physiological sensors. The device of this invention further includes a fault detection and diagnosis module to monitor in real time sensors, the insulin pump, and/or the modules of the device for malfunctions, such as by using various sources of information and models, including the estimates of plasma glucose concentration and/or plasma insulin concentration. In embodiments of this invention, multivariable statistical monitoring methods are used for detection of faults in glucose concentration values reported by; a subcutaneous glucose sensor.

Embodiments of the invention include real-time model-based fault detection methods that integrate data-driven and model-based methods. The methods are able to detect CGM failures with a high rate of success. Embodiments of this invention include a nonlinear first principles glucose/insulin/meal dynamic model. Unscented Kalman filter can be used for state and parameter estimation of the nonlinear model. Principal component analysis models are used for detection of dynamic changes. A K-nearest neighbors classification algorithm can be used for diagnosis of faults.

As an example, data from 51 subjects was used to assess the performance of a method according to this invention. The results indicate that the method works successfully with 84.2% sensitivity. The fault detection method can decrease the effects of faults on insulin infusion rates and reduce the potential for hypo- or hyperglycemia for patients with T1D.

Continuous glucose monitoring (CGM) sensors are critical components of closed-loop (CL) artificial pancreas (AP) control systems that aim to automatically regulate blood glucose concentration (BGC) of patients with type 1 diabetes (T1D). However, CGM sensors may not be able to follow actual BGC due to loss of sensor sensitivity, dislodging, interruption in signal transmission and pressure on sensor patch-area, CGM measurements provide glucose concentration (GC) information to AP systems for calculation of insulin amounts. Erroneous CGM measurements may cause wrong amounts of insulin to be infused which subsequently may cause hypo- or hyperglycemia. Hence, detection of abnormalities and faults in CGM readings are important for proper operation of APs.

Fault detection algorithms can be divided into three main groups: qualitative model-based methods, quantitative model-based methods, and process history-based (data-driven) methods. Qualitative model-based methods use knowledge-based (expert) systems and may not be appropriate by themselves for fault detection in complex biological systems. A knowledge-based system uses, if-then-else rules that mimic the reasoning, of a human expert in solving problems. As the number of if-then-else rules grows with the behavioral complexity of the system some rules may conflict with the new rules and the maintenance of the system and conflict resolution may become challenging. In contrast, the process history based methods require only the availability of large amounts of historical process data. Relations between variables, patterns that indicate various abnormalities, and/or statistical limits that indicate significant deviations are extracted fem the historical data and used for fault detection. However, the performance of these methods depends on the size and quality of historical data. A model-based fault detection method can be developed by using first principles such as material and energy balances. But the cost of model development may be high as the model may become too complex and too large to run model computations on the computer within an acceptable amount of time as more details are added.

In the example, a method that is a combination of model- and process history-based algorithms was developed for detection of CGM related faults. The model-based component was based on the extension of Bergman's model.

Bergman et al. developed the first three-compartment "minimal model" to analyze plasma glucose- and insulin dynamics during an intravenous glucose tolerance test. Later, various modified versions of the minimal model were proposed in order to separate the effect of glucose production from utilization and to capture absorption, distribution and disposal glucose/insulin dynamics. The effects of free fatty acid (FFA) and exercise were also included in recent versions of the minimal model. Due to complexity of the human body, some states defined in first-principle models may not be measurable. The non-measurable states are usually estimated from available measurements. Model parameters are identified from available measurements as well. However, time-invariant model parameters are not appropriate for the minimal model used in this work because of intra- and inter-subject variability over time. Therefore, the model states and parameters are estimated simultaneously. An Unseen-fed Kalman Filter (UKF) is implemented for state estimation of nonlinear systems. Defining uncertain model parameters as augmented states, simultaneous state and parameter estimation can be performed.

The data-driven portion of the fault detection method is based on principal components analysis (PCA), To date, support vector machine wavelet Kalman filter, kernel density based stochastic, model, rates of changes threshold based model and PCA methods have been tested for detection of CGM failures. PCA involves the orthogonal decomposition of the set of process measurements along the directions that explain the maximum variation in the data. PCA was used to develop a model that describes the expected variation under normal conditions.

Figure 11:
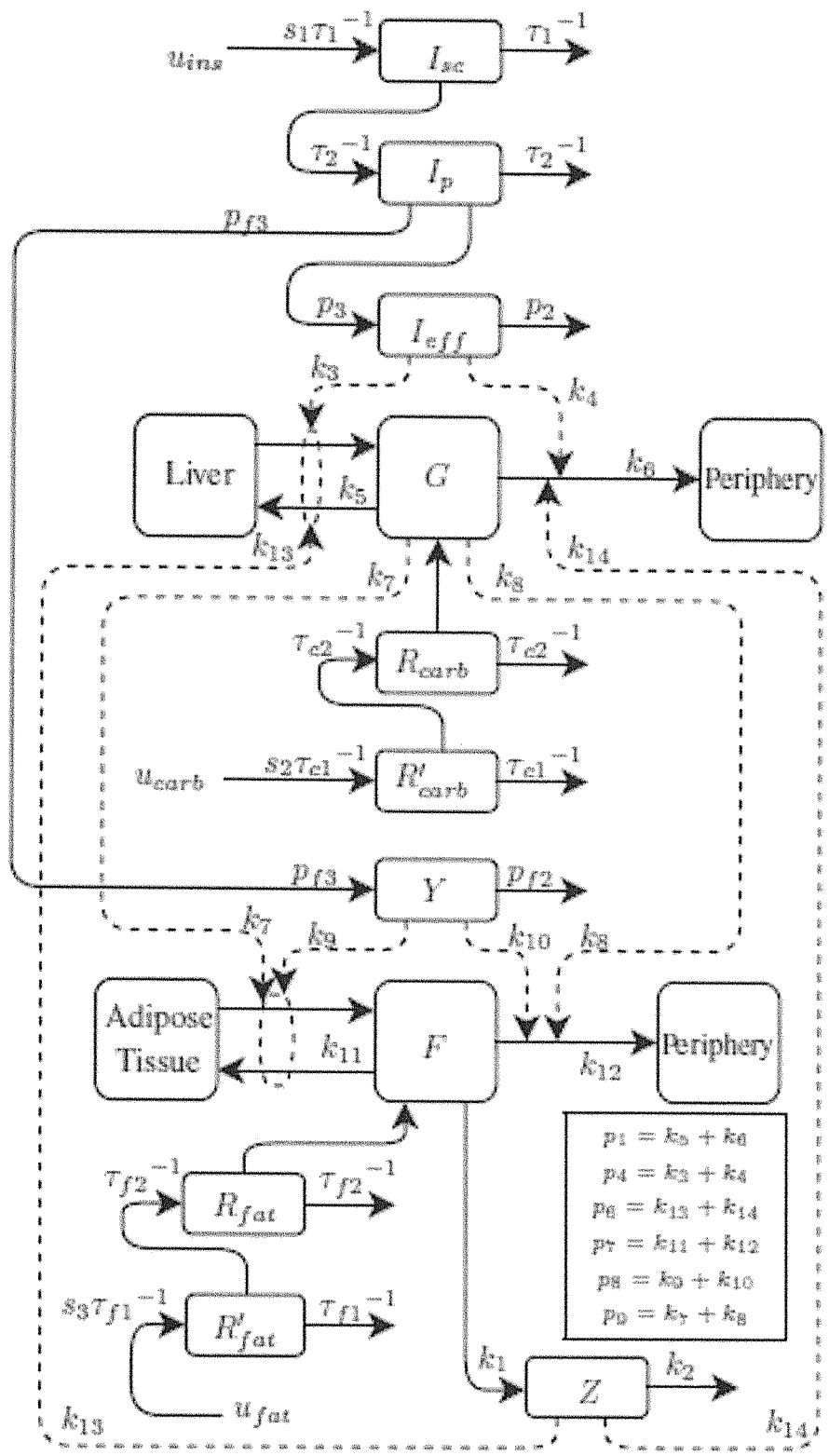
FIG. 11 illustrates a modified version of the extended minimal model, according to one embodiment of this invention.

A modified version of the extended minimal model that was developed by Roy et al., "Dynamic modeling of free fatty acid, glucose, and insulin: An extended "minimal model"," *Diabetes technology & therapeutics*, vol, 8, no, 6, pp. 617-626, 2006, was used (FIG. 11). The insulin dynamics are described with three cascade compartments.

$$\frac{dI_{sc}(t)}{dt} = -\frac{1}{\tau_1}I_{sc}(t) + \frac{s_1}{\tau_1 V_{ins}}u_{ins}(t) \quad (24)$$

$$\frac{dI_{eff}(t)}{dt} = -p_2 I_{eff}(t) + p_3 I_p(t) \quad (25)$$

$$\frac{dI_p(t)}{dt} = -\frac{1}{\tau_2}I_p(t) + \frac{1}{\tau_2}I_{sc}(t) \quad (26)$$

where $I_{sc}$, $I_p$, $I_{eff}$ represent subcutaneous, plasma and effective insulin concentrations respectively, $u_{ins}$ is also the amount of given Insulin. Plasma glucose concentration G is defined as a function of effective insulin, remote plasma FPA concentration (Z) and rate of appearance of carbohydrate ($R_c$):

$$\frac{dG(t)}{dt} = \quad (27)$$
$$-p_1 G(t) - p_4 I_{eff}(t) G(t) + p_6 G(t) Z(t) + p_1 G_b - p_6 G_b Z_b + s_2 R_e(t)$$

where $G_b$ and $Z_b$ show basal values for plasma glucose and remote plasma FFA concentration, respectively. FFA dynamics are also represented by a three-compartments model;

$$\frac{dY(t)}{dt} = -p_{12}Y(t) + p_{13}I_p(t) \quad (28)$$

$$\frac{dF(t)}{dt} = -p_7 F(t) - p_6 Y(t)F(t) + \quad (29)$$
$$p_9(G)F(t)G(t) + p_7 F_b - p_9(G)F_b G_b + s_3 R_f(t)$$

$$\frac{dZ(t)}{dt} = -k_2 Z(t) + k_1 F(t) + k_2 Z_b - k_1 F_b \quad (30)$$

where Y, F and $F_b$ represent FFA-related insulin concentration and plasma FFA concentration, and basal plasma FFA concentration, respectively. Similar to plasma glucose, the plasma FFA concentration is a function of Y, F and rate of appearance of fat ($R_{fat}$). Rates of appearance of carbohydrate and fat are defined as two-compartments models denoted as R and R' in FIG. 11:

$$R_{carb}(t) = \frac{u_{carb}(t)}{V_{carb}(\tau_{c1} - \tau_{c2})}\left[e^{-\frac{1}{v_{c1}}} - e^{-\frac{1}{v_{c2}}}\right] \quad (31)$$

$$R_{fat}(t) = \frac{u_{fat}(t)}{V_{fat}(\tau_{f1} - \tau_{f2})}\left[e^{-\frac{1}{v_{f1}}} - e^{-\frac{1}{v_{f2}}}\right] \quad (32)$$

where the Eqs. (8) and (9) represent both compartments (R and R') for carbohydrate and fat, respectively. Furthermore, and $u_{fat}$ are $u_{carb}$ are the amount of fat and carbohydrate consumed, respectively. Three additional parameters ($s_1$, $s_2$, $s_3$) are added to the extended model to describe the ratio of absorption of insulin, carbohydrate and fat, respectively. Also the rate of appearance of fat $R_{fat}$ is defined in a similar way to rate of appearance of carbohydrate $R_{carb}$. All unknown parameters in Eqs. (1)-(9) are defined to be time-varying.

Extended Kalman filter (EKF) is one of the most common techniques used for state estimation of nonlinear systems. Flow-ever, the linear approximation at operating point approach in EKF may cause errors when a time-varying model is used. Also, calculation of Jacobian matrices might be critical when a high-order model is used in real-time applications. The UKF is designed to overcome the drawbacks of EKF, and can easily be implemented to high order systems without calculation of Jacobian matrices.

To develop the UKF, the model in Eq. (24)-(32) is discretized using first forward difference derivative approximation with a 5-minutes sampling time. The notation for plasma glucose concentration G(t) in Eq. (28) is replaced with subcutaneous glucose concentration (CGM) $G_s(k)$ in discrete from. The relation between two variables was shown to be a one compartment model with a delay parameter which was neglected in the study due to difficulties in validation. The non-linear discrete model is written in non-linear state-space form:

$$\xi(k+1)=f(\xi(k),u(k),\theta(k))+w(k)$$

$$y(k)=g(\xi(k),u(k),\theta(k))+v(k) \quad (33)$$

where $\xi(k)$, $u(k)$, $y(k)$, $\theta(k)$, $w(k)$, $v(k)$ are model states, inputs, outputs, uncertain model parameters, process noise and measurement noise, respectively. The nonlinear-functions/(•) and g(•) are defined from Eq. (24)-(33). In addition to $u_{ins}$, $u_{carb}$ and $u_{fat}$, the basal values $G_b$, $F_b$, $Z_b$ are defined as inputs.

The estimation of states and parameters is done simultaneously, by defining the following augmented state vector:

$$x(k)=[\xi(k)^T \ \theta(k)^T]^T \quad (34)$$

where the superscript T denotes matrix transpose. Defining L as the dimension of x vector, the sealer weights $W_i$ are defined:

$$W_o^x = \mu/(L+\mu) \quad (35)$$
$$W_o^y = \mu/(L+\mu) + (1-\alpha^2+\beta)$$
$$W_i^x = W_i^z = 1/[2(L+\mu)]$$

where $i=1, \ldots, 2L$ and $\mu=\alpha^2(L+\kappa)$. The tuning parameters $\alpha$, $\beta$ and $\kappa$ are selected to be 1, 2 and 0, respectively. The sigma-points vectors $\chi_i$ are deterministically selected sets of sample points to more accurately map the probability distribution than the linearization of standard EKF and are defined as:

$$x_o(k-1) = \hat{x}(k-1) \quad (36)$$
$$x_i(k-1) = \hat{x}(k-1) + \gamma \times \eta_i$$
$$x_{i+L}(k-1) = \hat{x}(k-1) - \gamma \times \eta_i$$

where $\eta_i$ is the $i^{th}$ column ($i=1, \ldots, L$) of the square root of the augmented covariance matrix $P(k-1)$ and the parameter $\gamma=\sqrt{L+\mu}$.

Prior sigma-points estimations $\chi_i^-(k)$ are calculated by propagating the sigma-points $\chi_i(k-1)$ through the nonlinear function $f(\bullet)$. The prior sigma-points are trimmed with a nonlinear optimization to prevent non-realistic estimations such as negative values in concentrations.

$$x_i^-(k) = \min\ [\Delta x_i]^T[\Delta x_i]$$
$$\Delta x_i = x_i^-(k) - f(x_i(k-1))$$
$$x_{min} \leq x_i^-(k) \leq x_{max}$$
$$i=0, \ldots, 2L \quad (37)$$

The prior state estimations and covariance matrix are calculated as:

$$\hat{x}^-(k) = \min\ [\Delta \hat{x}^-]^T[\Delta \hat{x}^-] \quad (38)$$
$$\Delta \hat{x}^{-1} = \hat{x}^-(k) - \sum_{i=0}^{2L} W_i^x x_i^-(k)$$
$$\hat{x}_{min}^- \leq \hat{x}^{-1}(k) \leq \hat{x}_{max}^-$$
$$P^-(k) = \sum_{i=0}^{2L} W_i^y [x_i^-(k) - \hat{x}^{-1}(k)][x_i^-(k) - \hat{x}^{-1}(k)]^T + Q_P \quad (39)$$

where $Q_p$ is the covariance matrix of the process noise. The prior sigma-points estimations are propagated through the nonlinear function $g(\bullet)$ for calculation of prior outputs sigma-points $\Upsilon_i^-$;

$$\gamma_i^-(k) = g(x_i^-(k)) \quad (40)$$
$$i = 0, \ldots, 2L$$

The measurement estimations are obtained from the output sigma-points as:

$$\hat{y}^-(k) = \sum_{i=0}^{2L} W_i^x \gamma_i^-(k) \quad (41)$$

The innovation covariance and cross-covariance matrices are calculated as:

$$P_{yy}(k) = \sum_{i=0}^{2L} W_i^y [\gamma_i^-(k) - \hat{y}^{-1}(k)][\gamma_i^-(k) - \hat{y}^{-1}(k)]^T + Q_m \quad (42)$$

$$P_{xy}(k) = \sum_{i=0}^{2L} W_i^y [x_i^-(k) - \hat{x}^{-1}(k)][\gamma_i^-(k) - \hat{y}^{-1}(k)]^T \quad (43)$$

where $Q_m$ represent the covariance matrix for process measurement noise. Finally, the Kalman filter gain and the updated state vector estimation and covariance matrix are calculated:

$$K(k) = P_{xy}(k)(P_{yy}(k))^{-1} \quad (44)$$
$$\hat{x}(k) = \min[\Delta \hat{x}]^T[\Delta \hat{x}] \quad (45)$$
$$\Delta \hat{x} = \hat{x}(k) - (\hat{x}^{-1}(k) + K(k)(y(k) - \hat{y}^{-1}(k)))$$
$$\hat{x}_{min} \leq \hat{x}(k) \leq \hat{x}_{max}$$
$$P(k) = P^-(k) - K(k)P_{vv}(k)(K(k))^T \quad (46)$$

The PCA model is built, from an appropriate (no faults) reference data. For a continuous process, the data can be represented by matrix $\tilde{X}_{n \times m}$ where n is the number of observations and m the number of variables. The directions extracted by the orthogonal decomposition of $\tilde{X}$ the eigenvectors $\tilde{p}_i$ of $\tilde{X}^T\tilde{X}$ also called principal components (PC) loadings;

$$\tilde{X} = \tilde{t}_1 \tilde{p}_1^T + \tilde{t}_2 \tilde{p}_2^T + \ldots + \tilde{t}_\alpha \tilde{p}_\alpha^T + \tilde{E} \quad (47)$$

where $\tilde{E}$ is the residuals matrix. The dimension a is chosen such that most of the significant process information is captured by the $\tilde{t}_{i \leq T}$ and $\tilde{E}$ contains mostly random error. The relationship between $\tilde{X}$, loading and score matrices can be expressed as:

$$\tilde{X} = \tilde{T}\tilde{P}^T + \tilde{E} \quad \tilde{E} = \tilde{X} - \underline{\tilde{X}} \quad (48)$$

where $\underline{\tilde{X}} = \tilde{T}\tilde{P}^T$ and $\tilde{P}$ is the m+$\alpha$ matrix of loadings and $\tilde{T}$ is the n×$\alpha$ score matrix. PCA transforms the coordinate system of a data set for more efficient description of variability in data. The PCs can be computed by singular value decomposition (SVD) of the data matrix $\tilde{X} = \tilde{U}\tilde{\Sigma}\tilde{V}^T$, where the columns of $\tilde{U}$ the columns of $\tilde{V}$ are the normalized eigenvectors of $\tilde{X}\tilde{X}^T$, are the normalized eigenvectors of $\tilde{X}^T\tilde{X}$, and $\tilde{\Sigma}$ is a diagonal matrix having as its elements the singular values and thus $\tilde{P}=\tilde{V}$ and $\tilde{T}=\tilde{U}\tilde{\Sigma}$.

The UKF estimations are integrated with the PCA model as:

$$\tilde{X}_{n \times m} = [\hat{x}(1)\ \hat{x}(2) \ldots \hat{x}(n)]^T \quad (49)$$

where $\hat{x}(k)$ for $k=1, \ldots, n$ are obtained from Eq. 45.

Hotelling's $T^2$ chart detects the deviation of a new observation from the reference model. The statistical limits of the $T^2$ are defined as:

$$T_a^2 \sim \left[\frac{\alpha(n^2-1)}{n(n-\alpha)}\right] F_{a,n-o,\alpha} \qquad (50)$$

where $F_{a,n-a,\alpha}$ represents F distribution with a and n−a degrees of freedom and $\alpha$ is the confidence interval.

SPE charts (also called Q charts) show deviations from reference data that are not captured by the model. The statistical limits for SPE are defined as:

$$SPE_\alpha = \theta_1 \left[1 - \frac{\theta_2 h_0(1-h_0)}{\theta_1^2} + \frac{z_\alpha(2\theta_2 h_0^2)^{\frac{1}{2}}}{\theta_1}\right]^{\frac{1}{h_0}} \qquad (51)$$

$$\theta_i = \sum_{j=a+1}^{m} \lambda_j^i, \text{ for } i=1,2, \text{ and } 3 \qquad (52)$$

$$h_0 = 1 - \frac{2\theta_1 \theta_3}{3\theta_2^2} \qquad (53)$$

where $z_\alpha$ is the standard normal variable corresponding $\alpha$ confidence interval and $\lambda_i$ represent the eigenvalues of $\tilde{X}^T \tilde{X}/(m-1)$.

Once the control limits for $T_a^2$ and $SPE_a$ are defined, for a new observation vector $x_{new}(k)$, a fault is detected if any of the following conditions is satisfied:

$$T_a^2 \le T^2(k) = [x_{new}(k)\tilde{P}]A^{-1}[x_{new}(k)\tilde{P}]^T \qquad (55)$$

$$SPE_a \le SPE(k) = [x_{new}(k) - x_{new}(k)\tilde{P}\tilde{P}^T][x_{new}(k) - x_{new}(k)\tilde{P}\tilde{P}^T]^T \qquad (55)$$

where $\Lambda$ is a diagonal matrix consists of the eigenvalues $\lambda_i$ for $i=1,\ldots,a$. The selection of a is defined as:

$$a = \min a \qquad (56)$$

$$98 \le \frac{\sum_{i=1}^{a} \lambda_i}{\sum_{i=1}^{m} \lambda_i} 100$$

The two conditions in Eqs. (54) and (55) may be satisfied not only when there is a faulty reading in CGM measurements but also for some dynamic changes that are not included in the reference data matrix $\tilde{X}$. These dynamic changes may not be considered as a fault, in order to minimize the number of erroneous fault detections, a two-step fault diagnosis algorithm is developed to distinguish CGM faults from regular dynamic changes. After a fault is detected by either the $T^2$ or SPE statistics as in Eqs. (54) and (55), the source of the fault must be determined. This is indicated by the variables responsible for inflating $T^2$ and SPE statistics. The variables that made the largest contributions to the fault detection charts are considered to indicate the faults. The contribution of each variable onto the $T^2$ and SPE charts is calculated as:

$$CONT_j^{T^2}(k) = \left[x_{new,j}(k)\tilde{P}_j\right]\Lambda^{-1}\left[x_{new,j}(k)\tilde{P}_j\right]^T \qquad (57)$$

$$CONT_j^{SPE}(k) = \left[x_{new,j}(k) - x_{new,j}(k)\tilde{P}_j\tilde{P}_j^T\right]\left[x_{new,j}(k) - x_{new,j}(k)\tilde{P}_j\tilde{P}_j^T\right]^T \qquad (58)$$

where $x_{new,j}$ is the $j^{th}$ ($j=1,\ldots,m$) variable and $\tilde{P}_j$ is the $j^{th}$ row of the matrix $\tilde{P}$.

The k-nearest neighbors algorithm is a non-parametric classification method. An object is classified by a majority vote of its neighbors, with the object being assigned to the class, most common among its k nearest neighbors. The feature matrix $\check{x}$ and the output vector $\check{y}$ are defined as:

$$\check{x}(k) = [CONT^{T^2}(k) \; CONT^{SPE}(k)]$$

$$\check{y}(k) \in \{0,1\} = \{\text{nonfaulty, faulty}\} \qquad (59)$$

where $k=1,\ldots,N$ and N is the number of training data. The standardized Euclidean distance vector $\check{D}_{\check{x},\check{x}_{new}}$ between a new observation vector $\check{x}_{new}$ and the training data $\check{x}$ is defined as:

$$\check{D}_{\check{x},\check{x}_{new}}(k) = \sqrt{\sum_{j=1}^{2m} \frac{(\check{x}_j(k) - \check{x}_{new,j})^2}{\check{W}_j}} \qquad (60)$$

where $\check{W}_j$ is the variance of $j^{th}$ column of $\check{x}$ matrix for N observation. The KNN algorithm is:
1) Compute the distance $\check{D}_{\check{x},\check{x}_{new}}$ for every training data $k=1,\ldots,N$
2) Select $\check{k}$ lowest distances and corresponding $\check{y}(k)$
3) Select $\check{y}_{new}$ as the most frequent class from the previous step Data were collected from closed-loop studies conducted m multiple centers located in US, Israel, and Australia. A protocol with supervised free-living conditions without meal or activity restrictions was performed. Frequent YSI measurements were obtained (30 minutes most of the time) throughout the length of the experiment to ensure patient safety.

Overall 11 states with 23 unknown parameters were estimated with the UKF algorithm. All of the estimations were constrained with lower and upper bounds to prevent physiologically nonrealistic cases such as negative values in concentrations. The initial values, upper and lower bounds for states and parameters are shown in Table VI. The consumed fat amounts were assumed to be 35% of the consumed carbohydrates. The basal values Gb, Fb and Zb were defined to be constant inputs with values of 100, 380 and 190, respectively. The diagonal Qp matrix was defined to be $10^{-6}$ and $10^{-4}$ of the maximum values of states and parameters, respectively, which are shown in Table VI. The Qm is selected to be $10^{-1}$. The overall mean absolute relative difference (MARD) value (and standard deviation) for the Medtronic Paradigm Veo Enlite system (Medtronic, Northridge, Calif., USA) measured at the clinical research center, at home and in the hypoglycemic range to be 16.6 (13.5%, 20.5)% and 24.6 (18.8)%, respectively. In this example, every 30 minutes YSI measurements were interpolated and compared with CGM measurements. The time intervals where the difference between CGM and interpolated YSI values was more than 25% for three consecutive samples (15 minutes) were defined to be faulty CGM measurements.

PCA models were developed after removing the faulty intervals from each individual subject data. Half of the data was used for training of the PCA models. The confidence limit $\alpha$ in Eq. (60) was selected to be 0.9. In addition to 34 estimated variables from the UKF, the infused insulin (basal and bolus) and meal information was also used in the PCA models. The KNN classification algorithm was trained with randomly selected 50% of the faulty intervals for each subject. The rest of data was used for testing the proposed method. The ǩ value was selected to be 1.

TABLE VI

| Variables/Parameters [units] | Initial value | Minimum value | Maximum value |
|---|---|---|---|
| $I_{se}$ [μU/mL] | 0 | 0 | 500 |
| $I_p$ [μU/mL] | 0 | 0 | 500 |
| $I_{eff}$ [μU/mL] | 0 | 0 | 0.1 |
| $G_s$ [μg/dL] | CGM | 20 | 600 |
| Y [μU/mL] | 0 | 0 | 0.05 |
| F [μmol/L] | 380 | 0 | 3000 |
| Z [μmol/L] | 190 | 0 | 4500 |
| $R_{carb}$ [mg/(min · dL)] | 0 | 0 | 100 |
| $R_{fat}$ [μmol/(min · L)] | 0 | 0 | 500 |
| $\tau_1$ [min] | 95 | 10 | 180 |
| $\tau_2$ [min] | 95 | 10 | 180 |
| $p_1$ [1/min] | 0.075 | 0.0375 | 0.15 |
| $p_2$ [1/min] | 0.0463 | 0.2315 | 0.0926 |
| $p_3$ [1/min] | 0.000012 | 0.000006 | 0.000024 |
| $p_4$ [mL/(min · μU)] | 1.19 | 0.595 | 2.38 |
| $p_6$ [1/(min · μmol)] | 0.000075 | 0.0000375 | 0.00015 |
| $p_7$ [1/min] | 0.0375 | 0.01875 | 0.075 |
| $p_8$ [mL/(min · μU)] | 4.4655 | 2.23275 | 8.931 |
| $p_{f2}$ [1/min] | 0.2126 | 0.1063 | 0.4252 |
| $p_{f3}$ [1/min] | 0.0000115 | 0.00000575 | 0.000023 |
| $k_1$ [1/min] | 0.025 | 0.0125 | 0.05 |
| $k_2$ [1/min] | 0.0375 | 0.01875 | 0.075 |
| $s_1$ | 0.55 | 0.01 | 1 |
| $s_2$ | 0.55 | 0.01 | 1 |
| $s_3$ | 0.55 | 0.01 | 1 |
| $\tau_{c1}$ [min] | 85 | 10 | 240 |
| $\tau_{c2}$ [min] | 165 | 10 | 240 |
| $\tau_{f1}$ [min] | 85 | 10 | 240 |
| $\tau_{f2}$ [min] | 165 | 10 | 240 |
| $V_{ins}$ [L] | 1.25 | 0.5 | 2 |
| $V_{carb}$ [dL] | 117 | 50 | 2000 |
| $V_{fat}$ [L] | 11.7 | 5 | 20 |

Figure 12:
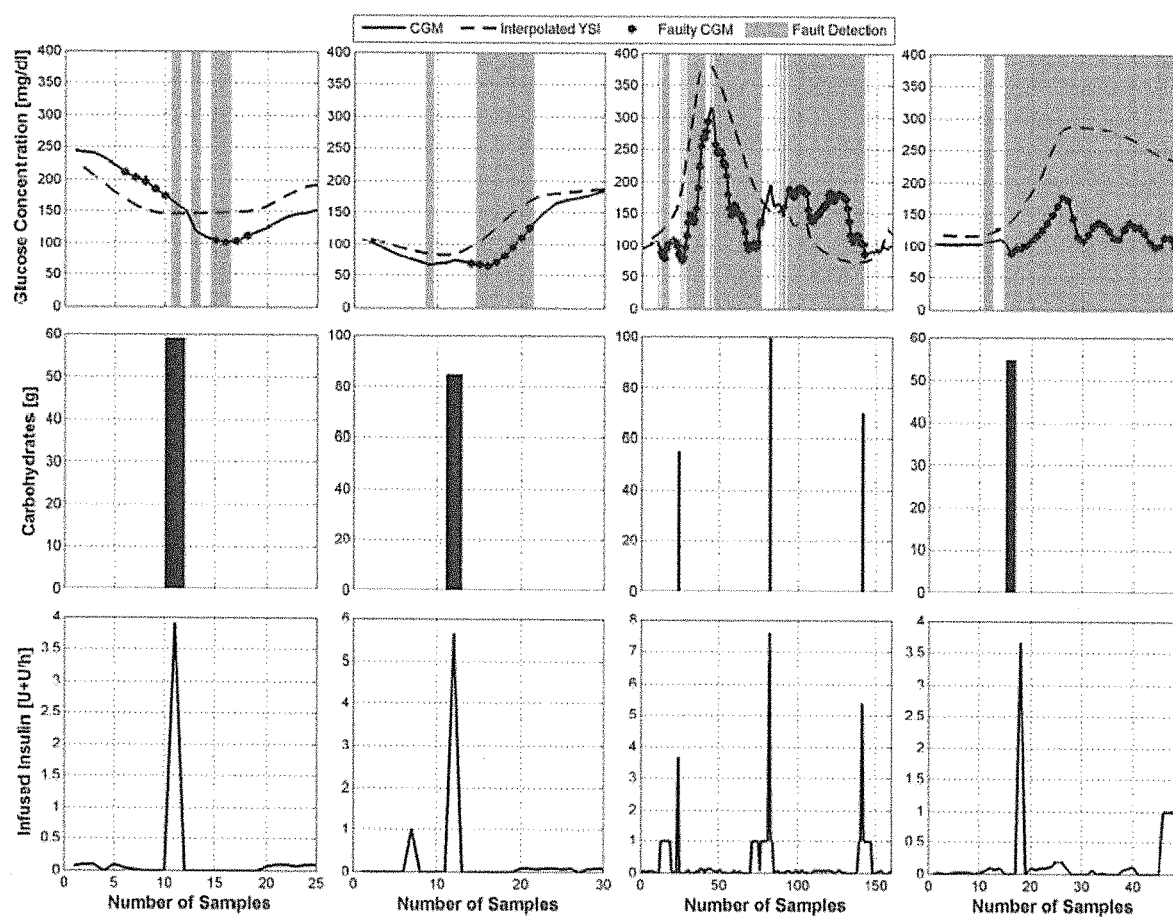
FIGS. 12-14 include graphs produced during testing of examples of the invention.
Figure 13:
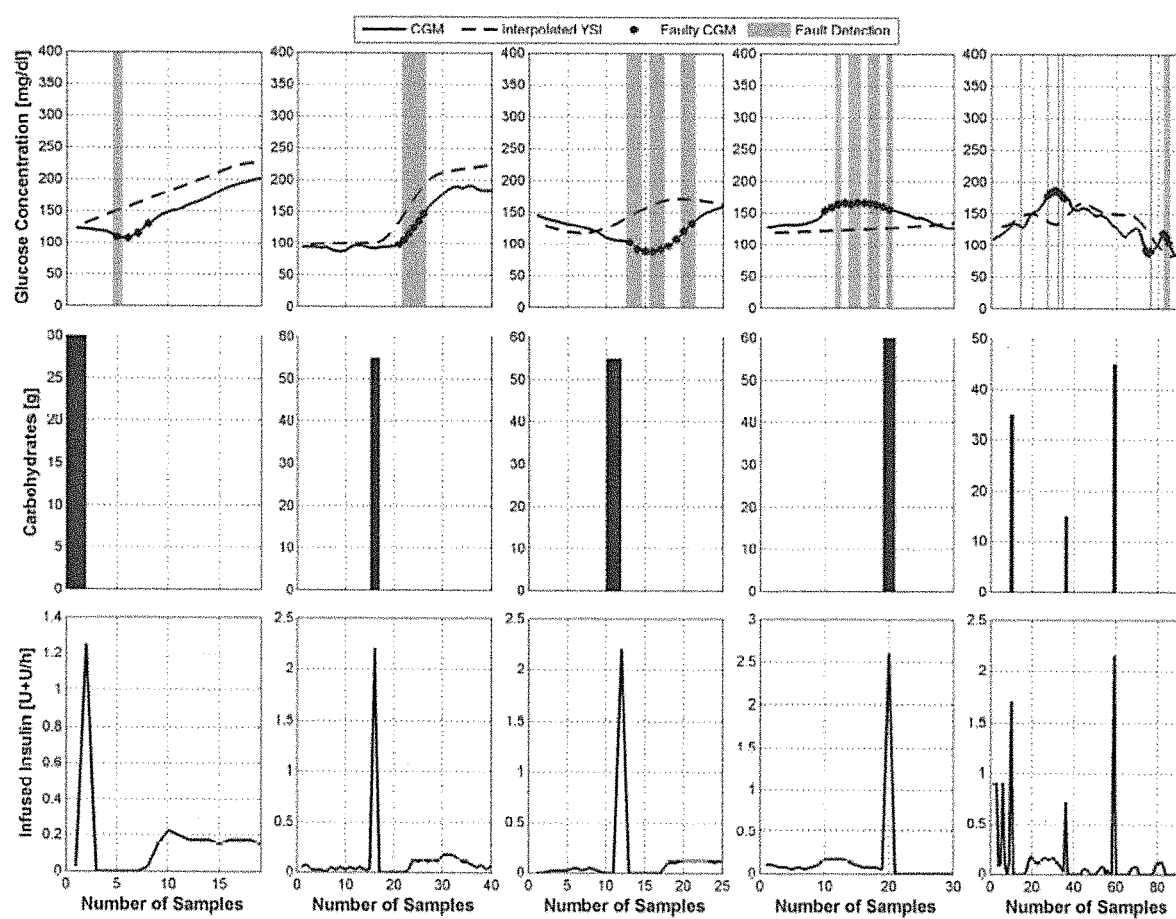
Figure 14:
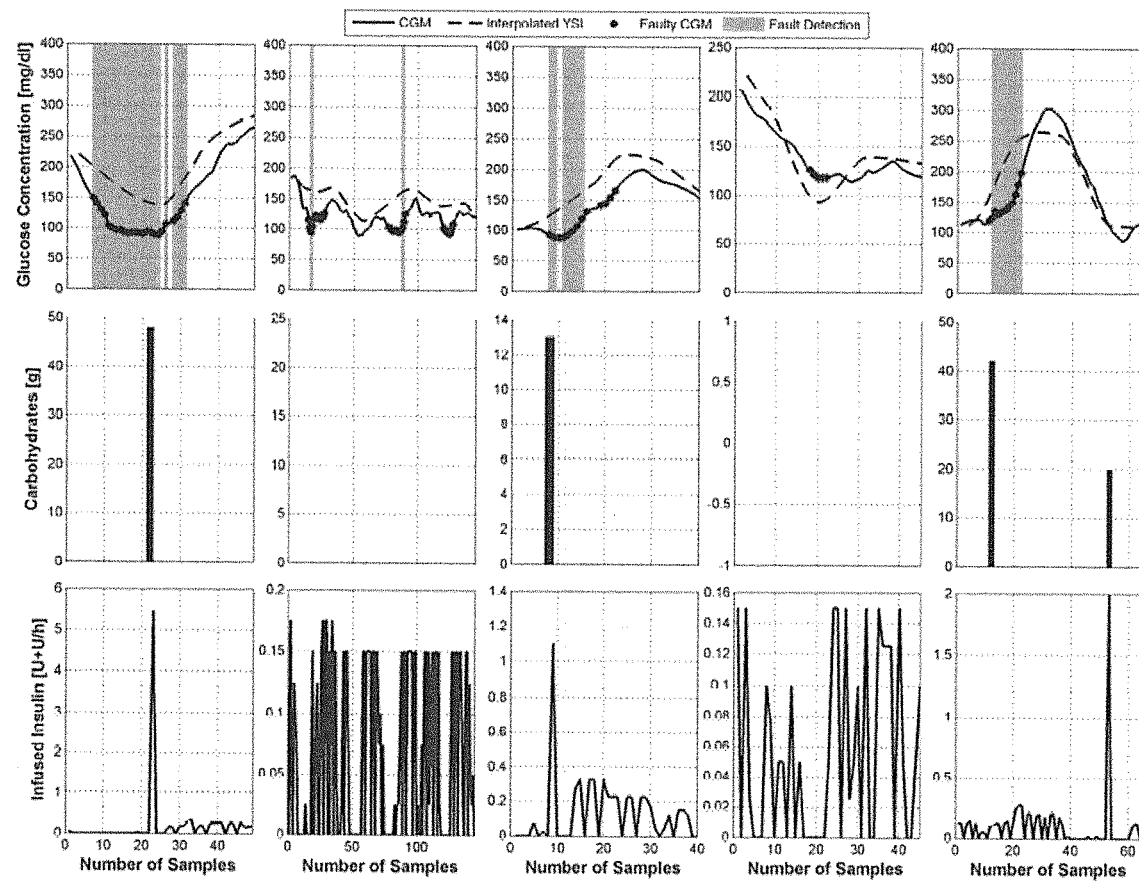

FIGS. 12-14 show the results of the proposed method tested on data from three different subjects. Almost all faulty CGM measurements are detected successfully. Most of the faults occurred during meal periods due to rapid increase in glucose values. Faults during meal periods may be very critical due to miscalculation of insulin rates by an AP system based on faulty readings. The faults that have large relative differences are detected more consistently as shown in FIG. 12.

As the proposed method integrates model-based and data-driven techniques with information about consumed meal and infused insulin amount, large delays in CGM readings are also detected even though YSI and CGM readings have similar trends as shown in FIG. 13.

In FIG. 14 two fault intervals were not detected. The first fault occurs during night time while the second one was seen after a meal session. These faults were not detected probably due to two possible reasons: (i) the training data for PCA may include an interval that had similar dynamic changes which prevents the $T^2$ and SPE to detect those points, (ii) due to randomly selection of training data, the faulty intervals may have not been defined in the KNN algorithm. Using larger training datasets can fix both problems.

The proposed algorithm was tested on data from 51 subjects. The mean value for training data size out of all subjects was found to be 25 hours (±29.1, Max: 192 hours, Min: 1 hour). Table VII summarizes the results of all subjects. 184 faulty CGM intervals were determined where the difference between COM measurements and interpolated YSI was more than 25%. Overall, 155 (84%) of the CGM failures were detected successfully with a 2.8 minutes average detection time. The time between the first fault detection and the first point of the true fault was defined as detection time. The shortest and longest detection times were determined to be 0 and 20 minutes, respectively. Due to exclusion of non-faulty subject data, Table VII shows at least one CGM fault for each subject. None of the subjects data have more than 1 missed fault. There were 12 cases where the algorithm detected faults but the difference between CGM and YSI was not larger than 25%. These cases are defined to be wrong alarms. The maximum number of wrong fault detection for one subject is found to be only 1.

TABLE VII

| | Overall 51 Subjects | Min out of 51 Subjects | Max out of 51 Subjects |
|---|---|---|---|
| Number of Faults | 184 | 1 | 11 |
| Detected Faults | 155 | 1 | 10 |
| Missed Faults | 29 | 0 | 1 |
| False Detection | 12 | 0 | 1 |
| Average Detection Time | 280 (±4.95) | 0 | 20 |
| Experiment Duration | 1413.75 | 3.33 | 194.08 |

Average detection time and experiment duration are reported in minutes and hours, respectively.

The method of this embodiment of the invention integrates elements of model-based and data-driven fault detection and diagnosis (FDD). By preserving the nonlinearity of the model, it has a better chance of representing the dynamic changes in the body with respect to FDD methods based on linearized models and Extended Kalman filters. By incorporating compartmental models in the method requires training data to be used for fault detection. The performance of the algorithm can be affected by the size of training data. The size should be large enough to contain different dynamical changes. Otherwise, some of new observed dynamic changes that are not captured in training data, might be considered as a fault which may increase the number of wrong detections (false positives). The quality of training data is also important. If the training data includes many faulty data, the proposed method may not be able to detect the faults with similar patterns in real-time and consider them as normal dynamical change which would increase the missed alarms and decrease the sensitivity of the algorithm. In some embodiments, 24 hours of training data that are known to have accurate COM measurements is sufficient. The training data can be updated or changed if another set of data is available.

By incorporating compartmental models in FDD, it enhances the data driven approach based on PCA and contribution plots. The computational cost of the algorithm can be addressed in two ways. As microprocessor power and memory of smartphones improve, the method can be handled in real time by a smartphone as each iteration of the proposed method is completed in less than a second. For extensive studies in the evaluation of the method, data can be sent to a cloud server that executes the method and provides the results to the smartphone for decision and action by the software, being run on the smartphone.

The results indicate that the method and module of this invention is able to detect most of the CGM failures with a high sensitivity. Such a fault detection, algorithm, can decrease the effects of faults on insulin infusion rates and reduce the potential for hypo- or hyperglycemia for patients with T1D by warning patients about CGM failures in manual operation or integrated in an artificial pancreas control system for CGM data reconciliation.

In another embodiment of this invention, multiway principal component analysis (MPCA) is used for detection of CGM related faults. MPCA provides a model that describes the expected variation under normal conditions. The MPCA model is built from an appropriate (no faults) reference data. Measurements from batch process are used to construct a three dimensions $\bar{x}$ matrix of size (I×J×K) where the matrix include K observations of J variables from I different batches. Once the three dimensions X matrix is unfolded into a two dimensional matrix X of (I×JK), regular PCA can be performed for extracting latent variables. PCA involves the orthogonal decomposition of the set of process measurements along the directions that explain the max imam variation in the data. For a continuous process, the data can be represented by matrix $X_{n \times m}$ where n is the number of observation and m the number of variables. The directions extracted by the orthogonal decomposition of X are the eigenvectors pi of $X^TX$ also called principal components (PC) loadings:

$$X = t_1 p_1^T + t_2 p_2^T + \ldots + t_a p_a^T + E \quad (61)$$

where E is the residuals matrix and superscript T denotes matrix transpose. The dimension a is chosen such that most of the significant process information is captured by the $t_i p_i^T$ terms, and E contains mostly random error. The projection of the measurements onto the eigenvectors defines new points in the measurement space that constitute the score matrix T whose columns are $t_j$. The relationship between T, P, and X can also be expressed as:

$$X = TP^T + E \quad E = X - \tilde{X} \quad (62)$$

where $\tilde{x} = TP^T$ and P is the m×a matrix of loadings and T is the n×a score matrix. PCA transforms the coordinate system of a data set for more efficient description of variability in data. The PCs can be computed by singular value decomposition (SVD) of the data matrix X:

$$X = U\Sigma V^T \quad (63)$$

where the columns of U are the normalized eigenvectors of $XX^T$, the columns of V are the normalized eigenvectors of $X^TX$, and S is a diagonal matrix having as its elements the singular values. The loadings and score matrices can be expressed as:

$$P = V \text{ and } T = U\Sigma \quad (64)$$

Hotelling's $T^2$ chart detects the deviation of new observation from the reference model that is captured by model. The statistical limits of the $T^2$ are defined as:

$$T_a^2 \sim \left[\frac{a(n^2-1)}{n(n-a)}\right] F_{a,n-a,\alpha} \quad (65)$$

where $F_{a,n-a,\alpha}$ represents F distribution with a and n–a degree of freedom and a confidence-interval.

SPE (also known as Q statistic) charts show deviations reference data that are not captured by the model. The statistical limits for SPE are defined as:

$$SPE_a = \theta_1 \left[1 - \frac{\theta_2 h_0(1-h_0)}{\theta_1^2} + \frac{z_\alpha(2\theta_2 h_0^2)^{\frac{1}{2}}}{\theta_1}\right]^{\frac{1}{h_0}} \quad (66)$$

$$\theta_i = \sum_{j=a+1}^{m} \lambda_j^i, \text{ for } i = 1, 2, \text{ and } 3 \quad (67)$$

$$h_0 = 1 - \frac{2\theta_1 \theta_3}{3\theta_2^2} \quad (68)$$

where $z_a$ is the standard normal variable corresponding to a confidence interval and li represent the eigenvalues of $X^TX = (m-1)$.

Once the control limits for $T_a^2$ and $SPE_a$ are defined, for a new observation vector x(k) a fault is detected if any of the following condition is satisfied:

$$T_a^2 \leq T^2(k) = \sum_{i=1}^{a} \frac{t_i^2(k)}{\lambda_i} \quad (69)$$

$$SPE_a \leq SPE(k) = \sum_{j=1}^{m} [x_j(k) - \hat{x}_j(k)]^2 \quad (70)$$

where $\hat{x}(k)$ is the estimation of the observed is vector x(k) and obtained from Eq. (62).

In this example, the selection of the number of principal components a is defined as an optimization problem subject to the percentage of variance of reference data:

$$a = \begin{cases} \text{minimize } a \\ \text{such that, } 95 \leq \frac{\sum_{i=1}^{a} \lambda_i}{\sum_{i=1}^{m} \lambda_i} \times 100 \end{cases} \quad (71)$$

Seven different three-day CL scenarios are generated with a five-minute sampling time tested on a virtual patient using the UVa/Padova metabolic simulator. The controller of the simulator is used for insulin calculation. To simulate realistic ambulatory conditions, some settings are varied to accommodate variations in daily life, including different meal amounts at different times, late night snacks in some scenarios and different meal consumption times (Table VIII). For each scenario fifty simulations are run. Mean trajectory of every ten simulations are calculated and used as noise-free CGM signal, first six scenarios are used for development of MPCA model while the data from the seventh scenario is used for fault detection purpose. Each three-day scenario is defined to be a batch with the CGM measurements as the only variable. The reference PCA model matrix X includes 30 batches with 1 variable and 864 observations.

Figure 15:
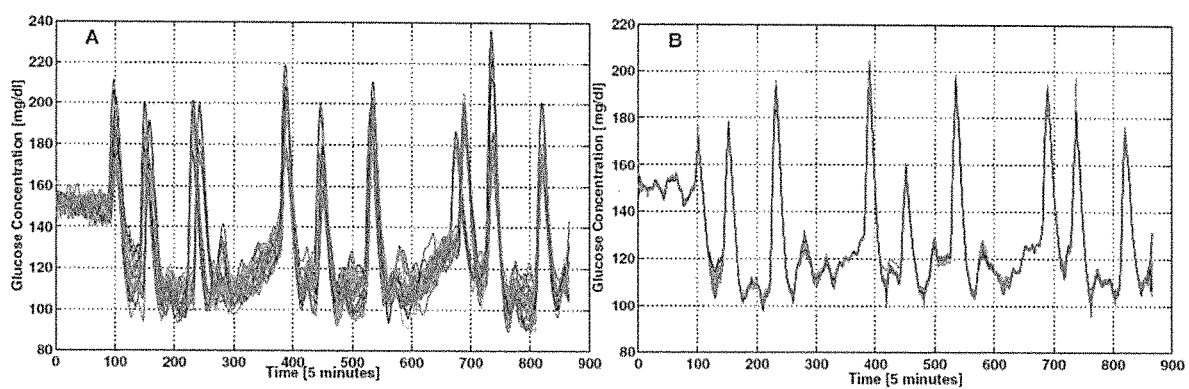
FIG. 15 includes graphs produced during testing of examples of the invention.

Due to variations in scenarios, glucose profile can be significantly different from each other (FIG. 15A). This kind of mismatch in reference data can cause wrong or missed fault detections. Before performing the PCA algorithm the reference data must be synchronized. Dynamic time warping (DTW) is used for synchronization of mismatched batches (scenarios). The results of synchronized scenarios after performing DTW are shown in FIG. 15B.

TABLE VIII

|     | S1       | S2        | S3       | S4       | S5       | S6       | S7       |
|-----|----------|-----------|----------|----------|----------|----------|----------|
| Dur | 15       | 15        | 15       | 30       | 30       | 20       | 15       |
| B   | 07.00/40 | 07.00/60  | 07.30/50 | 07.40/30 | 07.20/30 | 07.30/30 | 07.10/45 |
| L   | 12.00/50 | 12.00/75  | 11.35/75 | 11.55/60 | 11.3/60  | 11.45/60 | 12.15/62 |
| D   | 19.00/70 | 19.00/55  | 18.00/60 | 18.25/80 | 18.30/80 | 18.00/80 | 19.15/55 |
| S   | —        | —         | —        | —        | 22.00/25 | —        | 22.30/20 |
| B   | 07.00/40 | 07.00/73  | 07.15/70 | 07.05/70 | 07.25/70 | 07.15/70 | 07.30/53 |
| L   | 12.00/50 | 12.00/80  | 12.30/70 | 12.10/45 | 12.55/45 | 12.30/45 | 11.45/60 |
| D   | 19.00/70 | 19.00/68  | 19.30/85 | 19.30/70 | 19.10/70 | 19.30/70 | 18.30/68 |
| S   | —        | —         | —        | —        | 23.00/15 | —        | —        |
| B   | 07.00/40 | 07.00/45  | 08.15/60 | 08.15/60 | 08.00/55 | 08.15/60 | 07.20/45 |
| L   | 12.00/50 | 12.00/105 | 12.15/95 | 12.15/65 | 12.25/65 | 12.15/75 | 12.45/85 |
| D   | 19.00/70 | 19.00/60  | 19.15/55 | 19.05/55 | 19.15/55 | 19.00/60 | 18.45/60 |
| S   | —        | —         | —        | —        | 23.20/20 | 23.35/20 | 22.10/15 |

S1-S7: number of scenarios.
Dur: meal duration.
B: breakfast,
L: lunch,
D: dinner,
S: snack (the values are shown as time/amount of given carbohydrates)

Figure 16:
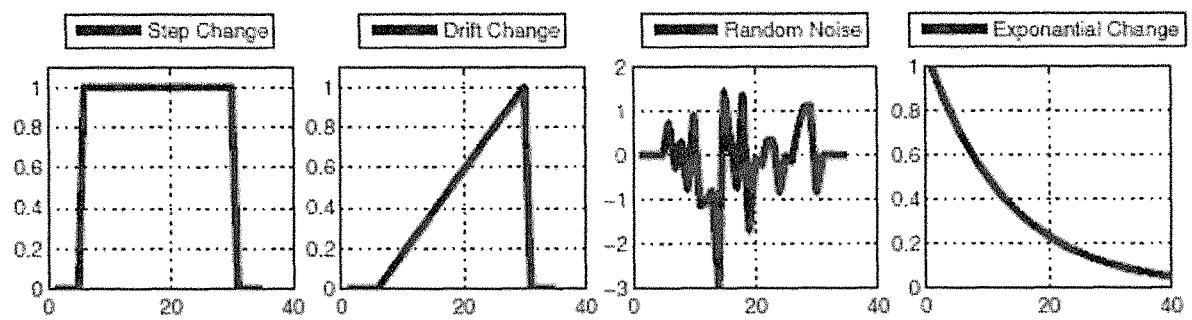
FIG. 16 illustrates different fault types during testing of examples of the invention.

Seven different idealized types of faults such as positive/negative step, positive/negative drift, random noise and positive/negative exponential changes are generated (FIG. 16). Real faults would be combinations of these generic shapes. Each fault is performed for 12 samples (60 minutes). To be more realistic, instead of performing constant/pre-defined fault amplitudes, the amplitudes of faults were defined as fault/signal ratio. The faults were defined as:

$$f_{step} = \begin{cases} \pm \%, & \forall \in [k_f, k_l] \\ 0, & \text{otherwise} \end{cases} \quad (72)$$

$$f_{drift} = \begin{cases} \pm \% \times (k - k_f + 1), & \forall \in [k_f, k_l] \\ 0, & \text{otherwise} \end{cases} \quad (73)$$

$$f_{random} = \begin{cases} \text{var} \times U([0, 1]), & \forall \in [k_f, k_l] \\ 0, & \text{otherwise} \end{cases} \quad (74)$$

$$f_{exponential} = \begin{cases} \pm \% \times \left[1 - e^{\frac{-(k-k_f+1)}{\tau}}\right], & \forall \in [k_f, k_l] \\ 0, & \text{otherwise} \end{cases} \quad (75)$$

where $k_f$ and $k_l$ are the first and last samples of fault intervals and $U([0, 1])$ and var show a uniformly distributed random-number and variance amount respectively, $\tau$ in Eq. (75) defines the speed of the exponential function and is set to 5 minutes in this study.

A fault detection was considered true positive (TP) if it happens inside the 60-minutes interval, of faults and continues at least for 3 samples (15 minutes). A false positive (FP) region was defined as the region where the faults are detected outside of the true positive region (earlier than or after 60-minutes interval). A detection is considered false negative (FN) if it is not raised inside the true positive region (60-minutes interval of fault). The detection time (DT) is defined as the time difference between the start of fault and the first TP detection. The sensitivity (S) and false detection ratio (FDR) are defined:

$$S = \frac{TP}{TP + FN} \quad (76)$$

-continued $$FDR = \frac{FP}{TP + FP} \quad (77)$$

Figure 17:
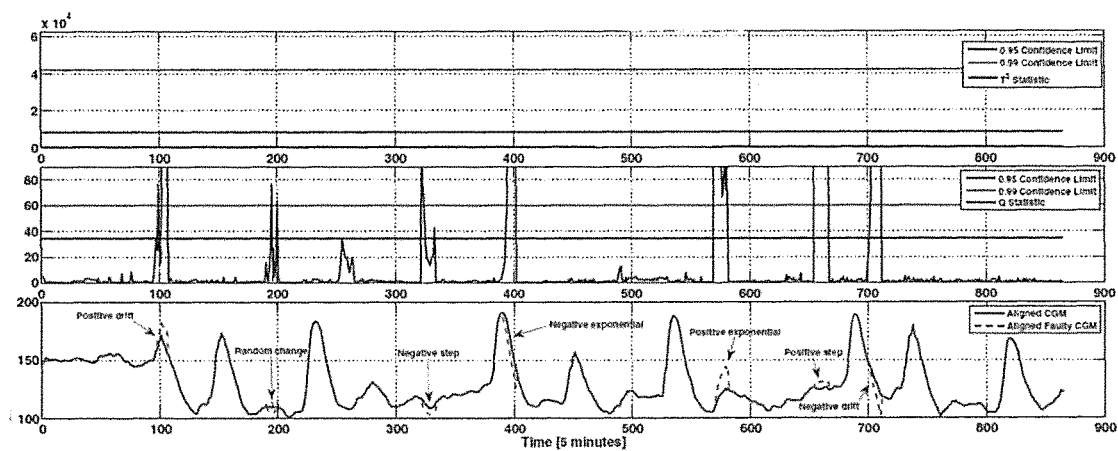
FIG. 17 summarises fault detection during testing of examples of the invention.

FIG. 17 shows the results of one testing data where all defined faults were performed at different times. Based on the criterion in Eq. (71), the number of principal components was found to be 26 which explains 96.9869% the variation of the reference data. Two different confidence interval (0.95 and 0.99) were used for visualization purposes but only the 0.95 confidence interval is used for fault detection. Overall, all faults are detected based on SPE chart which explained that the reference model cannot explain the dynamics of faults. During the peak time of the first breakfast adrift change was given with %=1 for one hour. The fault was detected within 3 sample (15 minutes) delay period. Around 200 samples a random change with 5 mg/dl variance is introduced. After 4 samples the first detection was seen and the SPE chart makes fluctuation due to variations in the fault. During the second night period, the original CGM data makes a sudden drop and this drop is amplified with a negative step change (%=5). The negative step change was detected without any delay. To simulate the sudden drops in COM measurement after meal peaks, a negative exponential (%=10) fault was given, during the last half of the second breakfast. The fault was successfully detected in 15 minutes. Another exponential fault (positive %=20) was performed during the late snack, time of the second night and is detected in 5 minutes. The next fault (positive step %=5) was used to simulate the non-realistic sudden change in CGM measurements during night periods when there is no meal (or significant insulin infusion). The fault was detected as soon as it is introduced. The last fault, was given to mimic fast decrease in CGM data when, glucose levels are relatively close to hypoglycemia region. For this case, a drift fault with %=1 was tested during lower glucose levels after the third breakfast. The drift fault was detected within 10 minutes delay. The results of FIG. 15 demonstrate that the method was able to detect all given faults within acceptable ranges of detection delay.

For the sensitivity analysis of the proposed method, more randomized cases were generated, for each of the 7 types of faults, 20 different fault/signal (%) ratio or variance (var) values were defined. For each % (or var) value 10 different faults were introduced. Testing datasets were randomly selected from fifty different three-day simulations of the seventh scenario. The times of fault introduction were also randomly selected for each % (or var) value and fault type.

Table IX shows the sensitivity analysis of the proposed method for positive and negative step faults that were defined based on various amplitudes. As expected for lower % values the S value was close to 0 which means that the faults were not detected. In fact, this is a desired behavior, since such small changes in CGM measurements are normal and were inside the acceptable range. The strength of the fault detection algorithm is seen when relatively higher % values are used. The sensitivity is above 90% while no false detection was observed. The detection time is between a range of 10-15 minutes which was considered to be acceptable.

TABLE IX

| % | Positive Step Change | | | | Negative Step Change | | | |
|---|---|---|---|---|---|---|---|---|
|   | Av. Med. | S | FDR | DT | Av. Med. | S | FDR | DT |
| 1  | 1.20  | 0.00 | —    | —    | −1.18  | 0.00 | —    | —    |
| 2  | 2.73  | 0.70 | 0.00 | 6.57 | −2.56  | 0.50 | 0.00 | 3.80 |
| 3  | 3.89  | 0.50 | 0.00 | 4.40 | −3.63  | 0.70 | 0.00 | 4.00 |
| 4  | 4.73  | 0.80 | 0.00 | 6.38 | −5.17  | 0.90 | 0.00 | 3.44 |
| 5  | 5.95  | 0.90 | 0.00 | 3.00 | −6.38  | 0.90 | 0.00 | 4.22 |
| 6  | 7.45  | 0.90 | 0.00 | 3.33 | −7.81  | 0.80 | 0.00 | 4.00 |
| 7  | 8.59  | 1.00 | 0.00 | 2.60 | −9.84  | 1.00 | 0.00 | 2.20 |
| 8  | 10.91 | 1.00 | 0.00 | 5.00 | −11.34 | 1.00 | 0.00 | 2.60 |
| 9  | 11.00 | 1.00 | 0.00 | 2.00 | −12.41 | 0.90 | 0.00 | 3.67 |
| 10 | 13.13 | 1.00 | 0.00 | 3.30 | −12.08 | 1.00 | 0.00 | 2.70 |
| 11 | 13.88 | 0.90 | 0.00 | 3.11 | −14.65 | 0.90 | 0.00 | 3.33 |
| 12 | 15.71 | 0.90 | 0.00 | 2.78 | −16.30 | 1.00 | 0.00 | 2.00 |
| 13 | 16.30 | 1.00 | 0.00 | 2.00 | −16.60 | 1.00 | 0.00 | 2.00 |
| 14 | 20.56 | 1.00 | 0.00 | 2.90 | −18.71 | 1.00 | 0.00 | 2.10 |
| 15 | 19.25 | 1.00 | 0.00 | 2.00 | −19.05 | 1.00 | 0.00 | 2.80 |
| 16 | 22.29 | 1.00 | 0.00 | 2.70 | −20.95 | 1.00 | 0.00 | 2.00 |
| 17 | 20.77 | 1.00 | 0.00 | 2.00 | −22.37 | 1.00 | 0.00 | 2.00 |
| 18 | 22.47 | 1.00 | 0.00 | 2.00 | −22.00 | 1.00 | 0.00 | 2.00 |
| 19 | 23.21 | 1.00 | 0.00 | 2.70 | −23.88 | 1.00 | 0.00 | 2.00 |
| 20 | 28.49 | 1.00 | 0.00 | 2.10 | −27.48 | 1.00 | 0.00 | 2.00 |

%: Fault/signal ratio,
Av. Med.: Average of median of different faults,
S: Sensitivity,
FDR: False detection ratio,
DT: Detection time [samples]

The % values are kept lower for the drift (Table X) and exponential (Table XI) types of changes since the faults themselves had an increasing (in both directions) amplitude. Compared to step changes, the drift and exponential changes had longer detection time (10-20 minutes). There is no wrong fault detection for any of the cases. However there were some missed faults when smaller values for % are used.

TABLE X

| % | Positive Drift Change | | | | Negative Drift Change | | | |
|---|---|---|---|---|---|---|---|---|
|   | Av. Med. | S | FDR | DT | Av. Med. | S | FDR | DT |
| 0.1 | 0.93  | 0.00 | —    | —    | −0.79  | 0.00 | —    | —    |
| 0.2 | 1.54  | 0.20 | 0.00 | 7.00 | −1.69  | 0.30 | 0.00 | 9.00 |
| 0.3 | 2.43  | 0.20 | 0.00 | 8.50 | −2.48  | 0.70 | 0.00 | 7.43 |
| 0.4 | 3.10  | 0.50 | 0.00 | 5.80 | −3.58  | 0.80 | 0.00 | 6.38 |
| 0.5 | 4.08  | 0.70 | 0.00 | 7.86 | −4.10  | 0.70 | 0.00 | 7.71 |
| 0.6 | 5.13  | 0.50 | 0.00 | 5.40 | −4.96  | 0.90 | 0.00 | 5.22 |
| 0.7 | 5.48  | 0.90 | 0.00 | 5.44 | −5.80  | 0.70 | 0.00 | 6.00 |
| 0.8 | 6.81  | 0.90 | 0.00 | 6.33 | −6.82  | 1.00 | 0.00 | 6.00 |

TABLE X-continued

| % | Positive Drift Change | | | | Negative Drift Change | | | |
|---|---|---|---|---|---|---|---|---|
|   | Av. Med. | S | FDR | DT | Av. Med. | S | FDR | DT |
| 0.9 | 7.14  | 0.80 | 0.00 | 4.00 | −7.12  | 0.90 | 0.00 | 4.78 |
| 1.0 | 8.72  | 1.00 | 0.00 | 5.70 | −7.84  | 1.00 | 0.00 | 6.50 |
| 1.1 | 8.80  | 0.80 | 0.00 | 7.00 | −8.99  | 0.80 | 0.00 | 4.75 |
| 1.2 | 9.70  | 1.00 | 0.00 | 5.00 | −9.67  | 1.00 | 0.00 | 3.50 |
| 1.3 | 10.42 | 1.00 | 0.00 | 4.10 | −10.44 | 0.90 | 0.00 | 4.89 |
| 1.4 | 10.96 | 1.00 | 0.00 | 3.70 | −12.23 | 0.90 | 0.00 | 4.67 |
| 1.5 | 13.23 | 0.90 | 0.00 | 4.00 | −12.47 | 1.00 | 0.00 | 5.60 |
| 1.6 | 12.75 | 1.00 | 0.00 | 3.70 | −13.31 | 1.00 | 0.00 | 3.70 |
| 1.7 | 13.70 | 0.90 | 0.00 | 4.33 | −14.00 | 1.00 | 0.00 | 4.80 |
| 1.8 | 15.36 | 1.00 | 0.00 | 4.50 | −15.56 | 1.00 | 0.00 | 4.30 |
| 1.9 | 15.02 | 1.00 | 0.00 | 4.10 | −16.47 | 1.00 | 0.00 | 5.60 |
| 2.0 | 15.45 | 1.00 | 0.00 | 4.00 | −16.30 | 1.00 | 0.00 | 3.80 |

%: Fault/signal ratio,
Av. Med.: Average of median of different faults,
S: Sensitivity,
FDR: False detection ratio,
DT: Detection time [samples]

TABLE XI

| % | Positive Exponential Change | | | | Negative Exponential Change | | | |
|---|---|---|---|---|---|---|---|---|
|   | Av. Med. | S | FDR | DT | Av. Med. | S | FDR | DT |
| 1  | 0.89  | 0.00 | —    | —    | −0.88  | 0.00 | —    | —     |
| 2  | 1.82  | 0.30 | 0.00 | 7.67 | −1.89  | 0.10 | 0.00 | 11.00 |
| 3  | 2.88  | 1.00 | 0.00 | 6.90 | −3.12  | 0.50 | 0.00 | 4.60  |
| 4  | 3.85  | 0.50 | 0.00 | 4.80 | −3.51  | 0.70 | 0.00 | 7.29  |
| 5  | 4.98  | 0.70 | 0.00 | 5.29 | −4.23  | 0.70 | 0.00 | 7.86  |
| 6  | 4.98  | 0.70 | 0.00 | 5.14 | −5.61  | 0.80 | 0.00 | 4.88  |
| 7  | 6.38  | 0.80 | 0.00 | 5.75 | −5.81  | 0.80 | 0.00 | 4.75  |
| 8  | 7.01  | 0.80 | 0.00 | 6.38 | −6.83  | 0.70 | 0.00 | 4.86  |
| 9  | 9.34  | 1.00 | 0.00 | 4.20 | −8.10  | 1.00 | 0.00 | 4.80  |
| 10 | 8.44  | 0.90 | 0.00 | 5.89 | −8.74  | 0.90 | 0.00 | 3.00  |
| 11 | 10.13 | 1.00 | 0.00 | 4.70 | −9.93  | 1.00 | 0.00 | 4.60  |
| 12 | 10.77 | 1.00 | 0.00 | 4.50 | −11.26 | 1.00 | 0.00 | 3.40  |
| 13 | 13.54 | 0.90 | 0.00 | 3.00 | −11.95 | 0.90 | 0.00 | 4.89  |
| 14 | 12.84 | 0.80 | 0.00 | 2.50 | −13.38 | 1.00 | 0.00 | 3.30  |
| 15 | 13.32 | 1.00 | 0.00 | 3.70 | −14.67 | 1.00 | 0.00 | 2.70  |
| 16 | 14.07 | 0.90 | 0.00 | 3.22 | −14.18 | 1.00 | 0.00 | 3.40  |
| 17 | 15.14 | 1.00 | 0.00 | 2.70 | −15.41 | 1.0  | 0.00 | 3.00  |
| 18 | 16.74 | 1.00 | 0.00 | 2.90 | −16.26 | 1.00 | 0.00 | 2.70  |
| 19 | 18.64 | 1.00 | 0.00 | 2.60 | −17.46 | 1.00 | 0.00 | 2.80  |
| 20 | 18.03 | 1.00 | 0.00 | 2.70 | −19.51 | 1.00 | 0.00 | 2.90  |

%: Fault/signal ratio,
Av. Med.: Average of median of different faults,
S: Sensitivity,
FDR: False detection ratio,
DT: Detection time [samples]

The last fault type was defined to be random changes based on a variance (var) value. Time to detection is longer because the random variations may prevent three consecutive samples to exceed the limits. Thus even though the readings may be above the threshold for one or two samples, they were not considered as true positive detections.

Multiway principal component analysis is thus useful in embodiments of this invention for detection of CGM related faults using data generated from the UVa/Padova simulator. The proposed method and module are able to detect all types of faults with very high accuracy without need of any information from the system that is under surveillance.

TABLE XII

| var | Av. Med. | S | FDR | DT |
|---|---|---|---|---|
| | | Random Change | | |
| 1 | 0.27 | 0.00 | — | — |
| 2 | −0.12 | 0.10 | 0.00 | 5.00 |
| 3 | −0.44 | 0.10 | 0.00 | 2.00 |
| 4 | 0.28 | 0.30 | 0.00 | 7.67 |
| 5 | 0.96 | 0.40 | 0.00 | 6.50 |
| 6 | 0.82 | 0.90 | 0.00 | 7.11 |
| 7 | 0.07 | 0.60 | 0.00 | 6.83 |
| 8 | 0.27 | 0.50 | 0.00 | 9.20 |
| 9 | 0.40 | 0.90 | 0.00 | 6.89 |
| 10 | −1.65 | 0.90 | 0.00 | 6.00 |
| 11 | −0.59 | 0.80 | 0.00 | 7.88 |
| 12 | 1.15 | 0.90 | 0.00 | 3.89 |
| 13 | −0.67 | 0.90 | 0.00 | 5.56 |
| 14 | −2.16 | 0.90 | 0.00 | 5.22 |
| 15 | 1.74 | 1.00 | 0.00 | 6.40 |
| 16 | 0.95 | 0.80 | 0.00 | 7.88 |
| 17 | −1.64 | 0.90 | 0.00 | 5.33 |
| 18 | 1.01 | 0.90 | 0.00 | 6.11 |
| 19 | 0.65 | 0.90 | 0.00 | 7.33 |
| 20 | −0.99 | 0.90 | 0.00 | 5.67 | var: variance, Av. Med.: Average of median of different faults, S: Sensitivity, FDR: False detection ratio, DT: Detection time [samples]

Multivariate Statistical Batch Monitoring

Since an artificial pancreas (AP) system uses several components such as sensors, transmitters, receivers, control units and pumps, it is prone to equipment failures. A sudden increase in continuous glucose monitoring (CGM) value due to sensor error may cause an AP system to over-dose which may cause hypoglycemia, and a blockage in the infusion set may cause hyperglycemia. There are no AP systems that have a fault (failure) detection and diagnosis module which can monitor the AP system for possible equipment failures.

Statistical, process monitoring (SPM) and quality control have been very important in manufacturing industries and several techniques ranging from Shewhart charts to advanced multivariate SPM methods have been used successfully. Multivariate SPM techniques have gained importance in recent years and powerful multivariate SPM techniques for continuous and batch processes have been developed. Multivariate SPM charts provide more accurate information, about the system state, give warnings earlier than the univariate charts.

In some embodiments of this invention, a fault detection and diagnosis method for an artificial pancreas systems frames the problem as a batch process monitoring problem where the period following a meals is defined as a batch. In embodiments of this invention the batch period is a predetermined time period, such as 24 hours. This period, starts with the consumption of a meal which is a major disturbance to glucose homeostasis. It causes a sharp rise in blood glucose concentration (BGC) that tapers off slowly to a steady value. Since meals may contain different amounts of carbohydrates, protein and fat, the maximum BGC and the time to reach a steady BGC will be different for various meals. Other confounding activities such as physical activity and stress (both affect the sensitivity to insulin) may also occur during this batch period. Consequently, it is necessary to align batches to be used for developing the reference that describes normal operation to capture how the body responds to food when she artificial pancreas is functioning without faults that cause significant deviations in BGC. A strength of the multivariate SPM approach is to leverage the information, collected from various sensors to compute statistics that indicate abnormal operation of an AP and to determine the variables that caused significant-variation in these statistics. Then, rules are used to relate these variables to the source causes of the abnormal operation and diagnose the faults. This multivariate SPM approach can also be used to detect the presence of physical activity or stress, and determine the type and intensity of physical activity.

Multivariate SPM relies on the statistical distance concept. When there is significant colinearity in data, multivariate SPM charts based on principal components (PC) or latent variables (LV) of partial least square (PLS) are used to compute statistical distances from the reference state to summarize the information about the status of the system by using two statistics, the Hotelling's $T^2$ ($T^2$) and the squared prediction error (SPE). The monitoring charts are the plots of $T^2$ and SPE values computed by using information collected at each sampling time on the time axis. The $T^2$ chart indicates the distance of the current operation from the desired state as captured by the PCs or LVs included in the development of the model. Since only the first few PCs or LVs that capture most of the variation in the data are used to build the model, the model is an accurate but incomplete description of the process. The SPE chart captures the magnitude of the error caused by deviations resulting from events that are not described by the model. The $T^2$ and SPE charts are desirably used as a pair and if either chart indicates a significant deviation from the reference state, the presence of an abnormal situation is declared.

Principal component analysis (PCA) involves the orthogonal decomposition of the set of process measurements along the directions that explain the maximum variation in the data, PCA method can be used either as a filtering tool, for efficient data analysis and visualisation or as a model-building structure to describe the expected variation under normal operation (NO). For a particular process, a NO data set covers targeted operating conditions during satisfactory performance. The PCA model that is based on NO conditions can be used to detect outliers, unusual patterns and deviations from NO conditions.

For continuous process, the data can be represented by matrix X(n×m) where n is the number of measurements and m the number of variables. The directions extracted by the orthogonal decomposition of X are the eigenvectors $p_i$(m×1) of $X^TX$ also called PC loadings:

$$X = t_1 p_1^T + t_2 p_2^T + \ldots + t_r p_r^T + E \quad (78)$$

where E(n×m) is the residuals matrix and superscript T denotes mains transpose. The dimension r is chosen such that most of the significant process information is captured by the $t_i\, p_i^T$ terms, and E contains mostly random error. The projection of the measurements onto the eigenvectors defines new points in the measurement space that constitute the score matrix T whose columns are $t_i$(n×1) (Eq. (62)). The relationship between T, P, and X can also be expressed as:

$$T = X P \text{ and } X = TP^T + E \quad (79)$$

where P is the m×r matrix of loadings and T is the n×r score matrix. PCA transforms the coordinate system of a data set for more efficient description of variability in data.

Figure 18:
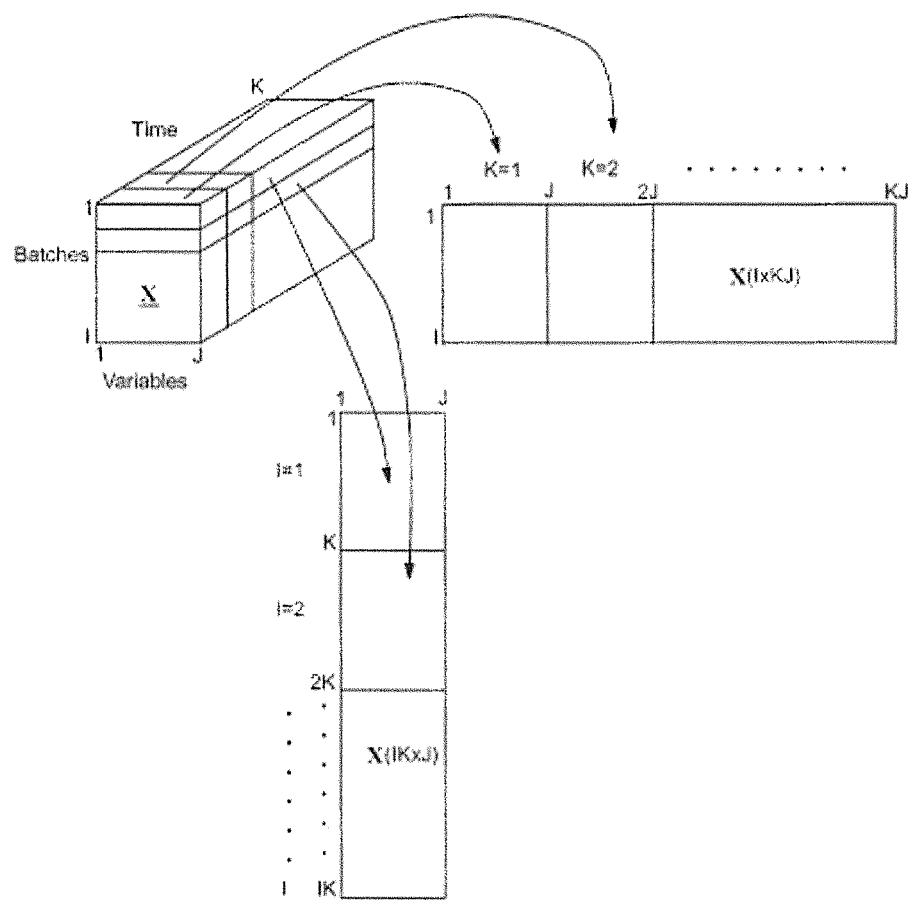
FIG. 18 illustrates a mathematical unfolding technique according to one embodiment of this invention.

Even though the human body can be considered as a continuous batch, the changes in glucose profile occur in a batch format. In batch processes, the data from experimental studies takes the form of three-way matrix. A batch is run in which j−1, 2, . . . , J variables are measured at k=1, 2, . . . , K time intervals through the batch. Similar data exists on a number of i=1, 2, . . . , I repeated batches. Hence, the batch data composes a 3-D matrix X̲(I×J×K) as illustrated in FIG. 18, The different batches are arranged along the vertical axis, the measurement variables across the horizontal axis, and their observations go through the third dimension. Each horizontal slice of X̲ matrix is a J×K matrix containing the trajectories of all the variables from a single batch i, while each vertical slice is a I×J matrix presenting the values of all the variables for all different batches at an observed time interval k.

Multiway principal component analysis (MPCA) has been applied to many application for fault detection purposes of batch processes where data compose three-dimensions matrix. MPCA is equivalent to performing ordinary PCA on a large two-dimensional matrix X constructed by unfolding the three-dimensional matrix X̲. The very common two unfolding ways are shown in FIG. 18. When the X̲ is unfolded into the X(I×k J) matrix by adding vertical slices (I×J) side X(I×KJ) matrix by adding vertical slices (I×J) side by side to the right, the data variability among the batches in X̲ can be analyzed with respect, to variables and their observation time intervals. This is the most suitable unfolding technique for SPM purposes. However, it requires all bathes to be of equal length and completed. The second unfolding is performed by adding vertical (I×J) slices which provides the variance information along all batches and time. There is no need for batches to be completed or to be of equal length. However, after mean centering step, it leaves the nonlinear time-varying trajectories in the data matrix because it simply subtract a constant, the grand mean of each variable over ail batches and time, from the trajectory of each variable. Hence, the results may be weak for small disturbances when the goal is to cheek deviations from the mean trajectory.

The X̲ matrix can be decomposed to summation of the product of score vectors $t_r$ (I×1) and loadings matrix PR (J×K) and a residual E̲:

$$X = \sum_{r=1}^{R} t_r \otimes P_r + E \quad (80)$$

or $$X = \sum_{r=1}^{R} t_r P_r^T + E = X + E$$

where ⊗ denotes the Kronecker product such that X̲=⊗, P=X̲(i, j, k)=t(i)P(j, k), and R is the number of PCs. Considering the first unfolding technique, the second equation in Eq. (64) can also be used, where $t_r$(I×1) and $p_r$(KJ×1) are the score and loading vectors of the unfolded X(I×KJ) matrix (FIG. 18).

The data matrix X is mean-centered and usually scaled to unit variance if the variables are not already in the same scale before performing PCA in the preprocessing step. For doing that, the mean of each column in X is subtracted from each column and divide my standard deviation of the columns.

The PCs for PCA can be computed by spectral decomposition or singular value decomposition. The covariance matrix $$\tilde{S} = \frac{X^T \tilde{X}}{m-1}$$

can be decomposed by spectral decomposition as:

$$S = P \Lambda P^T \quad (81)$$

where P is a unitary matrix whose columns are the normalized eigenvectors of the S matrix and Λ is a diagonal matrix that contains the ordered eigenvalues $\lambda_i$ of the S. The scores T is then calculated by T=X̃ P.

Singular value decomposition of the X matrix is given as:

$$X = U \Sigma V^T \quad (82)$$

where the columns U are of the normalized eigenvectors of $XX^T$, the columns of V are the normalized eigenvectors of $X^TX$, and Σ is a diagonal matrix having as its elements the singular values, or the positive square roots of the magnitude ordered eigenvalues of $X^TX$. The loading and score matrices are obtained as:

$$P = V \text{ and } T = U\Sigma \quad (83)$$

In this example, the nonlinear iterative partial least square (NIPALS) method that was developed by Wold et al., "Principal component analysis," *Chemometrics and intelligent laboratory systems*, vol. 2, no. 1, pp. 37-52, 1987, was used for the calculation of PC's because the decomposition methods were inefficient for calculation of PCs when number of the PCs is largely smaller than the number of variables which is a very common condition when the X̲ matrix is batch wise (first method) unfolded. The NIPALS algorithm for MPCA:

1) Unfold X̲(I×J×K) into X(I×J K).
2) Scale X.
3) Choose a column of X as t.
4) p=X T t.
5) p=p/\p\.
6) t=X p.
7) If t has converged, then go to Step 8; otherwise go to Step 4.
8) E=X−tpT.
9) Go to Step 4 with X=E to extract the principal component.

Again, even though the human body can be considered as a continuous batch, the changes in glucose profile occur in a batch format. After a meal, glucose levels increase to a higher and comes does when insulin is infused. This is up and down curve shape is repeated for every meals. By defining each meal period as a batch, the batch wise unfolding technique is used herein.

Once the scores and loadings for the unfolded matrix X are obtained from the NIPALS algorithm, $T^2$ and SPE can be used for fault detection. The $T^2$ chart detects the small shifts and deviations of new observations from the NO conditions that are captured by the MPCA model. It includes contributions of ail variables which can be significantly faster than checking the deviation of individual variables. The $T^2$ for all variables in a batch at time k based on the reference data X̲ is calculated:

$$T_{i,k}^2 = \sum_{j=1}^{J} (t_{i,j,k} - \bar{t}_{j,k}) \Lambda^{-1} (t_{i,j,k} - \bar{t}_{j,k})^T \frac{I(I-R)}{R(I^2-1)} \quad (84)$$

where $t_{i,j,k}$(1×R) is the score vector of the batch i for variable j at time k and $\bar{t}_{j,k}$ (1×R) is the mean of the scores matrix $T_k$(I×R). The diagonal matrix Λ(R×R) is derived during the iterations of the NIPALS algorithm (Step 6) whose diagonal element are calculated as the variance of each converged score vector. The control limit for $T^2$ at time k is defined as:

$$\bar{T}_k^2 = \bar{t}_k \pm 3\sigma_{T_k} \quad (85)$$

where $\sigma_{T_k}$ is the standard deviation of $T_k$ matrix for I batches at time k.

SPE charts show deviations from the NO conditions that are not captured by the MFC A model. The SPE for all variables in a batch at time k based on the reference data $\underline{X}$ is calculated;

$$SPE_{i,k} = \sum_{j=1}^{J} (x_{i,j,k} - \hat{x}_{i,j,k})^2 \tag{86}$$

where $x_{i,j,k}$ is a variable j from batch i at time k and $\hat{x}_{i,j,k}$ is the predicted value of the same variable that is obtained from the Eq. (78). The control limit for SPE at time k is defined as:

$$\widetilde{SPE}_k = \overline{SPE}_k \pm 3\sigma_{SPE_k} \tag{87}$$

where $\overline{SPE}_k$ and $\sigma_{SPE_k}$ are the mean and standard deviations of the $SPE_k$ (1×1), respectively.

In real-time, when a new set of data (J variables) from a new batch is measured at time k, the terms $t_{i,j,k}$ and $x_{i,j,k}$ in Eq. (68) and (69) are replaced with $t_{new,j,k}$ and $x_{new,j,k}$, respectively. A fault is detected if any of the following condition is satisfied:

$$T_k^2 \le T_{new,k}^2 \text{ or } \widetilde{SPE}_k \le SPE_{new,k} \tag{88}$$

In Eq. (88) only, the positive side of limits is considered because both $T^2$ and SPE values are always positive due to squared calculation in Eq. (84) and (85).

It is a common situation in batch processes that the total, duration of the batches is not the same due to several factor. The unequal, batch data length causes problems for defining a 3D $\underline{X}$ for development of an MPCA model. Even though the batches have same length, due to dynamic variability, different event may occur at different times from batch to batch. This kind of mismatching in data may cause wrong and missed alarms in a MPCA based, fault detection algorithm. As mentioned before, the time interval between two meals is defined as a batch. Batch wise unfolded MPCA models require equal batch length. However, different types and/or amounts of meals may not have the same effect which may results various different lengths and shapes of glucose profile. Due to the human body complexity, the duration of two identical meals may not be the same.

Dynamic time warping (DTW) has its origins in speech recognition and is a flexible, deterministic, pattern matching scheme that works with pairs of patterns. It can locally translate, compress, and expand the patterns so that similar features in the patterns are matched. DTW nonlinearly warps two trajectories in such a way that similar events are aligned and a minimum distance between them is obtained. It is assumed that an appropriate scaling was performed prior to implementation of DTW; scaling is an important issue since DTW is a distance-based technique. One can calculate the mean and standard deviation for each variable in each batch trajectory set, take the average of those, and use the average to scale the set of trajectories to a common y-axis scale. The reference batch trajectory set is defined based on process knowledge, or it can be calculated based on an adaptive iteration technique. No scaling is performed in this thesis, since the batch synchronization is done only based on CGM measurements.

Assume that $x_r$ and $x_t$ are the reference batch trajectory (previously defined) and a batch to be synchronized with size r and t, respectively. DTW, discussed above, defines the Euclidean distance between each point of the two trajectories as:

$$d(i(\kappa), j(\kappa)) = [x_r(i(\kappa)) - x_t(j(\kappa))][x_r(i(\kappa)) - x_t(j(\kappa))]^T \tag{89}$$

where $\kappa$ is the number of grid points along the path between two trajectories, i, j are the sample points and goes up to r and t for the reference and new batch trajectories, respectively. The total distance between two batch trajectories is:

$$D(r, t) = \sum_{n=1}^{L} d(i(\kappa), j(\kappa)) \tag{90}$$

where max(t, r)≤L≤r+t. The optimal path and minimum total distance is found as the solution of the following optimization problem:

$$D^*(r, t) = \min_F D(r, t) \text{ or } F^* = \min_F D(r, t) \tag{91}$$

The Computational load to solve the problem, in Eq. (91) might, be too high, since all possible paths must be defined and the one which gives minimum distance is selected. A very elegant and effectively solution to this problem is dynamic programming. Dynamic programming is a mathematical technique which guarantees to find the optimum path without having to calculate the distance along all possible paths:

$$D_F(i, j) = \min \begin{cases} D_F(i-1, j) + d(i, j) \\ D_F(i-1, j-1) + d(i, j) \\ D_F(i, j-1) + d(i, j) \end{cases} \tag{92}$$

With respect to some local and global constraints:

$$D_F(r,t) \le d(r,t)$$

$$D_F(1,1) = d(1,1)$$

$$i(\kappa+1) \ge i(\kappa)$$

$$j(\kappa+1) \ge j(\kappa) \tag{93}$$

Figure 19:
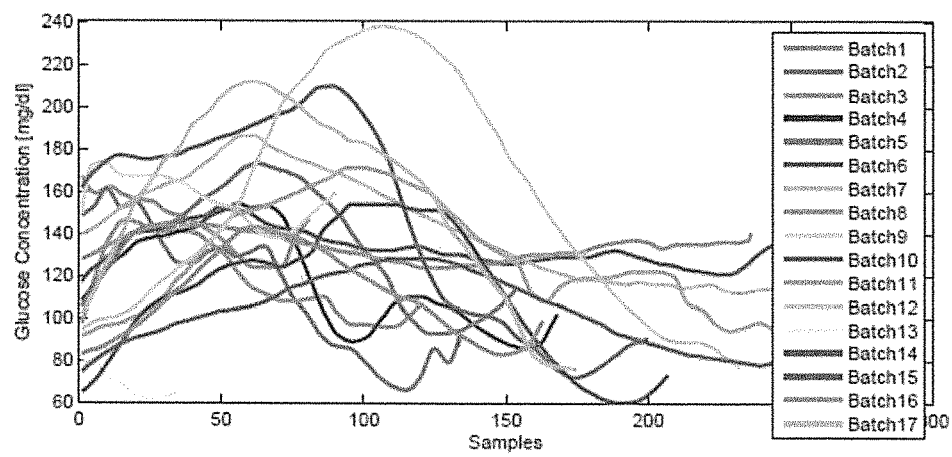
FIG. 19 includes graphs produced during testing of examples of the invention.
Figure 19:
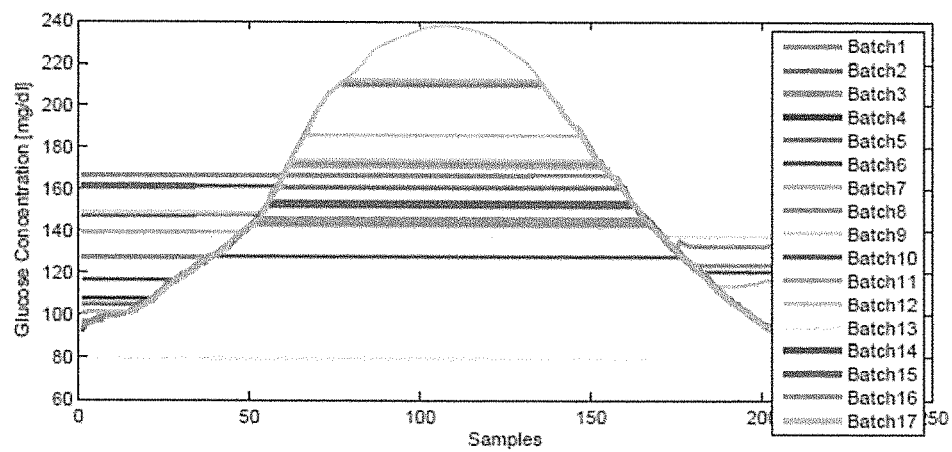

FIG. 19 shows an example of DTW synchronization. The top figure shows 17 different glucose profile trajectories. In addition to unequal lengths the profiles are also different from each other. The bottom figures show the synchronized batch trajectories after applying the DTW algorithm. All glucose trajectories are aligned based on a reference batch (Batch 12) such that they have same length and similar profiles. In case, if the synchronized batch is shorter than the reference batch, the DTW fills the synchronized signal from the point that similarity goes away until the point again a similarity is found.

After a fault is detected by either the $T^2$ or SPE charts as in the Eq. (88), the source of the fault most be defined. In this thesis, whenever a fault is detected, the contribution of all variables on the $T^2$ and SPE is calculated. The contributions are sorted in descending order. Based on reference data two threshold are defined. The sorted variables that have contributed more than the defined threshold are considered as the source of the detected fault. By checking the determined variables, a fault diagnosis is made based on process knowledge and if/then rules. The contribution of the variable j in a batch i at time k is calculated as:

$$CONT_{T^2_{i,j,k}} = (t_{i,j,k} - \bar{t}_{j,k})\Lambda^{-1}(t_{i,j,k} - \bar{t}_{j,k})^T \quad (94)$$

$$CONT_{SPE_{i,j,k}} = \sum_{j=1}^{J}(x_{i,j,k} - \hat{x}_{i,j,k})^2 \quad (95)$$

Data was collected from 7 subjects using multiple devices. Each subject had a CGM sensor, a pump, a Sensewear armband and a BioHarness™ 3 chestband by Zephyr Technology. Overall 47 variables are defined including CGM measurements, insulin infusions, heart rate, breathing rate, three way accelerations, skin temperature, galvanic skin response, heat flux and more. An MPCA model was developed for each subject. The batches in the MPCA models were defined based on the meal detection algorithm where the time interval between two detected meals is defined as a batch. Dynamic time warping is used for real-time synchronization of unequal batch length. $T^2$ and SPE charts are used for the detection of system failures.

Figure 20:
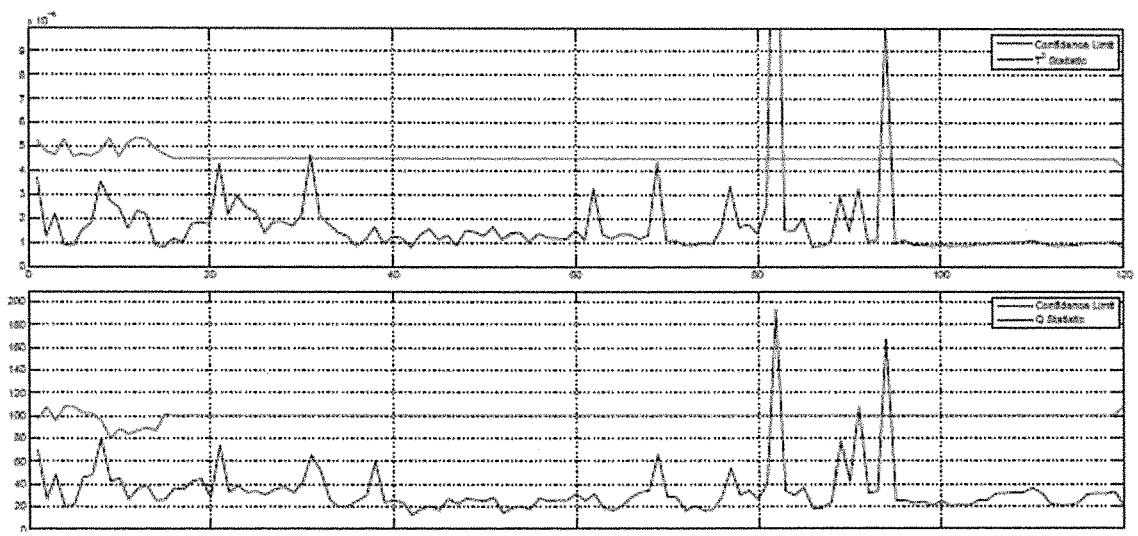
FIGS. 20-29 include charts produced during testing of examples of the invention.

FIG. 20 shows the $T^2$ and SPE charts for a meal batch of a subject. At least one of the charts had values that are above their confidence limits several times which are the indication of system failures. Even though the points that the $T^2$ and SEE are above their threshold, seem to be faults, one should not make a final decision quickly. At these points, the devices might be under NO conditions but none of the similar profiles included in our reference data and thus are considered as faults by the MPCA model. A second alternative is that, they may not be NO conditions but also are not considered as faults by users. Thus, for prevention of wrong fault detection, whenever a fault is detected, a decision is not made based on the last measured sample. The next 5 samples (5 minutes) are observed and the decision is made based on the consistent status of 5 sequential samples.

Figure 21:
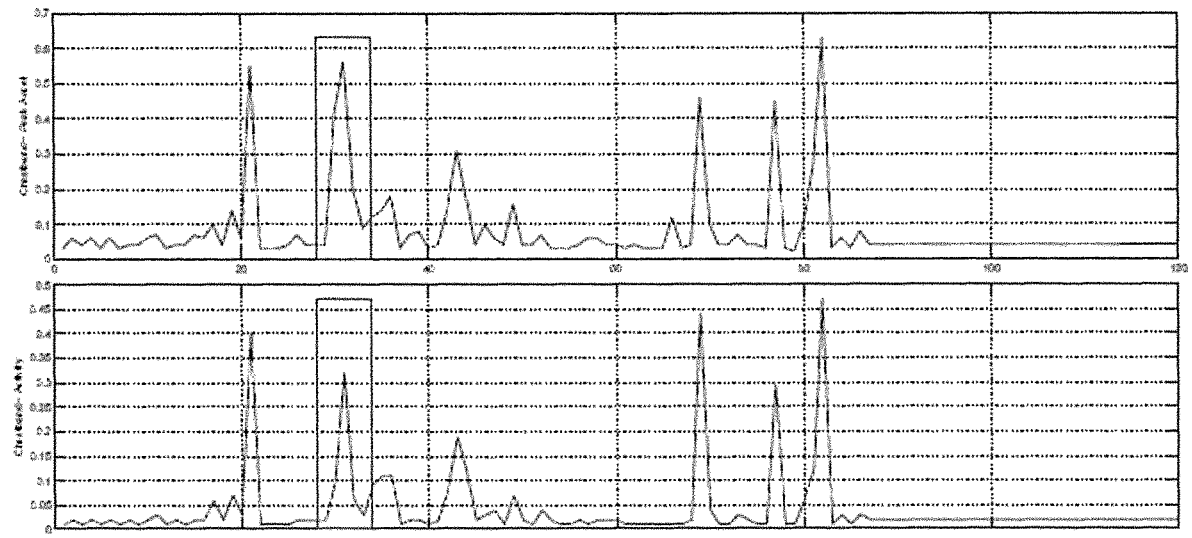

In FIG. 20 the $T^2$ is above its control limit at time 32 for one sample. The variables that contribute the most are determined to be peak acceleration and activity signals from the chestband using the Eq. 88. FIG. 21 shows that both variables make a sudden peak at time 32. It is known that the second variable is a derived variable while the former one is measured directly. The diagnosis of the potential fault is done by checking other related signals from the chestband and the armband at time 32.

Figure 22:
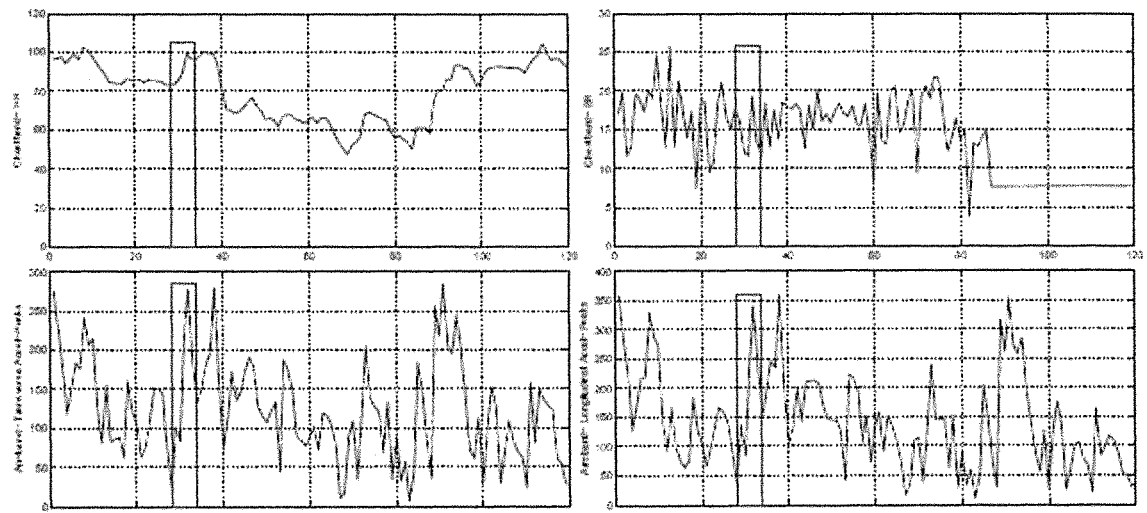

FIG. 22 show four different directly measured variables. These variables are heart rate and breathing rate measured using the chestband and transverse and longitudinal accelerations measured from the armband. The peak in acceleration in the chestband (FIG. 21) signal might be a result of a sudden movement. The same acceleration peak should be seen in the armband acceleration signals as well. When we looked at the two directional acceleration signals of the armband, both signals made an increase at time 32 which is consistent with the peak that observed in FIG. 21. Also the heart rate and the breathing rate signals at time 32 increase, which support the idea that the subject probably had a sudden action which caused an increase in $T^2$ at time 32. Consequently, this sudden change at time 32 was not classified as a fault.

Figure 23:
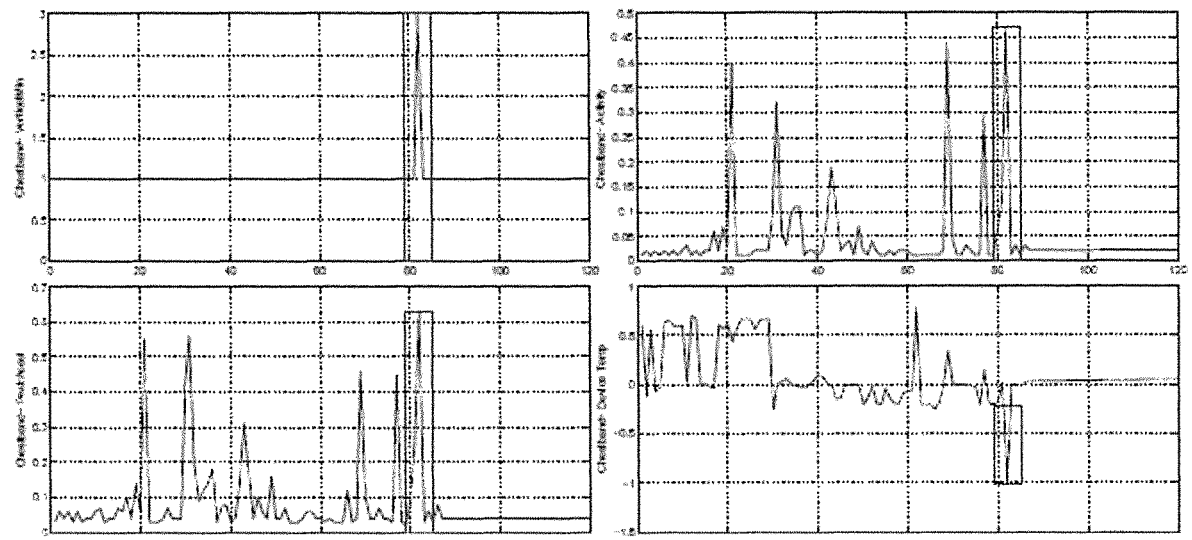
Figure 24:
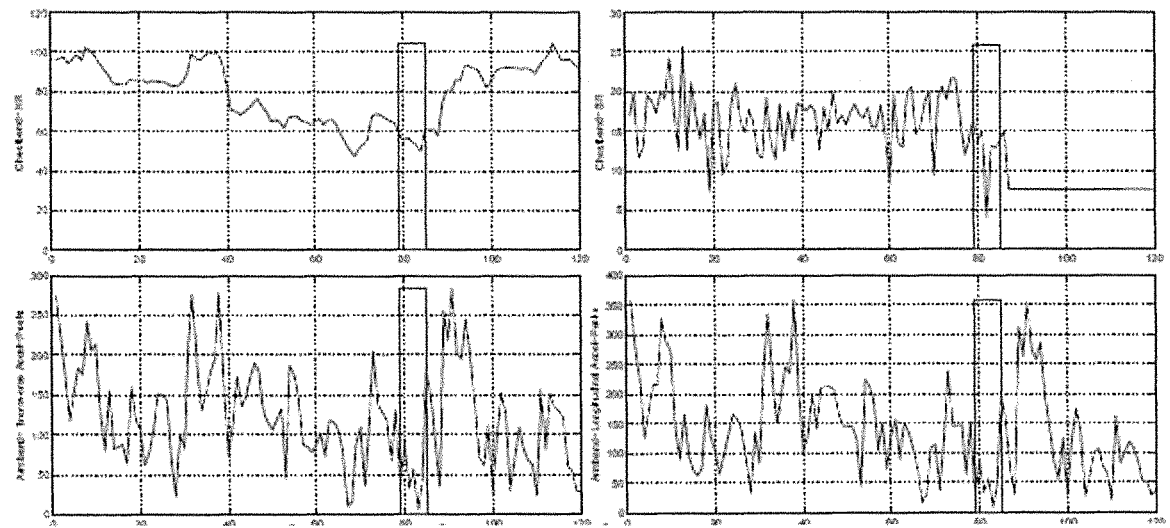

Another fault was detected at time 82 where both $T^2$ and SPE charts are above their thresholds (FIG. 20). The variables that contributed the most to both charts are defined to be vertical minimum, activity, peak acceleration and device temperature signals from the chestband (FIG. 23). Before checking other measured variables in the next 5 samples for a diagnostic decision, but just looking at the vertical minimum and device temperature signals, it can be observed, that the sudden change in the signals is a fault. However, for consistency the other signal must still be checked, FIG. 24 shows heart rate, breathing rate and two way acceleration signals from the chestband and armband, respectively. The transverse and longitudinal acceleration signals showed no acceleration in both directions. Thus, the movement must have been only in the vertical direction, sudden jump could cause this kind of change m the vertical acceleration signal. This was not confirmed with the heart rate and breathing rate signals from the chestband at time 82. A jump that caused peaks in the vertical acceleration and changes in the activity signal must also have significant effect on heart rate and breathing rate as well. After the 5 minutes diagnosis process, the change was defined to be a real fault and the source of the fault was determined as vertical acceleration and device temperature signals.

Figure 25:
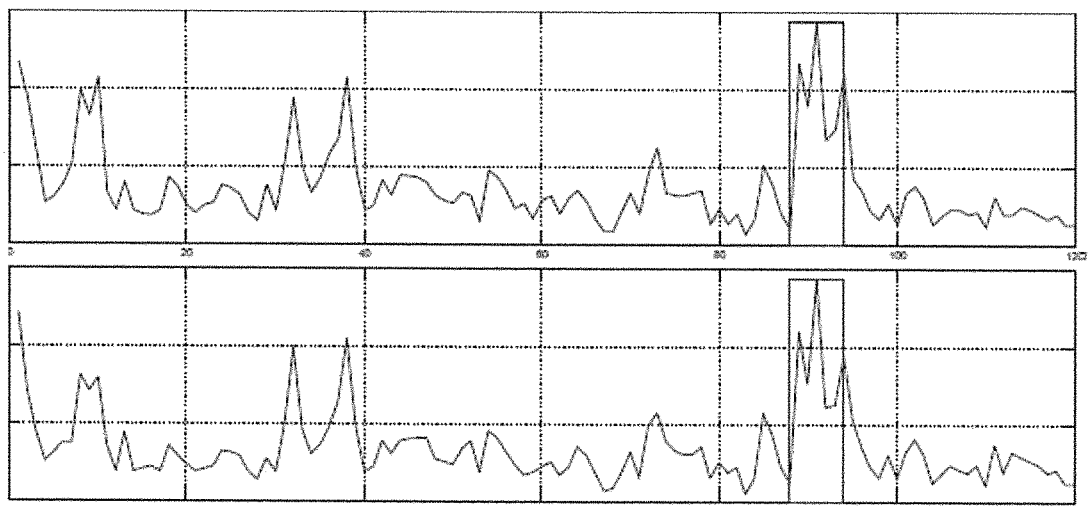
Figure 26:
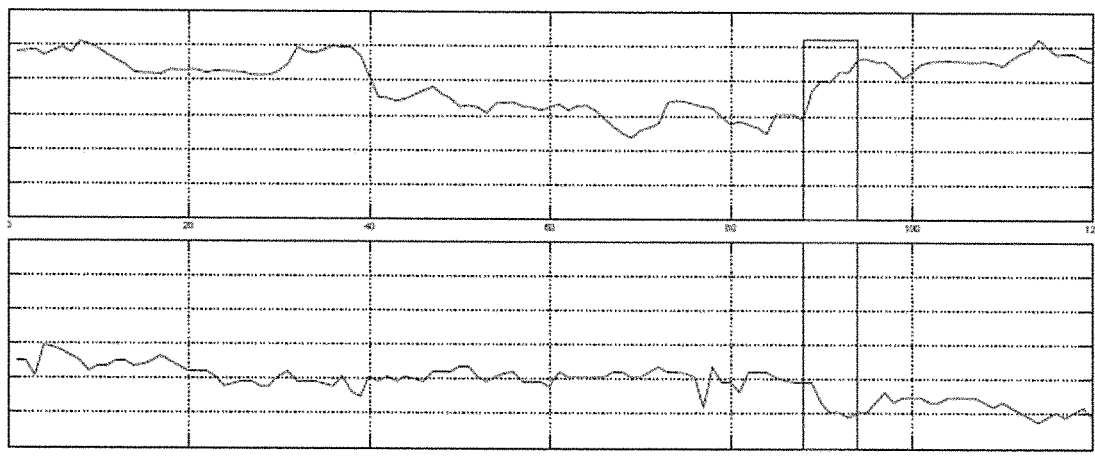

A third fault was detected at time where only the SPE chart is above its threshold. The variables that contributed the most are defined to be the two-way mean absolute difference (MAD) acceleration signals from the armband (FIG. 25). These MAD signals usually change when a person performs exercise for a period of time. The information is confirmed with the two directly measured variables heart rate and galvanic skin response from the chestband and the armband, respectively (FIG. 26). During the 5 minutes of the diagnosis interval, the heart rate signal increased gradually while the galvanic skin response performs a similar behavior in the opposite direction.

The change in the galvanic skin response can be related to sweating during an exercise period. After the diagnosis step, the changes in the MAD accelerations are not defined as a fault but just an exercise period.

Figure 27:
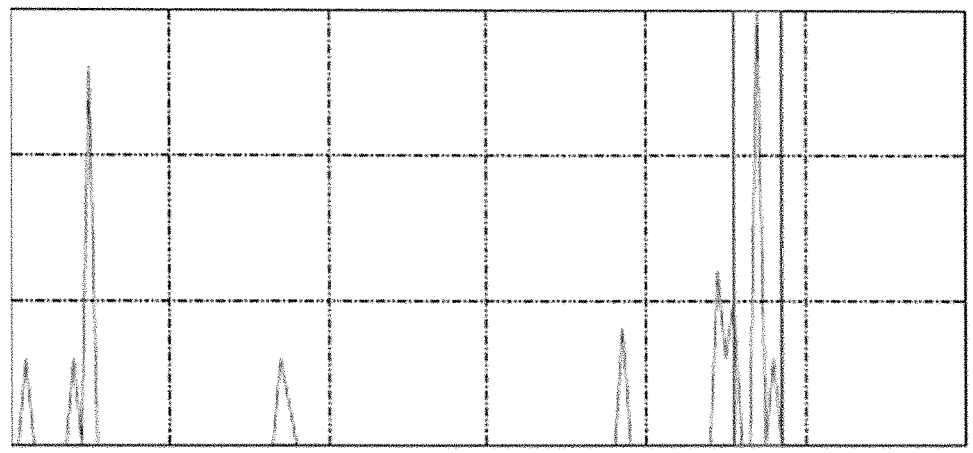

The last fault was detected at time 94 where both charts are above their thresholds. The variables that contributed the most are found to be step counter signal from the armband (FIG. 27). It is seen that 15 steps had been taken in 1 minute. Since, steps were counted in either longitudinal or transverse directions, the peak from 0 to 15 in step counter signal must also be seen in at least one of the peak accelerations. The information was not confirmed with the peak acceleration measurements of the armband, the sudden change in the step counter signal was defined to be a real fault.

Meal Detection of Rapid Glucose Increase and Meals

The invention includes a module for automatically detecting food consumption and/or a rapid glucose level increase without manual input by the patient. In embodiments of this invention, a modified version of the Herman's minimal model is used for meal detection. An unscented Kalman filter (UKF) can be used for simultaneous estimation of states and parameters of the minimal model. Also, meals can be detected based on rate of appearance of glucose estimations and some safety rules. An insulin bolus calculation algorithm, is also added for detected meals.

Bergman's minimal model, is a three-compartment "minimal model" to analyze plasma glucose and insulin dynamics during an intravenous glucose tolerance test. Modifications of the minimal model have been proposed to separate the effect of glucose production from utilization and to capture absorption, distribution, and disposal glucose insulin dynamics. The effects of free fatty acids and exercise are also incorporated into the minimal model. The dynamical equations for plasma glucose concentration G(t) and effective insulin concentration $I_{eff}$ are given by:

$$\frac{dG(t)}{dt} = -p_1 G(t) - p_2 I_{eff}(t) G(t) + p_1 G_b + R_a(t) \quad (96)$$

$$\frac{dI_{eff}(t)}{dt} = -p_2 I_{eff}(t) + p_3 I_p(t) \quad (97)$$

where $G_b$ and $I_p$ represent basal plasma glucose concentration and plasma insulin concentration, respectively. The rate of appearance of glucose $R_a(t)$ can be defined, as a two-compartment model:

$$R_a(t) = \frac{C(t)}{V\tau^2} t e^{-\frac{t}{\tau}} \quad (98)$$

where C(t), V, and τ are the amount of consumed carbohydrate, the distribution volume, and the peak time of meal absorption, respectively. In the original Bergman's model and its extensions, the unknown model parameters $p_1$, $p_2$, $p_3$, $p_4$, V, and τ are not time-varying. However, due to the complexity of the human body and intersubject variability, a constant set of parameters may not be able to describe all time-varying dynamics for a subject. Also, intrasubject variability may require different sets of parameters for different subjects. In embodiments of this invention, all unknown parameters and the basal plasma glucose concentration $G_b$ are defined to be time-varying in order to overcome the inter- and intrasubject variability. Using the first forward difference derivative approximation, (96)-(98) are discretized as:

$$G_s(k+1) = \quad (99)$$
$$h\left[p_1(k)\left(G_b(k) + \frac{G_s(k)}{hp_1(k)} - G_s(k)\right) - p_4(k)I_{eff}(k)G_s(k) + Ra(k)\right]$$

$$I_{eff}(k+1) = h\left[p_2(k)\left(\frac{I_{eff}(k)}{hp_2(k)} - I_{eff}(k)\right) + p_3(k)I_p(k)\right] \quad (100)$$

$$R_a(k+1) = \frac{hC(k)}{V(k)a\tau(k)^2} + 2\frac{R_a(k)}{a} - \frac{R_a(k-1)}{a^2} \quad (101)$$

$$\begin{bmatrix} I_p(k+1) \\ C(k+1) \\ p_1(k+1) \\ p_2(k+1) \\ p_3(k+1) \\ p_4(k+1) \\ V(k+1) \\ \tau(k+1) \end{bmatrix} = \begin{bmatrix} 0 \\ 0 \\ p_1(k) \\ p_2(k) \\ 0 \\ p_4(k) \\ 0 \\ \tau(k) \end{bmatrix} + w(k) \quad (102)$$

$$G_b = \begin{cases} 100, & k < \frac{2l}{h} \\ \frac{h}{T}\sum_{i=k-\frac{2l}{h}+1}^{k-\frac{l}{h}} G_{s(i)}, & k \geq \frac{2l}{h} \end{cases} \quad (103)$$

where $$a = e^{\frac{h}{\tau(k)}},$$

and h and w(k) represent sampling tune and noise term, respectively. l is the length of the window that is used for calculation of $G_b$ and selected to be 30 min. The notation for plasma glucose concentration G(t) in (73) is replaced with subcutaneous glucose concentration (CGM) $G_3$(k) in (76). The relation between two variables was shown to be a one-compartment model with a delay parameter, which was neglected in the example below due to validation reasons.

The Unsecured Kalman filter is a powerful tool for state estimation of nonlinear systems. The drawbacks of linear approximation at an operating point and calculation of Jacobian matrices in the extended Kalman filter are overcome by using a minimal set of carefully chosen sample (sigma) points.

A nonlinear state-space model is derived from (76)-(80):

$$x(k+1)=f(x(k))+w(k)$$

$$y(k)=g(x(k))+v(k) \quad (104)$$

where x(k) is the state vector, w(k) and v(k) are defined to the process and measurement noises, respectively. The nonlinear functions $f(\bullet)$ and $g(\bullet)$ are defined from (99)-(103). The state-space model in (81) has eight states since some parameters in (99)-(103) are defined to be part of noise term w(k).

Defining L as the dimension of x vector, the scalar weights $W_i$ are defined as:

$$W_0^x = \mu/(L+\mu)$$

$$W_0^y = \mu/(L+\mu)+(1-\alpha^2+\beta)$$

$$W_i^x = W_i^y = 1/[2(L+\mu)] \quad (105)$$

where i=1, ..., 2L and $\mu=\alpha^2(L+\kappa)$. The tuning parameters α, β, and κ are selected to be 1, 2, and 0, respectively. The sigma-point vectors $\chi_i$ are defined as:

$$\chi_0(k-1)=\hat{x}(k-1)$$

$$\chi_i(k-1)=\hat{x}(k-1)+\gamma\times\eta_i$$

$$\chi_{i+L}(k-1)=\hat{x}(k-1)-\gamma\times\eta_i \quad (106)$$

where $\eta_i$ is the ith column (i=1, ..., L) of the squared roof of the augmented covariance matrix P(k−1) and the parameter $\gamma=\sqrt{L+\mu}$. Prior sigma-point estimations $\chi_i^-$ are calculated by propagating the sigma-points $\chi_i(k-1)$ through, the nonlinear function $f(\bullet)$. The prior sigma points are trimmed with a nonlinear optimization to prevent nonrealistic estimations such as negative values in concentrations:

$$\chi_i^-(k)=\min[\Delta\chi_i]^T[\Delta\chi_i]$$

$$\Delta\chi_i=\chi_i^-(k)-f(\chi_i((k-1))$$

$$\chi_{min} \leq \chi_i^-(k) \leq \chi_{max}$$

$$i=0, \ldots, 2L. \quad (107)$$

The prior state estimations and covariance matrix are calculated as:

$$\hat{x}^-(k) = \sum_{i=0}^{2L} W_i^x \chi_i^-(k) \quad (108)$$

$$P^-(k) = \sum_{i=0}^{2L} W_i^y [\chi_i^-(k) - \hat{x}^-(k)][\chi_i^-(k) - \hat{x}^-(k)]^T + Q_P \quad (109)$$

where $Q_p$ is the covariance matrix of the process noise. The prior sigma-point estimations are propagated through the nonlinear function g(•) for calculation of prior output sigma points $\Upsilon_{i}^{-}$:

$$\Upsilon_{i}^{-}(k) = g(\mathcal{X}_{i}^{-}(k))$$

$$i=0,\ldots,2L. \quad (110)$$

The measurement estimations are obtained from the output sigma points as:

$$\hat{y}^{-}(k) = \sum_{i=0}^{2L} W_{i}^{x} \Upsilon_{i}^{-}(k) \quad (111)$$

The innovation-covariance and cross-covariance matrices are calculated as:

$$P_{yy}(k) = \sum_{i=0}^{2L} W_{i}^{y} [\Upsilon_{i}^{-}(k) - \hat{y}^{-}(k)][\Upsilon_{i}^{-}(k) - \hat{y}^{-}(k)]^{T} + Q_{m} \quad (112)$$

$$P_{xy}(k) = \sum_{i=0}^{2L} W_{i}^{y} [\mathcal{X}_{i}^{-}(k) - \hat{x}^{-}(k)] \quad (113)$$
$$[\Upsilon_{i}^{-}(k) - \hat{y}^{-}(k)]^{T}$$

where $Q_m$ represents the covariance matrix for process measurement noise. Finally, the Kalman filter gain and the updated state vector estimation and covariance matrix are calculated as:

$$K(k) = P_{xy}(k)(P_{yy}(k))^{-1} \quad (114)$$

$$\hat{x}(k) = \hat{x}^{-}(k) + K(k)(y(k) - \hat{y}^{-}(k)) \quad (115)$$

$$P(k) = P^{-}(k) - K(k)P_{yy}(k)(K(k))^{T}. \quad (116)$$

To demonstrate meal detection according to this invention, example data were collected, from nine subjects undergoing multivariable AP control system experiments without any announcement (meal, or exercise). Closed-loop control was performed for 32 h for each subject. Based on the study protocol, breakfast, lunch, dinner, and a late time snack were provided. Additional snacks were provided whenever requested by the subjects. The types of foods were selected based on a subject's personal requirements. No limitation on food or snack intake was imposed. The subject's own insulin type and pump were used during the experiments. Data were continuously collected from the subjects with a sampling time of 5 min. Every 10 min, insulin infusion rates were Computed by the controller and used to adjust the pump. Guardian REAL-time CGMs (Medtronics, Northride, Calif., USA) were used to collect the glucose concentration information.

To minimise the effect of CGM measurement noise on the first forward difference derivative approximation, 1-min sampled CGM data are obtained, from original data sampled every 5 min, using pchip interpolation. The initial conditions and tuning parameters are selected as:

$$\hat{x}(0) = \begin{bmatrix} I_{eff}(0) \\ G_s(0) \\ R_a(0) \\ R_a(-1) \\ p_1(0) \\ p_2(0) \\ p_4(0) \\ \tau(0) \end{bmatrix} = \begin{bmatrix} 0 \\ CGM(1) \\ 0 \\ 0 \\ 0.068 \\ 0.037 \\ 1.3 \\ 20 \end{bmatrix} \quad (117)$$

$$Q_P = \text{diag}[\, 10^{-6} \ \ 10^{-6} \ \ 10^{-3} \ \ 10^{-3} \ \ 10^{-2} \ \ 10^{-1} \ \ 10^{-2} \ \ 10^{-1} \,]$$

$$P(0) = I_{8\times 8} \ \ Q_m = 100$$

where CGM(1) is the first measured glucose value and the initial, values for $p_1$, $p_2$, and $p_4$ were adapted from the literature.

The meal-detection algorithm was developed based on the state estimations $\hat{x}(k)$ from the UKF algorithm. A meal is detected if the estimated rate of appearance of glucose $R_a(k)$ is above the threshold of 2 [mg/dl/min]. Once the $R_a(k)$ value goes below the threshold, a flag is lifted and another meal is detected when the value gets above 2 mg/dl/min. For safety from hypoglycemia, a meal detected is used for insulin bolus decision only when CGM values are above 100 [mg/dl].

Figure 28:
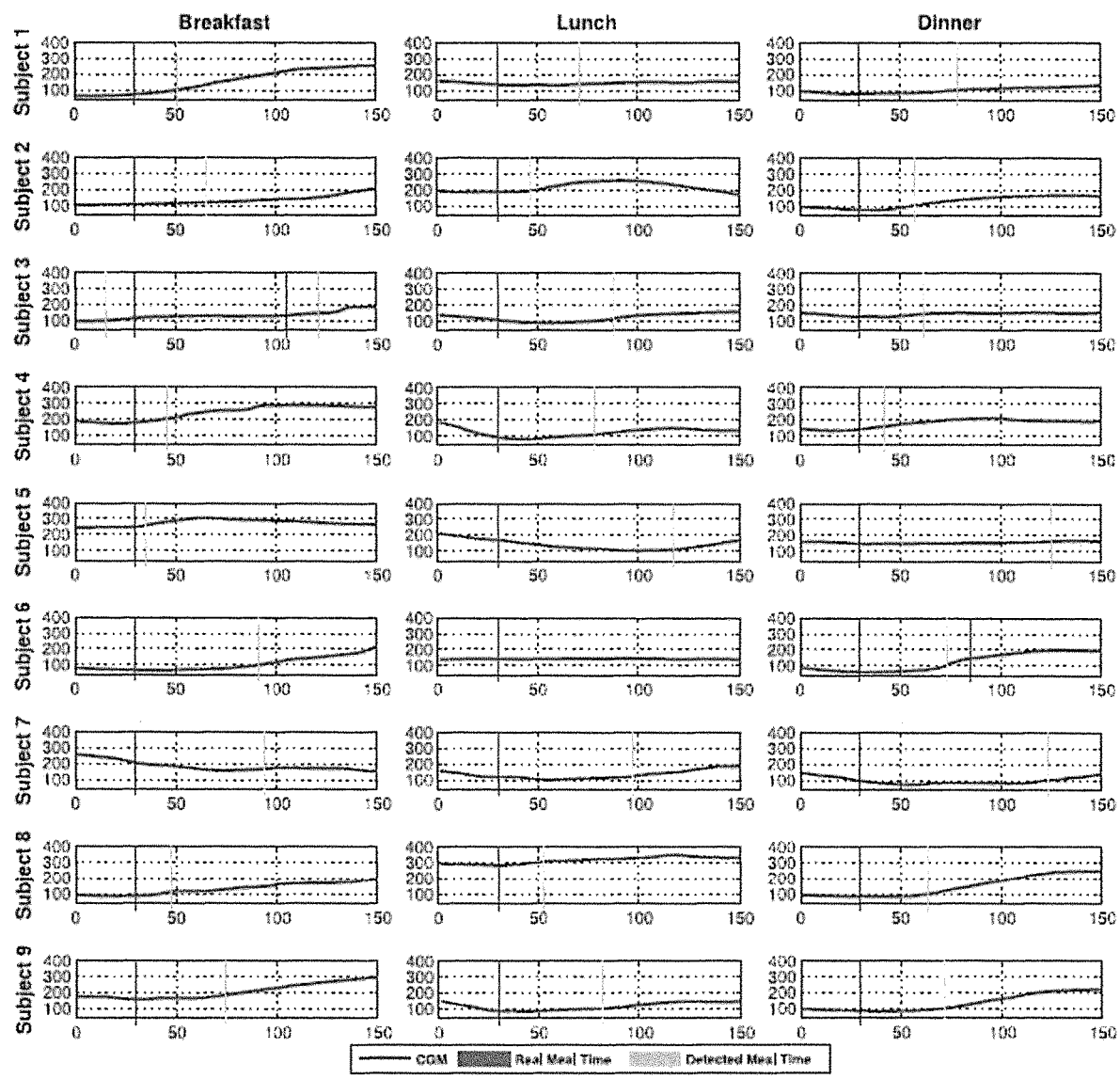

FIG. 28 shows the performance of the proposed method for 27 different main meals (breakfast, lunch, and dinner) for nine subjects. Each subfigure shows the time interval of 30 min before and 120 min after a meal. The difference in glucose values (change in glucose) between the time that meal starts and the time that meal is detected was used as the evaluation criterion. Detection time was not used as an evaluation criterion due to time-varying meal consumption lengths from subject to subject. Different types of foods have different digestion and absorption rates which also prevent using detection time as an evaluation criterion.

Table XIII summarizes the results for nine subjects data. Overall, 51 main meal and 13 snack periods were tested. Out of 63 cases, only two meals were missed. As shown in FIG. 28, the lunch for subject 6 was missed because there is almost no change in glucose values after the consumption of 45 g of carbohydrates. This might be due to insulin on board that was already active. A meal was not detected for subject 4 because a snack, which was detected by the algorithm, was consumed by the subject before the undetected meal. Since the glucose increase from the meal was almost linearly added to the increase from the snack, the algorithm could not distinguish between the two consumptions and interprets them as one meal. Considering only the successfully detected 61 meal and snack periods, the average change in glucose is 16 (±9.42) [mg/dl]. For all tested datasets, there was only one wrong alarm for subject 4, where there was a rapid increase in glucose but no recorded meals at that time. This might be because of a missed recorded meal.

TABLE XIII

|  | # of meals | Carb amounts | TD | MD | FD | CGM at meal time | CGM at detection time | Change in glucose |
|---|---|---|---|---|---|---|---|---|
| Subject 1 | 3 | 68 (±7.64) | 3 | 0 | 0 | 94 (±36.59) | 113 (±23.09) | 19 (±13.86) |
| Subject 2 | 5 | 53 (±9.75) | 5 | 0 | 0 | 145 (±55.57) | 159 (±47.81) | 13 (±8.99) |
| Subject 3 | 6 | 62 (±17.3) | 6 | 0 | 0 | 104 (±23.48) | 117 (±21.29) | 13 (±13.67) |
| Subject 4 | 6 | 71 (±17.6) | 5 | 1 | 1 | 169 (±61.81) | 175 (±62.5) | 6 (±22.4) |
| Subject 5 | 6 | 85 (±21.0) | 6 | 0 | 0 | 135 (±67.1) | 141 (±60.44) | 6 (±33.07) |
| Subject 6 | 5 | 60 (±10.6) | 4 | 1 | 0 | 115 (±82.5) | 155 (±88.05) | 40 (±8.79) |
| Subject 7 | 7 | 83 (±46.36) | 7 | 0 | 0 | 133 (±46.46) | 148 (±36.18) | 14 (±27.13) |
| Subject 8 | 6 | 58 (±14.15) | 6 | 0 | 0 | 160 (±86.85) | 176 (±83.57) | 15 (±10.27) |
| Subject 9 | 6 | 65 (±6.37) | 6 | 0 | 0 | 134 (±43.19) | 143 (±42.19) | 9 (±11.24) |
|  | # of snacks |  |  |  |  |  |  |  |
| Subject 1 | 0 | 0 (±0) | 0 | 0 | 0 | 0 (±0) | 0 (±0) | 0 (±0) |
| Subject 2 | 1 | 30 (±0) | 1 | 0 | 0 | 68 (±0) | 100 (±0) | 32 (±0) |
| Subject 3 | 1 | 30 (±0) | 1 | 0 | 0 | 133 (±0) | 146 (±0) | 13 (±0) |
| Subject 4 | 4 | 26 (±7.5) | 4 | 0 | 0 | 137 (±39.16) | 158 (±40.39) | 20 (±16.68) |
| Subject 5 | 2 | 22 (±10.6) | 2 | 0 | 0 | 106 (±29.69) | 119 (±27.57) | 13 (±2.12) |
| Subject 6 | 1 | 15 (±0) | 1 | 0 | 0 | 120 (±0) | 149 (±0) | 29 (±0) |
| Subject 7 | 1 | 30 (±0) | 1 | 0 | 0 | 123 (±0) | 156 (±0) | 33 (±0) |
| Subject 8 | 2 | 20 (±0) | 2 | 0 | 0 | 122 (±39.59) | 131 (±38.18) | 9 (±1.41) |
| Subject 9 | 1 | 15 (±0) | 1 | 0 | 0 | 194 (±0) | 200 (±0) | 6 (±0) |
| Total | 63 | 44 (±9.38) | 61 | 2 | 1 | 121 (±33.99) | 138 (±31.74) | 16 (±9.42) |

Values are shown as mean (±standard deviation). TD: true detection, MD: missed detection, FD: false detection. The units are mg/dl and grams for glucose values and carb amounts, respectively.

The rate of appearance of glucose $R_a(k)$ estimations was used for calculation of meal boluses. A meal bolus was given when the estimated $R_a(k)$ was above 2 [mg/dl/min] and measured CGM value is above 100 [mg/dl]. A second meal bolus can be given only after the $R_a(k)$ values go below the 2 [mg/dl/min] threshold and 30 min passed over the last infused meal bolus. Once a meal bolus was infused, a flag was turned on to activate correction bolus (CB) infusion and the 2 [mg/dl/min] threshold was increased to 3 [mg/dl/min]. While the flag was ON, the $R_a(k)$ value was checked every 15 min and a CB was given if the $R_a(k)$ was above the new threshold. For each given CB, the threshold was increased by 1 [mg/dl/min] and the process was repeated every 15 min until the flag is turned OFF. The CBs are calculated based on measured CGM values $G_s(k)$ and subject's body weight (BW) as a function of total daily dose (TDD) as follows:

$$CB = \frac{G_s(k) - r(k)}{1800} \times TDD \quad (118)$$

$$r(k) = \mu G_s(k) + (1 - \mu)r_0 \quad (119)$$

$$TDD = \frac{G_s(k)}{r(k)} \times BW \quad (120)$$

where $r_0$ and $\mu$ are the desired set point, and the tuning parameter that affects the amount of CB infusions, respectively. The values $\mu$ were selected to be 0.55, 0.3, and 0.1 for sensitive, normal, and resistant adults or adolescents and 0.8, 0.7, and 0.45 for sensitive, normal, and resistant children, respectively. The set point $r_0$ is set to 100 mg/dl. The proposed meal bolus calculation strategy was performed on the academic version of UVa/Padova metabolic simulator, which had 30 subjects (ten adults, ten adolescents, and ten children). A three-day simulation scenario was generated and 300 simulations (ten for each subject) were performed. The same scenario was used for adults and adolescents. The amount of carbohydrates, in meals was reduced for children.

The 30 subjects of the UVa/Padova metabolic simulator were divided into three subgroups (sensitive, normal, resistant) based on a subject's insulin sensitivity. The amount of meal boluses were defined based on these three subgroups. The meal boluses were selected to be 4 [U], 3 [U], and 2 [U] for the resistant, normal, and sensitive adult and adolescent subjects and 1 [U], 0.85 [U], and 0.7 [U] for the resistant, normal, and sensitive child subjects, respectively.

Figure 29:
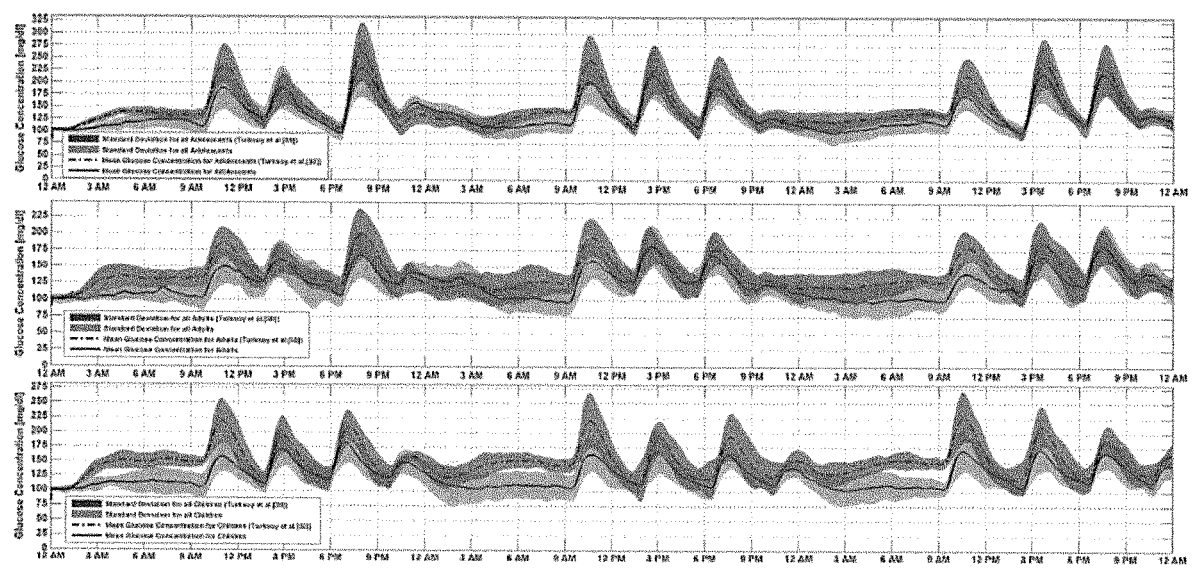

FIG. 29 shows the average glucose concentration (CGM) for all 30 subjects (means and standard deviations). The mean glucose concentration for adolescents in the target range is 86.8% of the time and was stable during the night. Better glucose regulation was obtained in adults subjects. During 94.7% of the simulation time, glucose concentration stayed within the target range even though meals with high carbohydrate content were provided. A successful glucose regulation was obtained for the children subjects where 92% of the time, glucose concentration stayed within the target range. The time in hyperglycemic range was significantly ($p<0.01$) decreased with the proposed meal bolus calculation algorithm.

The meal-detection algorithm developed was able to detect almost, all tested meals. Simulation results indicate that using such a high-performance meal-detection module in AP control systems can prevent most of hyperglycemia by providing bolus insulin for meals before large increases in BGC without any manual information from patients. The meal-detection method of this invention can be incorporated into a module for the artificial pancreas device of this invention. The meal-detection module is completely adaptive and does not require any subject-specific initialization. It works based on only CGM measurements. The early detection of meals by the meal-detection module enables the device to provide a meal bolus (without any manual announcements) that would prevent most of postprandial hyperglycemia.

In a second study, seven subjects included in this analysis were young adults with fair glucose control (Table XIV) using continuous subcutaneous insulin infusion pump for their glucose regulation. The subjects met with the investigators for a total of 3 days; however, to best facilitate retention, some subjects opted split day(s) into 4 hour blocks of time totaling 24 hours. Based on some subjects' schedule, some of the experiments took 2 weeks to 8 weeks (total hours stay at facility was the still same). Subjects were provided meals and snacks during their stay. The meal numbers and amounts were defined based on subjects preferences. Additional snacks were provided whenever requested by subjects. Subjects used their own meal bolus and correction insulin calculation methods prescribed by their own diabetes provider.

TABLE XIV

| Subject | Age | Gender | HbA1c (%) | Weight (kg) | BMI | Diabetes duration (years) |
|---|---|---|---|---|---|---|
| 1 | 24 | M | 7.1 | 76 | 25.7 | 11 |
| 2 | 34 | M | 8.6 | 76 | 23.5 | 32 |
| 3 | 23 | M | 8.6 | 67 | 24.0 | 17 |
| 4 | 18 | F | 6.8 | 60 | 26.9 | 16 |
| 5 | 20 | M | 8.3 | 75 | 23.8 | 11 |
| 6 | 21 | M | 7.3 | 67 | 20.2 | 5 |
| 7 | 32 | F | 7.0 | 108 | 38.3 | 30 |

The closed loop occurred over a 3-day period. Subjects were provided two CGM devices, a BodyMedia SenseWear armband, and a Zephyr chestband. The subjects had a CGM placed prior to the study, and the study doctor had begun to remotely monitor subject BGs before the study began then continuously during the study. Continuous data collection from the subject started on Day 1 and insulin delivery via the algorithm continued for 60 hours. Data were collected and transmitted to a laptop computer, every 5 minutes. All three days subjects had exercises personalized to individual subjects, to include aerobic, resistance or interval exercises in the same sequence for all subjects according to the individuals' fitness level. Exercise intensity was calculated based on subjects' exercise stress tests from reference (OL) experiments. According to the Karvonen formula, the subjects' target heart rate training zone was calculated. The formula uses maximum and resting heart rate (HR) with the desired training intensity to get a target heart rate (((maximal HR−resting HR)×65 to 85% intensity)+resting HR). For interval training, moderate intensity is 60-70% of heart rate reserve and high intensity is 85-90% of heart rate reserve. Every 10 minutes insulin infusion rates were computed by the controller (CL) and overseen by a physician. Subjects were monitored, for hypo- and hyperglycemia, during this time and discharged, from the facility approximately 2 hours following disconnection from the algorithm. Daily dietary needs (8 meals and snacks) and two nights sleeping accommodations were provided. Foods consumed (type and amount) and physical activity, were logged throughout the study period. The meal contents were not controlled and were defined based on subjects' preferences similar to the OL experiments.

Figure 30:
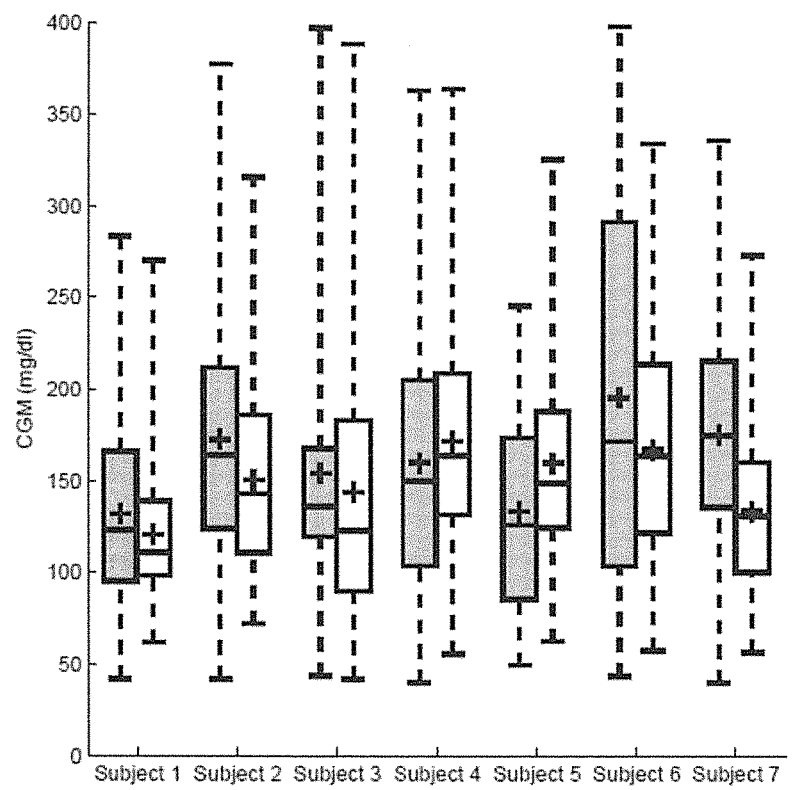
FIG. 30 includes a graph produced during testing of examples of the invention.

Overall 14 experiments were performed on the 7 different subjects. Subjects made their own insulin decisions in the OL experiments while the device with the proposed meal bolus module is used during the CL experiments. FIG. 30 compares all OL vs CL experiments. For almost all subjects, the maximum values were lower during the CL experiments compared to OL experiments. Another comparison was made based on the maximum, values of each postprandial meal, period (approximately 2 hours; highest glucose value after a meal). The statistical equivalence test was used to show the statistical similarity between the OL and CL experiment results. Overall 51 postprandial glucose peaks from 14 experiments (7 OL and 7 CL) are compared.

Figure 31:
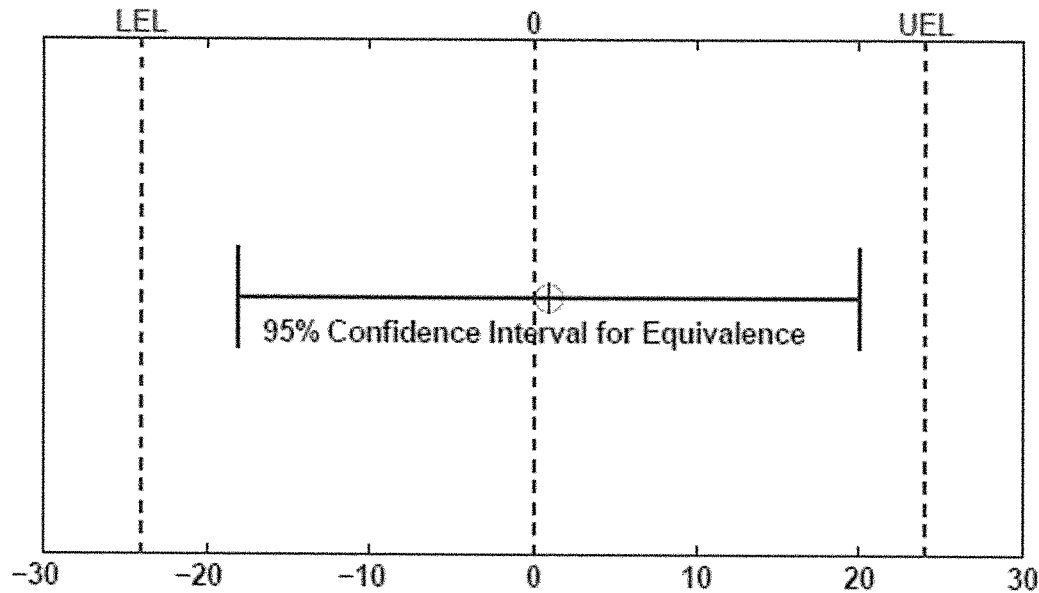
FIG. 31 summarises results produced during testing of examples of the invention.

FIG. 31 shows that the CL results can be considered statistically (p=0.05) equivalent to the OL results. The 95% of the confidence interval stays between upper and lower limits which impose the statistical similarity in two arms. The upper and lower equivalence limits are defined to be −10% and 10% of the mean of the reference (OL) data. These limits are user defined margins where narrower margins make it more difficult to establish equivalence. The FDA has suggested the margins to be a fraction (0.5) of the lower limit of a confidence interval of the difference between the reference and tested population when the outcome is mortality.

Figure 32:
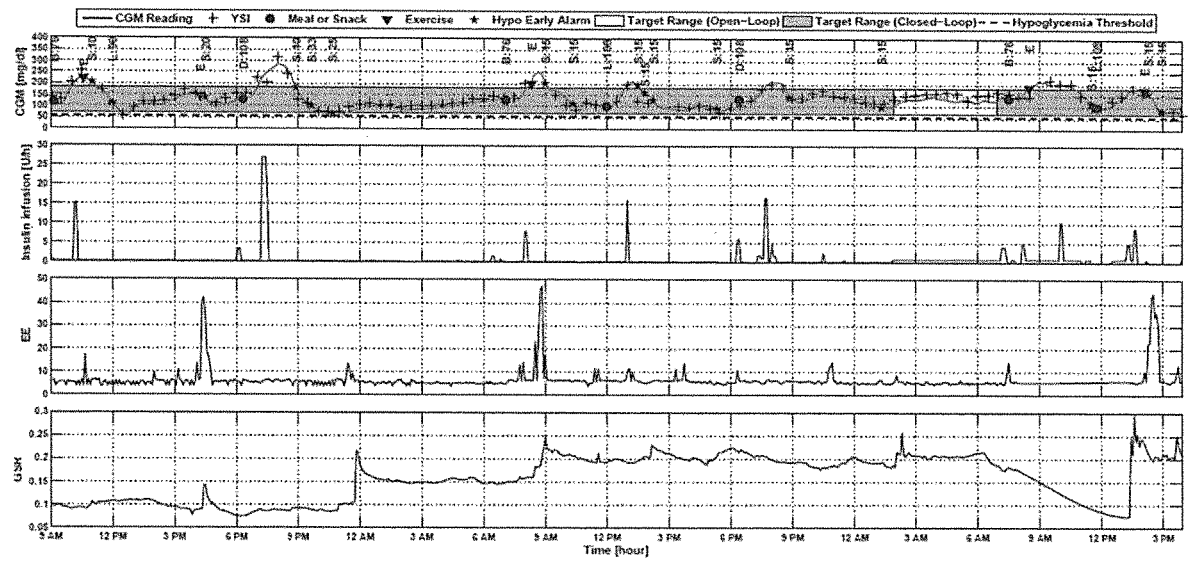
FIG. 32 includes charts produced during testing of examples of the invention.

Two separate CL experiments were performed with Subject 1 where the meal bolusing method was tested during only the latter experiment. FIG. 32 shows the results of the CL experiments where only the IMA-AP system was performed. During 60 hours of the CL duration 81% of the time CGM values stayed in a 70-180 mg/dl target range. 2.2% of the time CGM values stayed above 250 mg/dl where the maximum glucose, value observed was 287 mg/dl. Significantly better glucose control was observed when the proposed algorithm was used. 88.5% of the time CGM values stayed in 70-180 mg/dl with a maximum value of 249 mg/dl. The unannounced meal bolusing method and module of this invention was able to keep glucose concentrations as low as OL experiments where subjects infuse their own insulin before starting a meal.

Hypoglycemia Detection

People with Type 1 Diabetes (T1D) may experience hypoglycemic (blood glucose concentration ((BGC)<70 mg/dl) episodes that may be caused by insulin doses that are too large in relation to the BGC, reduced food intake, extensive physical activity, or slow absorption of currently available "fast-acting" insulins. Fear of hypoglycemia is a major concern for many patients and affects patient decisions for use of an artificial pancreas (AP) system. Various strategies have been proposed for predicting BGC to be implemented in an AP system for prevention of hypoglycemia.

The indention further includes a method and hypoglycemia detection and or alarm module for prevention of hypoglycemia by issuing predictive hypoglycemia alarms and encouraging patients to consume carbohydrates in a timely manner. The method was tested on 6 subjects over three-day clinical experiments. Over 6 three-day clinical experiments, there were only 5 real hypoglycemic episodes of which only 1 episode of hypoglycemia occurred due to being missed by the proposed algorithm. The average glucose value at the time first alarms were triggered as recorded to be 117±30.6 mg/dl. The average carbohydrate consumption per alarm was 14±7.8 grams. The results show that most of low glucose concentrations can be predicted in advance and the glucose levels can be raised back to the desired levels by consuming an appropriate amount of carbohydrate. The method is thus able to prevent most hypoglycemic events by suggesting appropriate levels of carbohydrate consumption before the actual occurrence of hypoglycemia.

The experiments were performed over a 3-day period. Six subjects (3 male and 3 female, age: 24.2±4.5, weight: 79.2±16.2 (kg), height: 172.7±9.4 (cm), HbA1C (%): 7.3±0.48, duration with diabetes (months): 209.2±87.9) participated in the study. Subjects were provided two CGM devices, a BodyMedia SenseWear armband, and a Zephyr chestband. The subjects had a CGM placed prior to the study, and the study MD had begun to remotely monitor subject blood glucose before the study began then continuously during the study. Continuous data collection from the subjects started on Day 1 and insulin delivery via AP methods continued for 60 hours. Data were collected and transmitted to a laptop computer, every 5 minutes. Plasma glucose concentration was measured every 30 minutes using the YSI 2300 STAT (Yellow Springs Instrument, Yellow Springs, Ohio). All three days subjects had exercises personalized to individual subjects, to include aerobic, resistance or interval exercises in the same sequence for all subjects according to the individual's fitness level Exercise intensity was calculated based on subjects' exercise stress tests. The subjects' target heart rate training zone was calculated according to the Karvonen formula. The formula uses maximum and resting heart rate (HR) with the desired training intensity to get a target heart rate (((maximal HR−resting HR)×65 to 85% intensity)+resting HR).

For interval training, moderate intensity is 60-70% of heart rate reserve and high intensity is 85-90% of heart rate reserve. Subjects were monitored for hypo- and hyperglycemia during this time and discharged from the CRC approximately 2 hours following disconnection from the algorithm. Daily dietary needs (8 meals and 2 snacks) and two nights sleeping accommodations were provided. Participants received a 1d-cycle rotating menu each day for 3 days customized to individual food preferences. Prior to admission for the study, participants were interviewed by phone to plan the study diet. Carbohydrate intake was kept very similar to their usual intake. Daily calories were divided among breakfast (25%), lunch (30%), dinner (35%) and evening snack (10%). The caloric content and macronutrient composition of consumed meals, snacks and beverages were calculated using Food Processor SQL (version 10.15.41, ESHA Research, Salem, Oreg.). Participants were not required to eat 100% of meals and were only allowed to eat food provided by the CRC Metabolic Kitchen. Any food that was not consumed was weighed back. Foods consumed (type and amount) and physical activity, were logged throughout the study period.

Glucose predictions were obtained by using a multivariable time-series models where glucose concentration was expressed as a function of past glucose concentration and physical activity signal readings and infused insulin amounts by using an ARMAX model structure:

$$A(q^{-1})y(k)=B_i(q^{-1})u_i(k-1-d_i)+C(q^{-1})\in(k) \quad (121)$$

where $q^{-1}$ is the backward shift operator, $y(k)$ is the observation (CGM readings), $u(k-1)$ is the $i^{th}$ input variable at $k-1^{th}$ sampling time, $\in(k)$ is the white noise at $k^{th}$ sampling time, $d_t$ is the delay term for the corresponding input.

$$A(q^{-1}) = 1 + a_1 q^{-1} + a_2 q^{-2} + \ldots + a_{n_A} q^{-n_A} \quad (122)$$

$$B_l(q^{-1}) = b_{a_l} + b_{1_l} q^{-1} + b_{2_l} q^{-2} + \ldots + b_{n_{B_l}} q^{-n_{B_l}} \quad (123)$$

$$C(q^{-1}) = 1 + c_1 q^{-1} + c_2 q^{-2} + \ldots + c_{n_C} q^{-n_C} \quad (124)$$

where $n_A$, $n_B$, $n_C$ are model orders that are determined based on the properties system. The model in Eq. (121) has one output (glucose measurements) and three inputs (infused insulin, measured energy expenditure and galvanic skin response), respectively. With every new measurements, the model in Eq. (121) was used for 30 minutes prediction of glucose concentration, according to earlier work.

Figure 33:
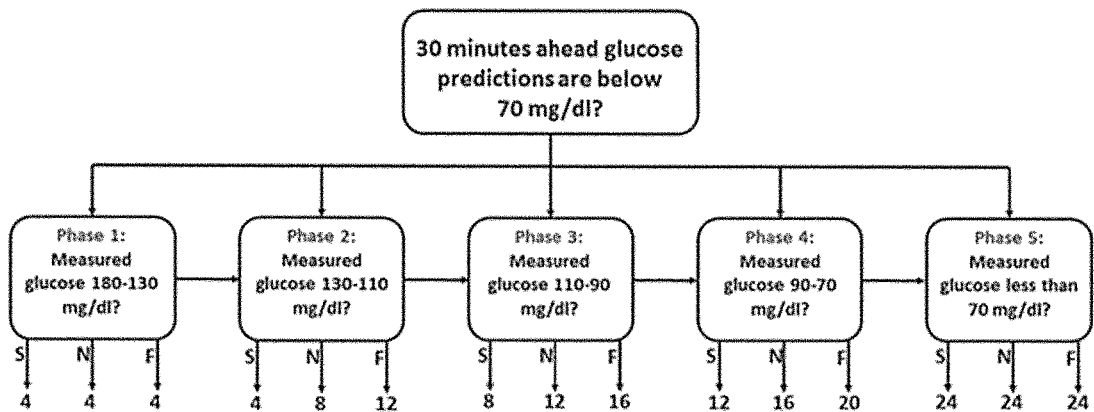
FIG. 33 is a flow chart of hypoglycemia detection-based carbohydrate suggestion (values are shown in grams) according to one embodiment of this invention.

Based on measured glucose values five different phases were defined as shown in FIG. 33. For each phase three different speeds of glucose decrease (S: slow, N: normal, F: fast) were defined as:

$$\text{speed} = \begin{cases} S, & -30 \leq \theta \\ N, & -60 \leq \theta \leq -30 \\ F, & \theta < -60 \end{cases} \quad (125)$$

$$\theta = \tan^{-1}\left[\frac{\sum_{i=k-N}^{k}(x_{t-k+N}-x)(y_t-y)}{\sum_{i=0}^{N}(x_i-x)^2}\right] \quad (126)$$

where x=[0, 5, 10, 15, 20, 25] (based on 5 minutes sampling time) and $y_k$ is measured glucose at time k. X and Y are mean values of x and $y_t$(t=k−N, . . . , k), respectively. The moving window length N is selected to be 5 (last 30 minutes).

With every new measurement, 30-minutes-ahead glucose predictions were compared with 70 the mg/dl mild hypoglycemia threshold (80 mg/dl during exercise). If the predicted values were below the threshold, the last measured glucose value was used for determination of the phase interval. At the same time, the speed of glucose reduction was obtained using Eqs. (125) and (126). Once the phase and the speed of reduction, were calculated, specific amounts of CHO (FIG. 33) were suggested to patients for consumption. Only one CHO suggestion was done in one phase (except phase 5) until glucose levels decreased to the next level.

The method was tested on 6 subjects over three-day closed loop experiments. When hypoglycemia was detected, subjects were notified for the potential low glucose concentration and the module algorithm, suggested some amounts of warning CHO to be consumed according to the flowchart in FIG. 33. However, subjects were free to eat CHO amounts different than the suggested amount or not eat.

Figure 34:
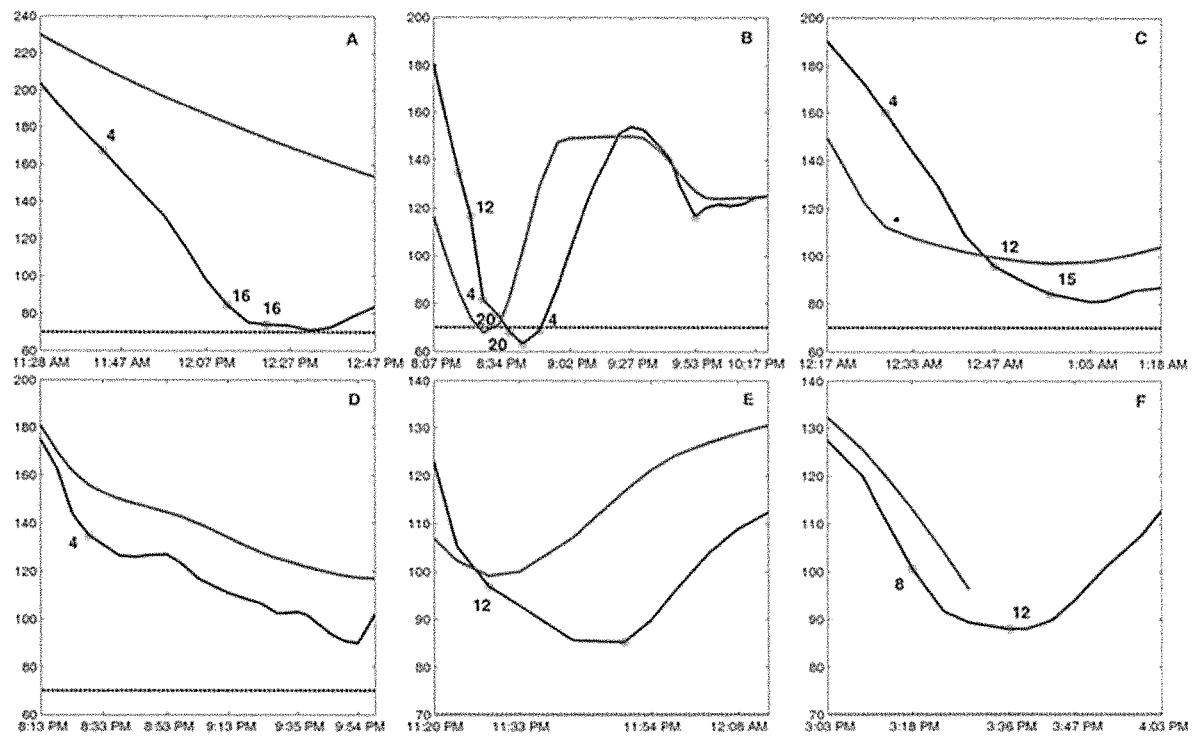
FIGS. 34-40 include graphs produced during testing of examples of the invention.

In the first experiments, hypoglycemia alarms were issued during six time periods throughout, the three-day experiment and warning CHO were suggested by the algorithm (FIG. 34). Overall 15 times (10.9±8.9 gram, total 163 gram) different CHO amounts were taken. A mild hypoglycemia occurred only on one occasion. This might have been prevented if the subject had consumed the suggested CHO amount when the first alarm was issued (FIG. 34B). The average glucose value was 132±29.2 mg/dl when the first hypoglycemia alarms were issued.

Figure 35:
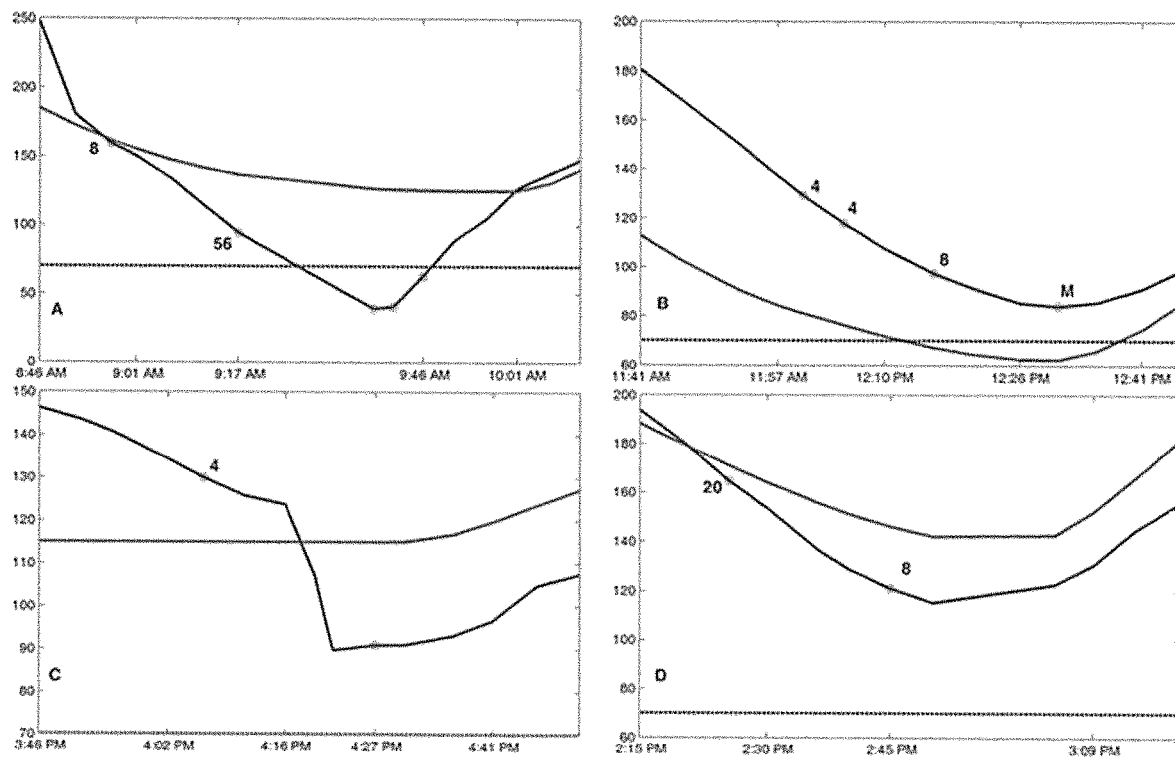

The second experiment had 4 potential hypoglycemic periods (FIG. 35). Warning CHOs were taken 8 times (14±17.8 gram, total 112 gram) during the three-day experiment. The first hypoglycemia alarm was issued during the exercise session on the first, day and the administration of 8 grams of CHO was suggested. However, the actual response to the alarm was a CHO amount that was much more than the suggested amount. This was caused by an inaccurate finger-stick measurement, during the exercise period which showed the glucose value to be 33 mg/dl. Later, this reading was found to be wrong when YSI values were obtained from laboratory. The next hypoglycemia alarms occurred close to lunch time, and the subject preferred not to consume the suggested CMC) amounts and wait for lunch. During the later period (FIG. 35C) there was a sharp decrease in CGM readings, which later was found to be sensor discrepancy. During the last period, CHO amounts were suggested at higher glucose values because, the subject was in an exercise session. This was done automatically by the algorithm for prevention of exercise-induced hypoglycemia by suggesting CHO at an earlier stage using exercise information from the Bodymedia Sensewear armband. The average glucose concentration was recorded to be 1.46±19.7 mg/dl when a hypoglycemia alarm was triggered.

Figure 36:
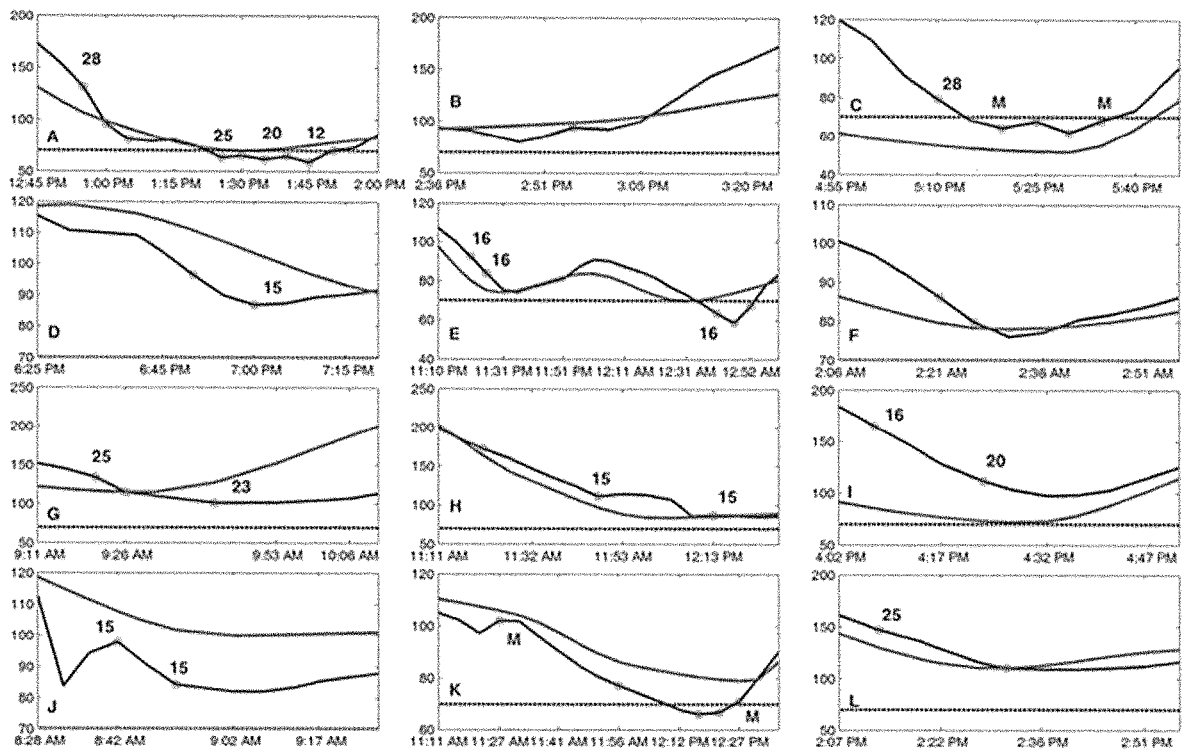

Overall, 18 times (19±5.2 gram, total 345 gram) warning CHO were taken during 12 different time instances for experiment 3 (FIG. 36). Since no limitation was made on the amount of suggested CHO amounts, subjects used their own preferences to modify the suggested amounts, which resulted in relatively higher consumed CHO in this experiment. Two of the hypoglycemia alarms overlapped with meal times and the subject preferred no additional CHO besides lunch. There was only one real hypoglycemia episode, that, could not be prevented. One possible reason for this hypoglycemia might be sensor accuracy as shown in FIG. 36. The average glucose concentration was 116±31.9 mg/dl at the time of the first hypoglycemia alarms.

Figure 37:
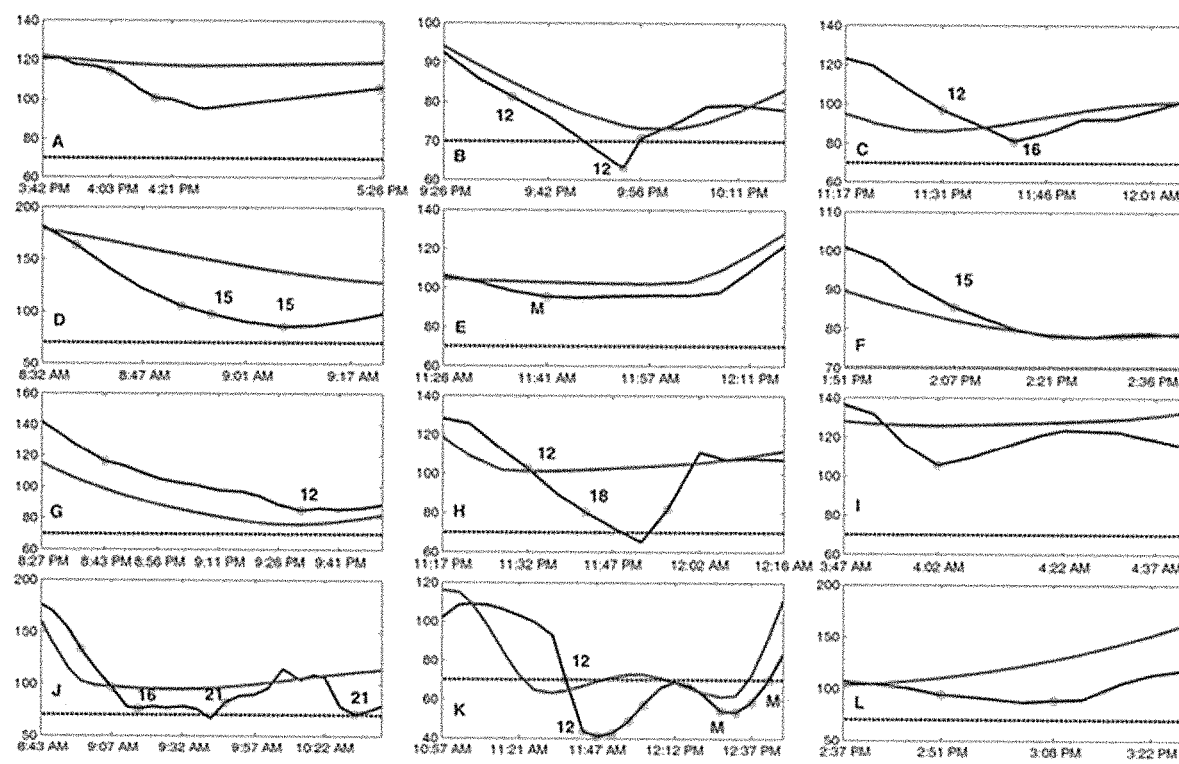

Experiment 4 had 12 different hypoglycemia warning alarm periods (FIG. 37). During the 3 days of the experiment 15 warning CHO (14±3.2 gram, total 221 gram) were consumed. There was only one case where the proposed algorithm was not able to prevent hypoglycemia. First hypoglycemia alarms: were, given at average glucose value of 105±25.2 mg/dl.

Figure 38:
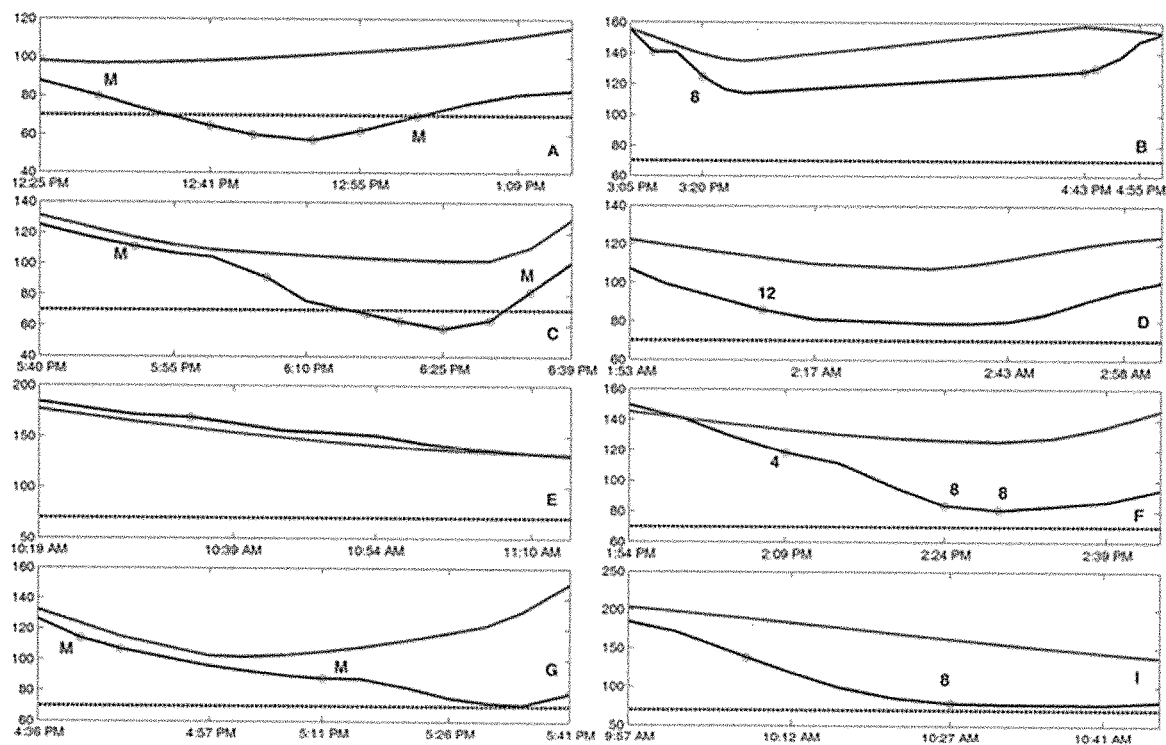

There, was no real hypoglycemia during experiment 5 (FIG. 38). At six different times, the algorithm gave a hypoglycemia alarm where three of these times overlapped with meal times and no additional CHO were provided. Overall, 6 times warning CHO (8±2.3 gram, total, 56 gram) were consumed. The average glucose concentration at the time of the first hypoglycemia alarms was observed to be 119±29.4 mg/dl.

Figure 39:
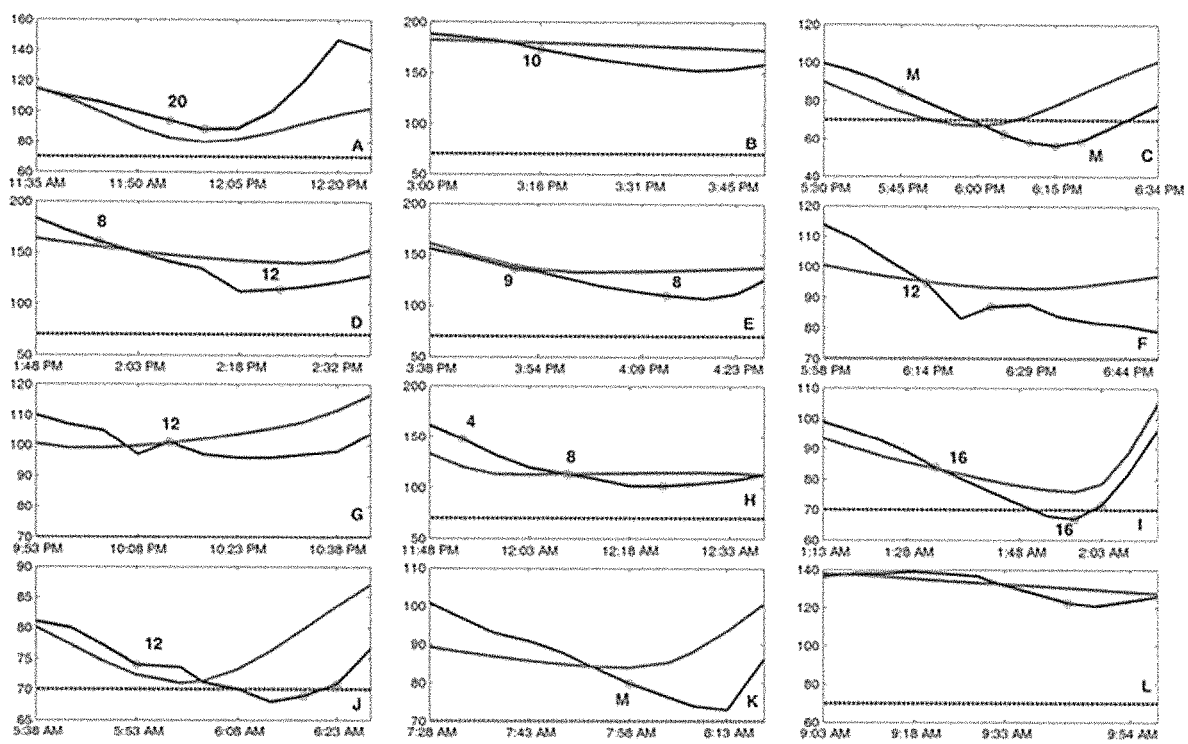

FIG. 39 shows the results from the last experiment in which the hypoglycemia alarm, was triggered twelve different periods and most of them were treated with warning CHO. Thirteen times suggested CHO amounts (11±4.2 gram, total 147 gram) were consumed by the subject. No actual hypoglycemia was observed and average glucose at the time of the first alarms was measured to be 112±34.4 mg/dl.

Table XV summarizes the results where overall 5 real hypoglycemia instances were seen during all 6 experiments. Per experiment there was only 1 hypoglycemia. Out of 5 real hypoglycemia instances, only 1 is considered to be missed as by the algorithm as the rest are due to either patients' decision, or sensor inaccuracy.

The results show that most low glucose concentrations can be predicted in advance and the glucose levels can be raised back to the desired levels by consuming appropriate amount of OHO. There were only few cases where actual hypoglycemia occurred. However, some of these hypoglycemia episodes might be due to sensor accuracy or subject GEO consumption preferences. The method thus provides a simple and effective intervention based on 30-minutes-ahead prediction of hypoglycemia. The method can be added to the developed system of this invention Including the other modules such as an adaptive controller, a hypoglycemia early alarm system, a meal detection and bolus calculator, a physical activity classifier, and a fault detection module.

TABLE XV

| Experiment | Number of Hypoglycemia Alarm Periods | Number of Real Hypoglycemia | Possible Reasons | Average Glucose value (mg/dl) | Consumed CHO (grams) |
|---|---|---|---|---|---|
| 1 | 6 | 1 | Patient decision | 132 ± 29.2 | 163 (10.9 ± 8.9) |
| 2 | 4 | 1 | Sensor accuracy | 146 ± 19.7 | 112 (14 ± 17.8) |
| 3 | 12 | 1 | Sensor accuracy | 116 ± 31.9 | 345 (19 ± 5.2) |
| 4 | 12 | 1 | Algorithm performance | 105 ± 25.2 | 221 (14 ± 3.2) |
| 5 | 8 | 0 | — | 119 ± 29.4 | 56 (8 ± 2.3) |
| 6 | 12 | 1 | Patent decision | 112 ± 34.4 | 147 (11 ± 4.2) |

Real Time Estimation of Plasma Insulin Concentration

AP control systems usually use continuous glucose measurements to calculate the optimum amount of insulin to be infused with an insulin pump in order to keep blood glucose concentration within a safe target range. Real-time estimation of plasma insulin concentrations would increase the accuracy of AP control algorithms. This information enables calculation of more realistic insulin infusion rates and prevention of hypoglycemia caused by overdosing of insulin.

The invention includes automated monitoring and/or determining plasma insulin concentration in real time from continuous glucose monitoring data by automatically implementing a mathematical model with the AP control system. Hovorka's compartmental model, developed to describe glucose-insulin dynamic in different parts of the human body, has been incorporated into a continuous-discrete extended Kalman filter (CDEKLF) to provide an estimate of plasma insulin concentration. The CDEKF is the generalization of the Kalman filter to nonlinear systems with continuous-time state equations and discrete-time measurements. Furthermore, because of variability in system, dynamics, uncertain and subject-specific model parameters have been considered as new states in Hovorka's model to be estimated by CDEKF. This method was evaluated by using clinical data from patients with Type 1 diabetes who underwent a closed-loop AP experiment. Real-time insulin estimations were compared to plasma insulin measurements to evaluate performance and validity of the proposed methodology.

Simulation results indicated that the method is able to estimate the plasma insulin concentration accurately in real time. Furthermore, the results for estimated continuous glucose measurements were compared to their real values to assess the performance of the method. This method will be beneficial for an AP system for real time estimation of non-measurable variables such as plasma, insulin concentrations. The method can be implemented as a module within the integrated multivariable adaptive AP of this invention to estimate plasma insulin concentrations and for computing insulin infusion rates and making decisions on glucose concentration management strategies for an AP user.

Embodiments of this invention incorporate a continuous-discrete extended Kalman filter (CDEKF). Hovorka's compartmental model (Hovorka et al., 2004) that describes glucose-insulin dynamics is used to develop the state model that is augmented by additional state variables describing model parameters that have significant variations, CDEKF is developed by using the augmented model.

A common approach in literature to estimate plasma insulin concentration is to simulate the insulin intakes in an insulin model. In general this nonlinear model can be represented as:

$$\dot{x} = f(x(t), u(t)) \quad (127)$$

where u(t) is the input of the model, x(t) is the system state vector, and $f(x(t), u(t))$ defines the system's dynamics.

An exemplary insulin model is one developed by Hovorka et al. (Hovorka et al., 2004). The system state vector x(t) is given by:

$$x(t) = [S_1\ S_2\ I\ x_1\ x_2\ x_3\ Z_1\ Z_2\ IG] \quad (128)$$

All model equations, variables, parameters, units and nominal values used in this model are listed in Table XVI.

TABLE XVI

Hovorka's compartmental model

| State | Differential equation | Parameters and inputs |
|---|---|---|
| Subcutaneous insulin absorption [mU] | $\dot{S}_1(t) = u(t) - \frac{S_1(t)}{t_{max,I}}$ | u(t): Administration of basal and bolus insulin [mU/min] |
|  | $\dot{S}_2(t) = \frac{S_1(t)}{t_{max,I}} - \frac{S_2(t)}{t_{max,I}}$ | $t_{max,I}$: Time-to-maximum insulin absorption [=55 min] |
| Plasma insulin concentration [mU/L] | $\dot{I}(t) = \frac{S_2(t)}{t_{max,I} V_I} - k_e I(t)$ | $V_I$: Insulin distribution volume [=0.12 * (Patient weight) L] $k_e$: Fractional elimination rate [=0.138 min$^{-1}$] |
| Effects of insulin on the distribution and transport of glucose [min$^{-1}$] | $\dot{x}_1(t) = -k_{a,1} x_1(t) + k_{b,1} I(t)$ | $k_{a,1}$: Deactivation rate constant [=0.006 min$^{-1}$] $k_{b,1}$: Activation rate constant [=ka1 * 51.2 * 10$^{-4}$ min$^{-2}$ mU$^{-1}$ L] |
| Effect of insulin on the glucose disposal [min$^{-1}$] | $\dot{x}_2(t) = -k_{a,2} x_2(t) + k_{b,2} I(t)$ | $k_{a,2}$: Deactivation rate constant [=0.06 min$^{-1}$] $k_{b,2}$: Activation rate constant [=ka1 * 8.2 * 10$^{-4}$ min$^{-2}$ mU$^{-2}$ L] |
| Effect of insulin on the production of endogenous glucose [unitless] | $\dot{x}_3(t) = -k_{a,3} x_3(t) + k_{b,3} I(t)$ | $k_{a,3}$: Deactivation rate constant [=0.03 min$^{-1}$] $k_{b,3}$: Activation rate constant [=ka1 * 520 * 10$^{-4}$ min$^{-1}$] |
| Carbohydrate absorption rate [mmol/min] | $U_G(t) = \frac{D_G A_G t e^{-t/t_{max,G}}}{t_{max,G}^2}$ | $D_G$: Amount of carbohydrates digested [mmol] $A_G$: carbohydrate bioavailability [=0.8 (Unitless)] $t_{max,G}$: Time-of-maximum appearance of glucose in the accessible compartment [=40 min] |
| Glucose masses in the accessible compartment [mmol] | $\dot{Q}_1(t) = -x_1(t) Q_1(t) + k_{12} Q_2(t) - F_{01}^c(t) - F_R(t) + U_G(t) + EGP_0(1 - x_3(t))$ | $F_{01}^c(t)$: Non-insulin-dependent glucose disposal [mmol/min] $F_R(t)$: Renal glucose clearance [mmol/min] $EGP_0$: Endogenous glucose production [=0.0161 * (Patient weight) mmol/min] |
| Glucose in non-accessible compartment [mmol] | $\dot{Q}_2(t) = x_1(t) Q_1(t) - k_{12} Q_2(t) - x_2(t) Q_2(t)$ | $k_{12}$: Transfer rate from the non-accessible to the accessible compartment [=0.066 min$^{-1}$] |
| Interstitial glucose concentration [mmol/L] | $\dot{IG}(t) = \frac{1}{\tau}\left(\frac{Q_1(t)}{V_G} - IG(t)\right)$ | $V_G$: Volume of the accessible compartment [=0.16 * (Patient weight) L] $\tau$: Time delay [=16 min] |

Systems with uncertainties in their dynamic and noise in measurements can be expressed by:

$$\dot{x} = f(x(t), u(t)) + G(t)\omega, \omega(t) \sim N(0, Q) \quad (129)$$

$$z(t) = h(x(t)) + v(t), u(t) \sim N(0, R)$$

where h(x(t)) denotes the measurement function and z(t) is the output of the model.

Furthermore, w(t) and v(t) represent uncertainties in the process model and the observation noises, while Q and R denote the variances of these noises, respectively. G(t) is also process noise matrix.

In most biological systems, only a few states are measurable (output variables z(t)). In this case, only interstitial glucose concentration (GC) can be measured by subcutaneous glucose sensors. However, state observers such as the Kalman filters can estimate unmeasured states based on a limited set of measured variables. The linear Kalman filter is a stochastic filter that estimates the states of a system based on a linear state-space model in a two-step process: the prediction and the correction steps. In the prediction step, the Kalman filter estimates the current state variables. Once new measurements (with noise) are collected, the state estimates are updated by using a correction factor based on the difference between the measured and estimated values multiplied by a gain term. The extended Kalman filter (EKF) uses local linearization to extend the Kalman filter to systems described by nonlinear ordinary differential equations.

In order to estimate plasma insulin concentration from CGM data, Hovorka's glucose-insulin model is incorporated in an EKF. Moreover, an extra equation is added to the system to describe the relationship between blood glucose and interstitial glucose measured by continuous glucose monitors. The function f(x(t), u(t)) is described by the dynamical equations exposed into Table XVI, while h(x(t))=IG(t), as only interstitial glucose concentration can be measured by SC glucose monitors.

Because CGM data are reported every five minutes, a continuous-discrete extended Kalman filter (CDEKF) is used. The CDEKF is the generalization of the Kalman filter to nonlinear systems with continuous-time state equations and discrete-time measurements. These type of systems can be expressed by:

$$\dot{x} = f(x(t), u(t)) + G(t)\omega, \omega(t) \sim N(0, Q) \quad (130)$$

$$z(t_k) = h(x(t_k)) + v(t_k), v(t_k) \sim N(0, R)$$

Table XVII summarizes a CDEKF according to one embodiment of this invention,

TABLE XVII

Continuous-Discrete Extended Kalman Filter

Initialization
$P(0) = P_0$, $\hat{x}(0) = \bar{x}_0$ where P is covariance matrix
Time update
Estimate: $\dot{\hat{x}} = f(\hat{x}(t), u(t))$
Error covariance: $\dot{P}(t) = A(\hat{x},t)P(t) + P(t)A(\hat{x},t)^T + GQ(t)G^T$
Measurement update
Kalman gain: $K_k = P^-(t_k)H^T(\hat{x}_k^-)[H(\hat{x}_k^-)P^-(t_k)H^T(\hat{x}_k^-) + R]^{-1}$
Error covariance: $P(t_k) = [I - K_k H(\hat{x}_k^-)]P^-(t_k)]$
Estimate: $\hat{x}_k = \hat{x}_k^- + K_k[z_k - h(\hat{x}_k^-,k)]$
Jacobians $$A(x, t) = \left.\frac{\partial f}{\partial x}\right|_{\hat{x}(t), n(t)}$$

$$H(x) = \frac{\partial h(x, k)}{\partial x}$$

In many state estimators good knowledge of system-dynamics and parameter values are assumed. This assumption is not realistic when the system has nonlinear dynamics and parameter values that are not accurate or constant. State observers can be used to estimate these uncertain parameters by building new extended models in which these parameters are considered as new states with no dynamics. The non-linearities in glucose-insulin dynamics and uncertainties in parameter values can be accommodated by defining extended Hovorka's models such that various parameters are considered as extended states of the model:

$$\frac{d}{dt}\begin{bmatrix} x(t) \\ p(t) \end{bmatrix} = \begin{bmatrix} f(x(t), u(t))|_{p=p(t)} \\ 0 \end{bmatrix} \tag{131}$$

The parameters with the greatest impact on plasma Insulin concentration are $k_c$ (plasma insulin elimination rate) and $t_{max,I}$ (time to maximum insulin, absorption). Hence, both parameters have been selected as uncertain states in extended Hovorka's models.

Figure 40:
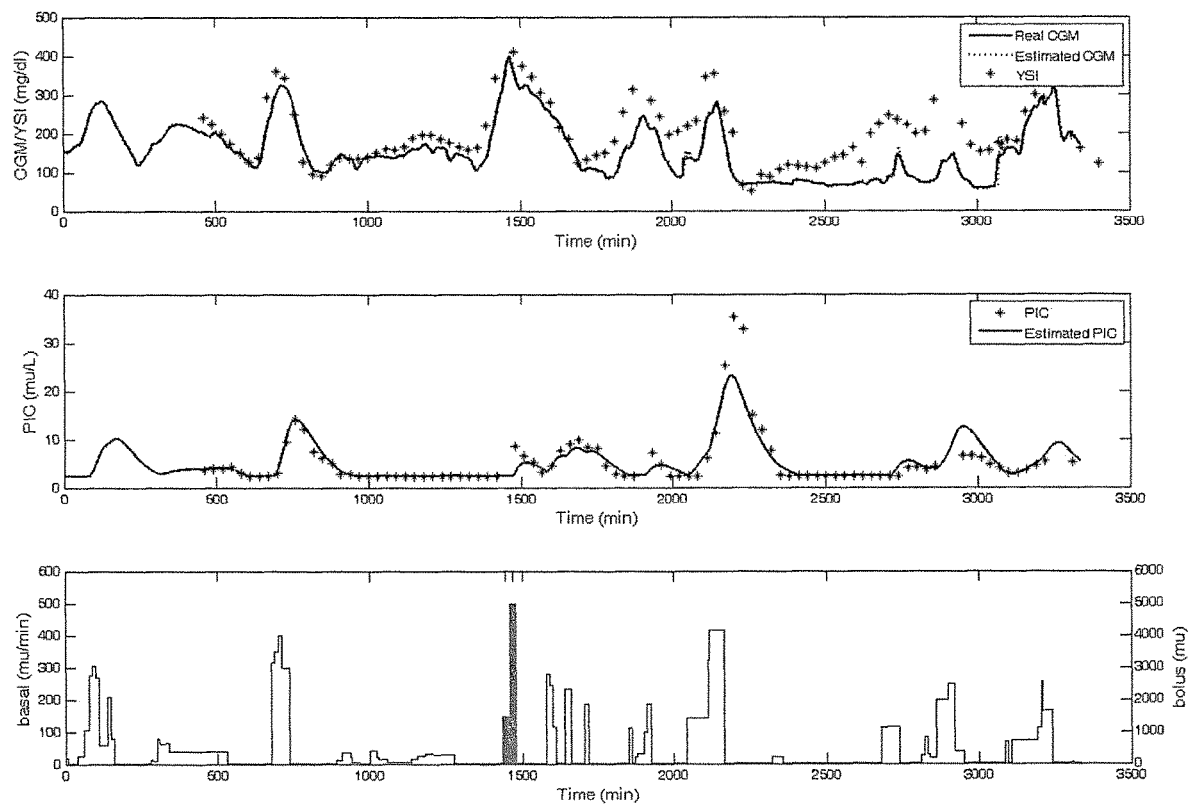

In the following example, subjects were young adults aged 18-35 years with T1D. All subjects used insulin pump therapy, were healthy and physically active. To analyze the performance of proposed method, the following clinical data were required for each experiment:

CGM—available every five minute
PIC—available every thirty minutes
Insulin information—basal and bolus insulin based on adjustments made to insulin infusion rate of the pump The CDEKF module was developed in MATLAB. Simulation results for one closed-loop AP experiment was presented and the estimated values for COM and PIC were compared with clinical data. Based on simulation results and comparison with experimental data, as shown in FIG. 40, the proposed method was able to estimate accurately PIC and COM in real time. The method will be beneficial as a module for an AP system in terms of real time estimation of plasma insulin concentrations.

In another embodiment of this invention, the method for PIC estimation uses COM measurements by modifying Bergman's minimal model and integrating it to an unscented Kalman filter (UKF). UKF overcomes the drawbacks of linear approximation at an operating point and calculation of Jacobian matrices in the EKF by using a minimal set of carefully chosen sample points. Contrary to the original Bergman's model, the unknown model parameters are defined to be time-varying to deal with intra- and inter-subject dynamic variability. A partial least squares (PLS) model based on each patient's demographic information, such as body weight, height, BMI and total daily insulin dose is developed for prediction of initial values of the unknown model parameters. The method desirably uses only real-time CGM measurements. The method is likewise implemented as a module of the integrated multivariable adaptive artificial pancreas of this invention and no other manual information such as meal announcement or carbohydrate intake is used.

A modified version of the extended minimal model was developed and used, similar to that shown in FIG. 11 above. The insulin dynamics were described with three cascade compartments with time-varying model parameters $\tau_1(t)$, $\tau_2(t)$, $p_1(t)$, $p_2(t)$, $p_3(t)$, $p_4(t)$, $V_{ins}(t)$:

$$\frac{dI_{SC}(t)}{dt} = -\frac{1}{\tau_2(t)}I_{SC}(t) + \frac{u_{ins}(t)}{\tau_2(t)v_{ins}(t)} \tag{132}$$

$$\frac{dI_P(t)}{dt} = -\frac{1}{\tau_2(t)}I_P(t) + \frac{1}{\tau_2(t)}I_{SC}(t) \tag{133}$$

$$\frac{dI_{eff}(t)}{dt} = -p_2(t)I_{eff}(t) + p_3(t)I_P(t) \tag{134}$$

$$\frac{dG(t)}{dt} = -p_1(t)G(t) - p_4(t)I_{eff}(t)G(t) + p_1(t)G_b \tag{135}$$

$$\frac{d\tau_1(t)}{dt} = \tag{136}$$

$$\frac{d\tau_2(t)}{dt} = \frac{dp_1(t)}{dt} = \frac{dp_2(t)}{dt} = \frac{dp_3(t)}{dt} = \frac{dp_4(t)}{dt} = \frac{dV_{ins}(t)}{dt} = 0$$

where $I_{SC}$, $I_P$, $I_{eff}$, G represent subcutaneous, plasma and effective insulin concentrations and glucose concentration, respectively. As shown in Eqs. (132-136), all unknown model parameters were defined to be time-varying in order to accommodate inter- and intra-subject dynamical variability. Equation (136) states that their variation over time is zero, however, their changes over time are defined to be functions of white noise later in the estimation step.

Consumed meals have significant effects, on the glucose compartment in Eq. (135). However, since the method is a part of the fully automated AP system of this invention, no manual information about meals was provided. Thus, the meal effect was considered as a disturbance to the system and was not modeled in the main model equations (132)-(136). Instead, the tuning parameters of the estimators were defined in such a way that the nutrition effect was accommodated. The equations were discretized using first forward difference derivative approximation with a 5-minutes sampling time and a nonlinear state-space model was written as:

$\xi(k+1)=f(\xi(k),u(k))+w(k)$ $y(k)=g(\xi(k),u(k))+v(k)$ (137)

where $\xi(k)$, $u(k)$, $y(k)$ are model states ($I_{SC}(t)$, $I_P(t)$, $I_{eff}(t)$, $G(t)$, $\tau_1(t)$, $\tau_2(t)$, $p_1(t)$, $p_2(t)$, $p_3(t)$, $p_4(t)$, $V_{ins}(t)$), input (infused insulin) and output (measured glucose), respectively. $w(k)$ and $v(k)$ represent model and measurement noises. The changes over time in the unknown time-varying model parameters listed in Eqs. (132-136) and the nutrition effect (See FIG. 11) are defined to be function of $w(k)$ and $v(k)$. The state-space model in Eq. (137) is used in an UKF for state and parameter estimation. The details of the UKF algorithm are presented herein above.

The two unknown model parameters $\tau_1$ and $\tau_2$ in Eqs. (132) and (133) have significant effect on PIC estimations and their initial values are critical for improving the accuracy of estimated PIC values. PLS models were developed for the initial guess of the two parameters. PLS is a multivariate regression method for modeling the relationship between two groups of data (explaining the variations in Y by using X) with many noisy, collinear variables and even incomplete data. PLS models summarize the repressor (input) variables matrix X to extract the most predictive information for the response variables Y and maximize the covariance between X and Y. The outer relations for X and Y are $$X = TP^T + E = \Sigma_{t=1}^a t_t p_t^T + E \quad (138)$$

$$Y = UQ^T + F = \Sigma_{t=1}^a u_t q_t^T + F \quad (139)$$

where E and F represent the residuals matrices. Linear combinations of x vectors (single observation vector) are calculated from the latent variable scores $t_t = w_t^T x$ and those for the y vectors (response variables, $\tau_1$ and $\tau_2$ in this case) from $u_t = q_t^T y$ so that they maximize the covariance between X and Y explained at each dimension. $w_t$ and $q_t$ are the weight sectors and $p_t$ are the loading sectors of X. The PLS model can be built by using the nonlinear iterative PLS algorithm (NIPALS). The X matrix consists of demographic information such as body weight, height, BMI, total daily insulin dose and the Y matrix is defined to be the two critical parameters $\tau_1$ and $\tau_2$ in Eqs. (129) and (133). Once the initial values for the parameters are determined from the PLS models that are developed by using training data, UKF can provide the estimates of PIC by using only CGM measurements.

Pearson's correlation coefficient, which is a measure of the strength of the linear relationship between two variables, is used to show the correlation between the estimated and measured PIC samples. Pearson's correlation coefficient R is calculated as:

$$R = \frac{([m\sum_{t=1}^m PIC_t \times \widehat{PIC}_t] - [\sum_{t=1}^m PIC_t] \times [\sum_{t=1}^m \widehat{PIC}_t])}{\sqrt{[m\sum_{t=1}^m PIC_t^2 - (\sum_{t=1}^m PIC_t)^2][m\sum_{t=1}^m \widehat{PIC}_t^2 - (\sum_{t=1}^m \widehat{PIC}_t)^2]}} \quad (140)$$

where $\widehat{PIC}_t$ is the estimated PIC at time t. Pearson's R can range from −1 to 1. An R of −1 indicates a perfect negative linear relationship between variables, an R of 0 indicates no linear relationship between variables, and an R of 1 indicates a perfect positive linear relationship between variables.

The method was tested for two sets of data where the pharmacodynamics of insulin were different. The test indicated that the proposed method can estimate PIC accurately even under challenging and difficult conditions since the dynamics of insulin infusion to the subcutaneous tissue (and diffusion to the bloodstream) were different in the two clamp studies. Thus the proposed algorithm can estimate PIC with a high accuracy. The adaptive nature of the algorithm can deal with dynamic changes in the human body and provide good estimates of PIC.

Thus the invention provides an automated method and device for monitoring and/or treating glucose levels of a patient with diabetes. The various aspects of the method can implemented individually or collectively as modules in a new or existing artificial pancreas system to provide a fully automated, closed-loop device.

While in the foregoing detailed description this invention has been described in relation to certain preferred embodiments thereof, and many details have been set forth for purposes of illustration, it will be apparent to those skilled in the art that the invention Is susceptible to additional embodiments and that certain of the details described herein can be varied considerably without departing from the basic principles of the invention.

We claim:

1. A method for monitoring and/or treating glucose levels of a patient with diabetes, the method comprising:
    automatically monitoring a glucose concentration level in the patient with a continuous glucose monitor worn by the patient to obtain a measured glucose level;
    automatically monitoring physiological variables of the patient using at least one physiological sensor worn by the patient to obtain measured physiological variables;
    automatically receiving the glucose concentration level and the physiological variables at a controller in communication combination with the continuous glucose monitor and the at least one physiological sensor;
    the controller automatically determining a physiological state of the patient from the measured physiological variables by automatically matching the measured physiological variables to one of a plurality of predetermined classified physiological states stored in the controller;
    the controller automatically estimating a future glucose level of the patient as a function of the measured glucose level, at least one of the measured physiological variables, and the determined physiological state of the patient;
    the controller automatically computing the insulin dose to be infused and delivering instruction to an insulin pump to deliver the insulin dose to the patient; and
    automatically updating the controller using further glucose measurements from the continuous glucose monitor and further physiological variables from the at least one physiological sensor.

2. The method according to claim 1, further comprising:
    the controller automatically determining a change between at least two measured glucose levels that exceeds a predetermined value; and
    the controller automatically comparing the change in the measured glucose level to any change in physiological state to determine a cause of the change in the measured glucose level.

3. The method according to claim 1, wherein the physiological state is determined using real time streaming data from the at least one physiological sensor and is selected from sleep, physical activity, stress, or combinations thereof.

4. The method according to claim 3, wherein the at least one physiological sensor worn by the patient measures physiological variables selected from a combination of movement, skin temperature, dissipated heat from the body, galvanic skin response, heart rate, ECG, respiration rate, posture, or body position.

5. The method according to claim 1, further comprising automatically predicting and alarming the patient of a predicted future low blood glucose concentration and the controller automatically determining and suggesting responsive measures including carbohydrate consumption to prevent low blood glucose concentration.

6. The method according to claim 1, further comprising automatically detecting food consumption and/or a rapid glucose level increase without manual input by the patient.

7. The method according to claim 1, wherein the physiological state is exercise and further comprising automatically determining an intensity, type, and/or duration of the exercise, wherein the predetermined classified physiological states includes predetermined aerobic and anaerobic intensity exercise classifications.

8. The method according to claim 1, wherein the physiological state is acute stress.

9. The method according to claim 1, wherein the physiological state is sleep and further comprising automatically determining a sleep pattern and stage of sleep for the patient.

10. The method according to claim 1, further comprising the controller automatically monitoring for and determining a faulty or missing measurement information transmitted by the continuous glucose monitor or the physiological sensors and estimating measurements of any malfunctioning sensor for the predicting.

11. The method of claim 1, wherein the predetermined classified physiological states include a predetermined acute stress classification and predetermined sleep stage or sleep pattern classification.

12. A device for monitoring and/or treating patient glucose levels, the device comprising:
 a continuous glucose monitor adapted to measure a glucose level of a patient;
 a physiological status monitoring system worn by the patient and adapted to measure physiological variables of the patient; and
 an automatic controller in communication with the glucose monitor and the physiological status monitoring system, the controller including a recordable medium comprising a plurality of stored predetermined classified physiological states selected from physical activity states, stress states, and sleep states, wherein the controller is configured to compare the measured physiological variables to the stored predetermined classified physiological states to predict a future glucose measurement.

13. The device according to claim 12, wherein the controller comprises a recursively updated stable multivariate time-series model.

14. The device according to claim 12, further comprising a hypoglycemia detection alarm.

15. The device according to claim 12, wherein the controller is configured to detect food consumption and to compute a bolus insulin amount without manual input by the patient.

16. The device according to claim 12, further comprising an estimator adapted to estimate a future plasma glucose concentration and/or a future plasma insulin concentration.

17. The device according to claim 12, wherein the controller detects and classifies the physiological state as a function of activity intensity and duration, body position, heart rate, respiration pattern, or a combination thereof.

18. The device according to claim 12, further comprising an insulin pump in combination with the controller, wherein the controller controls an insulin infusion as a function of the predicted future glucose level.

19. A method for monitoring and/or treating glucose levels of a patient with diabetes, the method comprising:
 automatically monitoring a glucose concentration level in the patient with a continuous glucose monitor worn by the patient to obtain a measured glucose level;
 automatically measuring physiological variables of the patient using at least one physiological sensor worn by the patient to obtain measured physiological variables;
 automatically receiving the glucose concentration level and the physiological variables at a controller in communication combination with the continuous glucose monitor and the at least one physiological sensor;
 the controller automatically interpreting the measured physiological variables to determine a physiological state of the patient, the physiological state selected from a group consisting of exercise, stress, sleep, or combinations thereof;
 the controller automatically estimating a future glucose level of the patient as a function of the measured glucose level and the determined physiological state of the patient;
 the controller automatically computing the insulin dose to be infused and delivering instruction to an insulin pump to deliver the insulin dose to the patient; and
 automatically updating the controller using further glucose measurements from the continuous glucose monitor and further physiological variables from the at least one physiological sensor.

20. The method of claim 19, wherein automatically interpreting the measured physiological variables comprises automatically matching the measured physiological variables to one of a plurality of predetermined classified exercise states, stress states, and sleep states stored in the controller.

21. The method of claim 20, wherein the predetermined classified exercise states include predetermined aerobic and anaerobic intensity classifications, the predetermined stress states include predetermined acute stress classifications, and the predetermined sleep states include predetermined sleep stage classification.

* * * * *